(12) United States Patent
Schmitthenner et al.

(10) Patent No.: US 10,610,608 B2
(45) Date of Patent: Apr. 7, 2020

(54) MODULAR IMAGING AGENTS CONTAINING AMINO ACIDS AND PEPTIDES

(71) Applicants: Hans F. Schmitthenner, Rush, NY (US); Stephanie Beach, Douglassville, PA (US); Taylor Barrett, Middletown, PA (US); Chelsea Weidman, Rochester, NY (US)

(72) Inventors: Hans F. Schmitthenner, Rush, NY (US); Stephanie Beach, Douglassville, PA (US); Taylor Barrett, Middletown, PA (US); Chelsea Weidman, Rochester, NY (US)

(73) Assignee: Rochester Institute of Technology, Rochester, NY (US)

( * ) Notice: Subject to any disclaimer, the term of this patent is extended or adjusted under 35 U.S.C. 154(b) by 0 days.

(21) Appl. No.: 14/449,943

(22) Filed: Aug. 1, 2014

(65) Prior Publication Data
US 2015/0038672 A1 Feb. 5, 2015

Related U.S. Application Data

(60) Provisional application No. 61/861,214, filed on Aug. 1, 2013.

(51) Int. Cl.
| | |
|---|---|
| *A61K 49/14* | (2006.01) |
| *A61K 49/10* | (2006.01) |
| *A61K 49/00* | (2006.01) |
| *C07F 1/08* | (2006.01) |
| *C07F 5/00* | (2006.01) |

(52) U.S. Cl.
CPC .......... *A61K 49/14* (2013.01); *A61K 49/0032* (2013.01); *A61K 49/0056* (2013.01); *A61K 49/108* (2013.01); *C07F 1/08* (2013.01); *C07F 5/00* (2013.01)

(58) Field of Classification Search
None
See application file for complete search history.

(56) References Cited

U.S. PATENT DOCUMENTS

| | | | |
|---|---|---|---|
| 5,679,318 A | 10/1997 | Vanderheyden et al. | |
| 6,083,486 A | 7/2000 | Weissleder et al. | |
| 6,719,958 B1 | 4/2004 | Gozzini et al. | |
| 8,021,646 B2 | 9/2011 | Sulzer et al. | |
| 2004/0022733 A1 | 2/2004 | Uzgiris | |
| 2011/0014120 A1 | 1/2011 | Brechbiel et al. | |

FOREIGN PATENT DOCUMENTS

| | | |
|---|---|---|
| CN | 101564540 A | 10/2009 |
| EP | 1077998 A1 | 2/2001 |
| EP | 1412383 A2 | 4/2004 |
| EP | 1420681 A2 | 5/2004 |
| WO | WO 8706229 A1 | 10/1987 |
| WO | WO9104057 A1 | 4/1991 |
| WO | WO9910016 A1 | 3/1999 |
| WO | WO99/10016 * | 6/1999 |
| WO | WO 0071526 A1 | 11/2000 |

OTHER PUBLICATIONS

Hainsworth et al., Bioconjugate Chem., 2005, 16, 1468-1474.*
Grunberg et al., Plos One, 2013, 8(4), 1-10.*
International Search Report and Written Opinion of corresponding PCT Application No. PCT/US2014/049462 dated Nov. 25, 2014.
Hainsworth, James et al., Preparation and Characterization of a DOTA-Lysine-Biotin Conjugate as an Effector Molecule for Pretargeted Radionuclide Therapy, Bioconjugate Chemistry, 2005, vol. 16, pp. 1468-1474.
Grunberg, Jurgen, et al., DOTA Functionalized Polylysine: A High Number of DOTA Chelates Positively Influences the Biodistribution of Enzymatic Conjugated Anti-Tumor Antibody chCE7agl, PLOS One, Apr. 2013, vol. 8, No. 4, p. e60350 (pp. 1-10).
Curtet, Chantal, et al., Polylysine-Gd-DTPAn and Polylysine-Gd-DOTAn Coupled to Anti-CEA F (ab)2 Fragments as Potential Immunocontrast Agents: Relaxometry, Biodistribution, and Magnetic Resonance Imagine in Nude Mice Grafted with Human Colorectal Carcinoma, Investigative Radiology, Oct. 1998, vol. 33, No. 10, pp. 752-761.
Weissleder, R. "Molecular imaging in cancer", Science, 2006, 312, 5777: 1168-1171.
Weissleder, R. Mahmood, U., "Molecular Imaging", Radiology, 2010, 219: 316-333.
Lee, S., Xie, J., and Chen, X.; "Peptide-based probes for targeted molecular imaging", Biochemistry, 2010, 49 (7): 1364-1376.
James, Michelle L. , Gambhir, Sanjiv S., A Molecular Imaging Primer: Modalities, Imaging Agents, and Applications, Physiological Reviews, 2012; 92; 897-965.
Sherry, A.D., Caravan, P., Lenkinski, R.E., A Primer on Gadolinium Chemistry, J Magn Reson Imaging. Dec. 2009; 30 (6): 1240-1248.
Leun-Rodriguez L. M. Kovacs, Z, Dieckmann, G. R, Sherry, A. D., "Solid-Phase Synthesis of DOTA Peptides"; Chem. Eur. J. 2004, 10, 1149-1155.
Leun-Rodriguez L. M. Kovacs "The Synthesis and Chelation Chemistry of DOTA-Peptide Conjugates", Bioconjugate Chemistry, 19, 2, 391-402, 2008.
Culver, J., Akers, W., Achilefu, S., "Multimodality Molecular Imaging with Combined Optical and PECT/PET" Modalities, Journal of Nuclear Medicine, 2008, 49: 169-172.

(Continued)

*Primary Examiner* — Maury A Audet
(74) *Attorney, Agent, or Firm* — Bond, Schoeneck & King, PLLC; Joseph Noto

(57) ABSTRACT

Targeted molecular imaging agents (TMIAs) are derived from coupling together pre-formed amino acids with imaging agents attached to their side chains. These peptide-based imaging agents may synthesized from a single or multiple preformed amino acids containing multi-modal, multi-chelated metal, multi-dye imaging agents, or combinations of these, on the side chains of resultant peptides. These imaging amino acids or peptides may be conjugated directly, or activated, or attached to linkers to which targeting groups, such as peptides, proteins, antibodies, aptamers, or small molecule inhibitors, may be conjugated in the final steps of the synthesis to form a wide variety of TMIAs.

18 Claims, 7 Drawing Sheets

(56) References Cited

OTHER PUBLICATIONS

Jennings, L., Long, N. "'Two is better than one'—Probes for dual-modality molecular imaging", Chem. Commun., 2009, 3511-3524.
Zhang, Z., Liang, K., Bloch, S., Berezin, M., Achilefu, S., Monomolecular multimodal fluorescence-radioisotope imaging agents, Bioconjugate Chem., 2005, 16 (5): 1232-1239.
Wu X, Burden-Gulley S, Yu G, Tan M, Lindner D, Brady-Kalnay SM, Lu Z., "Synthesis and evaluation of a peptide targeted small molecular Gd-DOTA monoamide conjugate for MR molecular imaging of prostate cancer", Bioconjug Chem. 2012; 23(8):1548-56.
Boros, E, Polasek M., Zang, Z., Caravan P, "Gd(DOTAla): A Single Amino Acid Gd-complex as a Modular Tool for High Relaxivity MR Contrast Agent development", J. Am. Chem. Soc. 2012; 134:19858-19868.
Azhdarinia A, Wilganowski N, Robinson H, Ghosh P, Kwon S, Za Waunyka W, Lazard B, Davis A, Olmsted-Davis E, Sevick-Muraca E, "Characterization of chemical, radiochemical and optical properties of a dual-labeled MMP-9 targeting peptide", Bioorg Med Chem. 2011;19(12):3769-76.
Azhdarinia A, Ghosh P, Ghosh S, Wilganowski N, Sevick-Muraca DE., "Dual-Labeling Strategies for Nuclear and Fluorescence Molecular Imaging: A Review and Analysis", Mol Imaging Biol 2012;14(3):261-76.
Edwards WB, Akers WJ, Ye Y, Cheney PP, Bloch S, Xu B, Laforest R, Achilefu, S. "Multimodal imaging of integrin receptor-positive tumors by bioluminescence, fluorescence, gamma scintigraphy, using a cyclic RGD peptide labeled with a near-infrared fluorescent dye and a radionuclide", Molecular Imaging, 2009, 8:101-10.
Langereis, S., de Lussanet, Q.G., van Genderen, MHP, Meijer,E.W., "Evaluation of Gd(III)DTPA-terminated poly (propylene imine) dendrimers as contrast agents for MR imaging", NMR Biomed. 2006,19:133-141.
Guo, K., Berezin, M., Zheng, J., Akers, W., Zheng, J. Lin, F., Teng, B., Vasalatiy, O., Gandjbakhche, A., Griffiths, G L., Achilefu, S., "Near infrared-fluorescent and magnetic resonance imaging molecular probe with high T1 relaxivity for in vivo multimodal imaging", Chem. Commun., 2010, 46:3705-3707.
Sancey, L, Garanger, E, Foillard, S, Schoehn, G, Hurbin A, Albiges-Rizo C, Boturyn, D, Souchier, C., Grichine, A., Dumy, P. "Clustering and internalization of integrin αvβ3 with a tetrameric RGD-synthetic peptide". Molecular Therapy 2009, 17: 837-843.
Indrevoll B, Kindberg GM, Solbakken M, Bjurgert E, Johansen JH, Karlsen H, Mendizabal M, Cuthbertson A. "NC-100717: a versatile RGD peptide scaffold for angiogenesis imaging", Bioorg Med Chem Lett. Dec. 15, 2006;16 (24):6190-3.
Tan M, Wu X, Jeong EK, Chen Q, Lu ZR, "Peptide-targeted Nanoglobular Gd-DOTA monoamide conjugates for magnetic resonance cancer molecular imaging". Biomacromolecules, 2010;11(3):754-61.
Hornak, J.P., "The Basics of MRI", Interactive Learning Software, Henrietta, NY 2014 (http://www.cis.rit.edu/htbooks/mri/).
Ferreira MF, Martins AF, Martins CI, Ferreira PM, Tóth E, Rodrigues TB, Calle D, Cerdan S, López-Larrubia P, Martins JA, Geraldes CF., "Amide conjugates of the DO3A—N-(α-amino)propionate ligand: leads for stable, high relaxivity contrast agents for MRI?" Contrast Media Mol Imaging. 2013 8(1):40-9.
Z. Chen, Y. Wang, Y. Lin, et al., "Advance of Molecular Imaging Technology and Targeted Imaging Agent in Imaging and Therapy," BioMed Research International, 2014.
G. Stasiuk and N. Long, "The ubiquitous DOTA and its derivatives: the impact of 1,4,7,10-tetraazacyclododecane-1,4,7,10-tetraacetic acid on biomedical imaging," Chem. Commun., vol. 49, pp. 2732-2746, 2013.
M. Hüber, A. Staubli, K. Kustedjo, et al., "Fluorescently Detectable Magnetic Resonance Imaging Agents," Bioconjugate Chem., vol. 9, pp. 242-249, 1998.
Pasha, G. Tircso, E.T. Benyo, E. Brucher, and A.D. Sherry, "Synthesis and characterization of DOTA-(amide)4 derivatives: equilibrium and kinetic behavior of their lanthanide(III) complexes," Eur. J. Inorg. Chem., pp. 4340-4349, 2007.
W. Cacheris, S. Nickle, A. Sherry, "Thermodynamic study of lanthanide complexes of 1,4,7-triazacyclononane-N,N',N"-triacetic acid and 1,4,7,10-tetraazacyclododecane-N,N',N",N'''-tetraacetic acid, Inorg. Chem. vol. 26, pp. 958-960, 1987.
C. Gros, A. Eggenspiller, A. Nonat, et al, "New potential bimodal imaging contrast agents based on DOTA-like and porphyrin macrocycles," Med. Chem. Comm., vol. 2, pp. 119-125, 2011.
K. Overoye-Chan, S. Koerner, R. Looby, et al. "EP-2104R: A Fibrin-Specific Gadolinium-Based MRI Contrast Agent for Detection of Thrombus," J. Am. Chem. Soc., vol. 130, pp. 6025-6039, 2008.
Barge Al, Cappelletti E, Cravotto G, Ferrigato A, Lattuada L, Marinoni F, Tei L., Synthesis of functionalised HP-DO3A chelating agents for conjugation to biomolecules; Org Biomol Chem. Sep. 21, 2009;7(18):3810-6.
Faivre-Chauvet et al., The Most Suitable Radionuclides for Immunoscintigraphic Imaging, in Handbook of Targeted Delivery of Imaging Agents, Jan. 1, 1995, CRC Press, XP055339177, pp. 77-79.
Vladimir Tolmachev, Choice of Radionuclides and Radiolabelling Techniques—Labelling Methods for Radioactive Metals, In Targeted Radionuclide Tumor Therapy—Biological Aspects, Jan. 1, 2008, Springer, XP055339164, ISBM: 978-1-4020-8696-0, pp. 154-156.
Liu Yuanfang et al., Radiolabeling of Monoclonal Antibodies with Metal Chelates, DK Mitteilungen, Beuth Vertrieb GMBH, Berlin, DE, vol. 63, No. 3, Jan. 1, 1991, pp. 427-463, XP001147588.
Hainsworth J. et al., Preparation and Characterization of a DOTA-Lysine-Biotin Conjugate as an Effector Molecule for Pretargeted Radionuclide Therapy, Bioconjugate Chemistry, vol. 16, No. 6, Nov. 16, 2005, pp. 1468-1474, XP002612278, ISN: 1043-1802, DOI: 10.1021/BC050188H.
Supplemental Partial European Search Report in corresponding European patent application No. EP14832797.6 dated Mar. 2, 2017.
EPO Form 1503 03.82 and Search Report, EP Application No. 14 83 279, pp. 1-21, dated Jan. 27, 2017.

* cited by examiner

MODULAR IMAGING AGENTS CONTAINING AMINO ACIDS AND PEPTIDES

CROSS REFERENCE

This application claims the benefit of the filing date of U.S. Provisional Patent Application Ser. No. 61/861,214, filed Aug. 1, 2013, which is hereby incorporated by reference in its entirety.

FIELD

This invention relates to modular imaging agents containing amino acids and peptides and methods of synthesizing such agents. In particular, this invention relates to modular imaging agents containing amino acids and peptides, targeted agents thereof and methods of synthesizing such agents and targeted agents thereof.

BACKGROUND

Early detection of diseased cells by molecular imaging is viewed as the best hope by many in treating cancer and other diseases. By using agents that attach selectively to diseased cells, the ability to image disease states at the cellular level is further enhanced. This affinity may be achieved through the use of targeting agents which seek receptors or biomarkers in diseased cells. As a result of these advances there has been a significant acceleration of research, leading to an increased need for safe and effective targeted molecular imaging agents (TMIAs) for MRI, PET, SPECT, PAI, and NIR fluorescence imaging and combinations of those. Dual modal TMIAs can include agents for MRI-PET, MRI-FLA, and MRI-PAI. Tri-modal agents may also be combined in one agent.

In conventional imaging agent synthesis, one in which a metal is incorporated into DOTA or related chelating groups like DTPA, DO3A, TE2A. NOTA, CB-TETA, a metal such as Gd (for MRI) or radioactive metals such as Tc, In, Ga and Cu (for PET or SPECT) are typically inserted during the final steps of a synthesis, regardless of whether the agent is a peptide, protein, antibody, nanobody, or large assembly such as a dendrimers, polymers, nanoparticles, or small molecules. It is most common in a multi-step synthesis to bring in a DOTA or DTPA, for example, in the second to last step and introduce Gd or the radioactive metal as the last step. This is because DOTA contains four amines and four acids which are problematic in chemical reactions like peptide coupling.

In the synthesis of imaging agents a common solution is to bring a t-butyl ester protected form of DOTA and to carry this fully protected chelating group through the synthesis. An example is the elaboration of peptide based imaging agents utilizing a tri-t-butyl ester of DOTA on the side chain of lysine as a starting material (Leun-Rodriguez, et al). Fully protected DOTA precursors are commercially available containing t-butyl esters on the multi acid groups. There are no commercially available alternative protecting groups apart from this form. The removal of t-butyl groups requires strong acids like TFA, and many peptides, proteins, antibodies, and other groups on imaging agents such as dyes, and in particular many NIR dyes, may not be stable to such harsh conditions.

Another method of introducing DOTA, DTPA and other groups is to react an activated form of the unprotected chelating ligand (NHS ester or isothiocyanate are examples) directly, followed by insertion of the metal, such as Gd. Very few chemical steps such as coupling or conjugation of additional targeting groups or imaging agents can occur in the presence of the unprotected, non-chelated DOTA because the acids are reactive. In addition, it is difficult to purify intermediates containing the multiple unprotected acid and amine groups.

These restrictions severely limit the way in which DOTA and metal-DOTA complexes for MRI and radioactive metals for PET can be incorporated into new imaging agents. It would therefore be very useful to have an alternative way to add chelating groups containing metals, to allow practical synthetic approaches to new types of imaging agents.

There are few methods of combining various dyes for use in NIRF or PAI imaging in a straightforward and easily applicable manner. Likewise, there are few generally applicable methods for combining dyes and metal-chelating complexes into the same imaging agent while also providing a method for conjugating targeting groups as a final step.

It would be therefore useful to provide routes to a wide variety of targeted molecular imaging agents (TMIAs) by providing imaging agents comprised of pre-formed dyes and metal chelates, either alone or in combination, in a form that could be attached or conjugated to any targeting agent containing a reactive amine, sulfide or carboxylic acid by direct conjugation or by means of a well-established linker.

SUMMARY

In accordance with one aspect of the present invention, there is provided a process for synthesizing a targeted imaging agent including providing a) an amino acid imaging agent having a protected or free acid and a protected or free amine or b) multiple amino acid imaging agents in a peptide chain having a protected or free acid and a protected or free amine; and coupling the a) amino acid imaging agent or b) multiple amino acid imaging agents in a peptide chain to a targeting agent having a free amine, sulfur, or free acid, or c) multiple a) amino acid imaging agents or multiple b) multiple amino acid imaging agents to a targeting agent having multiple free amines, sulfurs, or free acids, in a manner to provide a targeted imaging agent.

A process for synthesizing a targeted imaging agent including providing a) an amino acid imaging agent having a protected or free acid and a protected or free amine or b) multiple amino acid imaging agents in a peptide chain having a protected or free acid and a protected or free amine; and coupling the a) amino acid imaging agent or b) multiple amino acid imaging agents in a peptide chain to a targeting agent having a free amine, sulfur, or free acid, in a manner to provide a targeted imaging agent.

In accordance with another aspect of the present invention, there is provided a process for synthesizing an imaging peptide or imaging agent from a plurality of modular amino acids each having a side chain containing an imaging agent, including deprotecting an amine or an acid of a first modular amino acid having a side chain containing an imaging agent; and coupling the deprotected amine of the first modular amino acid to an acid of a second modular amino acid having a side chain containing an imaging agent, or coupling the deprotected acid of the first modular amino acid having a side chain containing an imaging agent to an amine of the second modular amino acid having a side chain containing an imaging agent.

These and other aspects of the present invention will become apparent upon a review of the following detailed description and the claims appended thereto.

DETAILED DESCRIPTION

Figure 1:
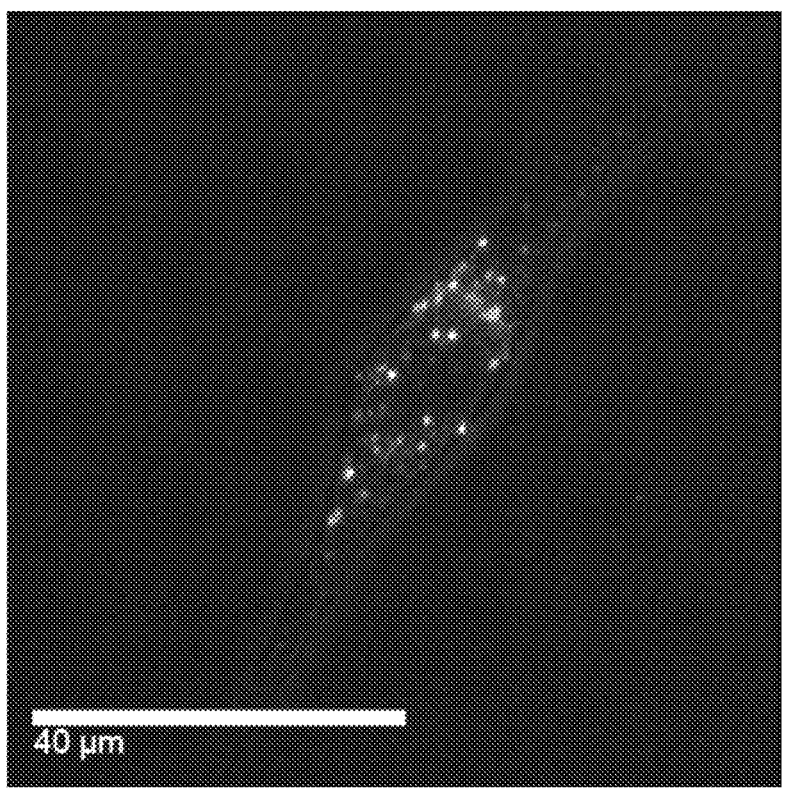
FIG. 1 is a confocal fluorescence microscopy image of Compound (44) after 2 hour's incubation with live A549 cells.

The present invention relates to agents of the broadest utility derived from coupling together pre-formed imaging amino acids containing imaging agents on their sides chains to provide pre-formed multi-modal, multi-chelating metal, multi-dye imaging agents, or combinations of these, that may be activated or attached to linkers to which targeting groups, such as peptides, proteins, antibodies, aptamers, or small molecule inhibitors, may be conjugated in the final steps of the synthesis to form a wide variety of TMIAs.

Targeting agents and targeting molecular imaging agents include peptides, proteins, antibodies, nanobodies, aptamers, small molecules or other targeting agents which bind to, or seek, receptors or biomarkers unique to diseased cells, such as many types of cancer cells, cells present in atherosclerosis, or many brain diseases, as set forth in: (a) Weissleder, R. "Molecular imaging in cancer", *Science*, 2006, 312, 5777: 1168-1171; (b) Weissleder, R. Mahmood, U., "Molecular Imaging", *Radiology*, 2010, 219: 316-333; (c) Lee, S., Xie, J., and Chen, X.; "Peptide-based probes for targeted molecular imaging", *Biochemistry*, 2010, 49 (7): 1364-1376; and (d) James, Michelle L., Gambhir, Sanjiv S., A Molecular Imaging Primer: Modalities, Imaging Agents, and Applications, Physiological Reviews, 2012; 92; 897-965, which are incorporated herein in their entirety. These targeting agents may be conjugated to imaging agents to yield the targeted molecular imaging agents, or TMIAs. As shown in the synthesis schemes below, a single or multi-modal targeted imaging agent containing metal-chelate complexes and/or dyes can be formed by a modular synthesis coupling together amino acids containing imaging moieties on their side chains. By using agents that attach selectively to diseased cells, the ability to image disease states at the cellular level is further enhanced. This affinity may be achieved through the use of targeting agents which seek receptors or biomarkers in diseased cells. As a result of these advances there has been a significant acceleration of research, leading to an increased need for safe and effective targeted molecular imaging agents (TMIAs) for MRI, PET, SPECT, PAI, and NIR fluorescence imaging and combinations of those.

An "amino acid imaging agent" refers to one amino acid in which the side chain has been modified by conjugation to an imaging agent of the types described herein. The term "multiple amino acid imaging agent" refers to a peptide, such as a di-peptide, tri-peptide or longer peptide in which the side chains are similarly modified by conjugation to imaging agents. The latter "multiple amino acid imaging agent" could be prepared from the former "amino acid imaging agent", or starting with one amino acid imaging agent could be prepared by alternate methods.

An illustration of the modular synthesis of a TMIA, where each pre-formed amino acid module can be individually linked to the targeting group or coupled together to form an imaging peptide and then linked to a targeting group is shown in Scheme 1. The approach is based on peptide coupling of modules and, in the peptide convention, the synthetic steps are shown right to left with the final product on the far right. In this case a step can involve a coupling step or a deprotection followed by a coupling step. In this manner, a targeting group containing one or more amine, sulfide or carboxylic acid groups can be conjugated to one or more imaging amino acids, dipeptide or larger peptides where each peptide can contain multiple imaging amino acid modules. The imaging groups on side chains can be single or multiple metal-chelate complexes, single or multiple dyes, or mixtures of complexes and dyes.

Scheme 1: modular synthesis of a dual modal TMIA:

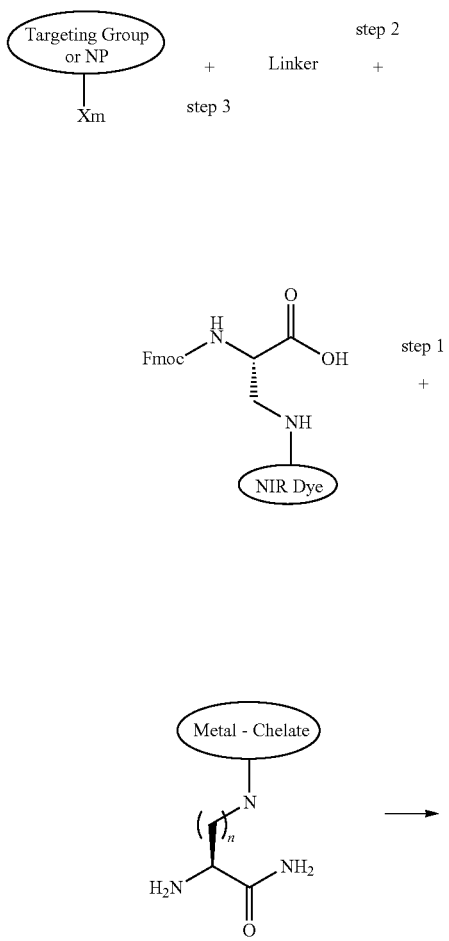

-continued

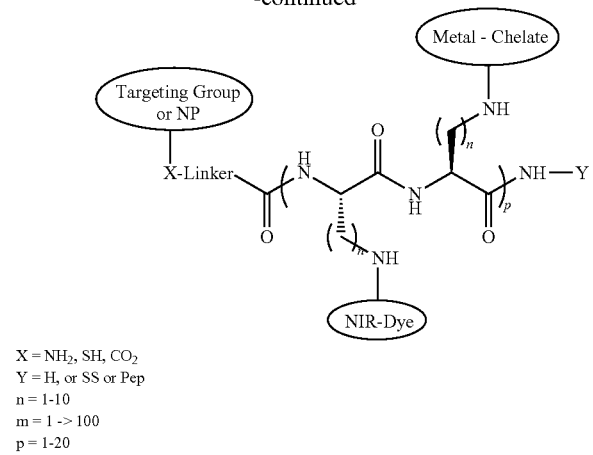

X = NH$_2$, SH, CO$_2$
Y = H, or SS or Pep
n = 1-10
m = 1 -> 100
p = 1-20

Scheme 2: modular synthesis of a multi-metal-chelate TMIA as shown below:

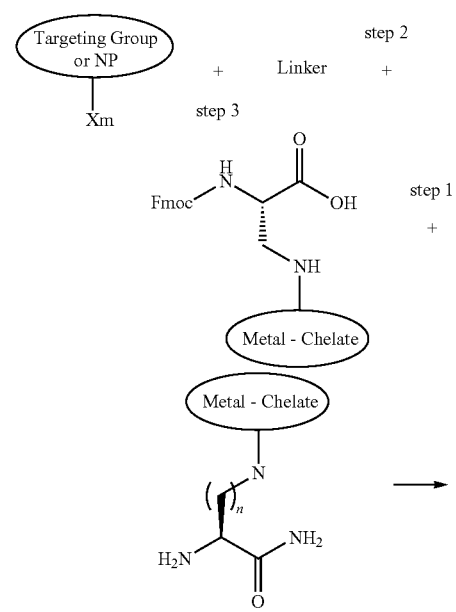

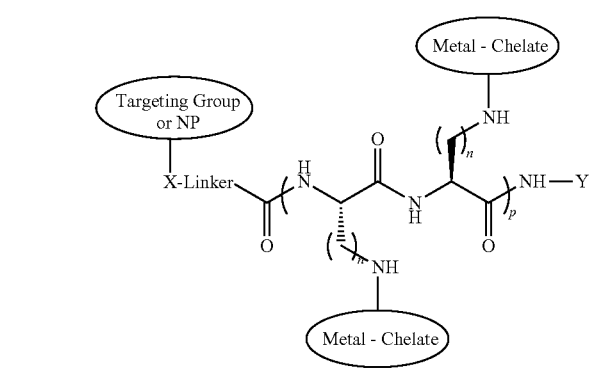

X = NH$_2$, SH, CO$_2$
Y = H, or SS or Pep
n = 1-10
m = 1 -> 100
p = 1-20

Scheme 3: modular synthesis of a multi-dye TMIA as shown below:

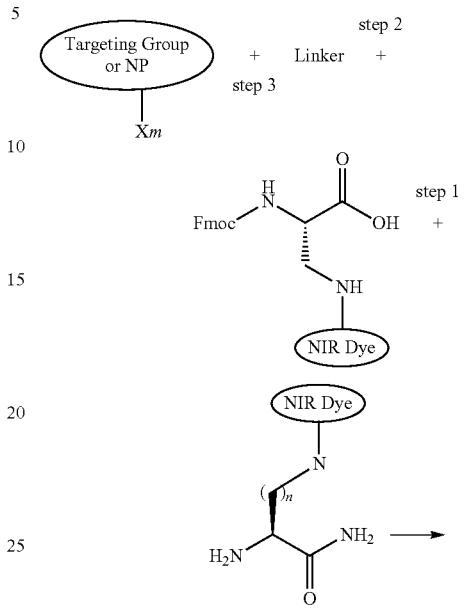

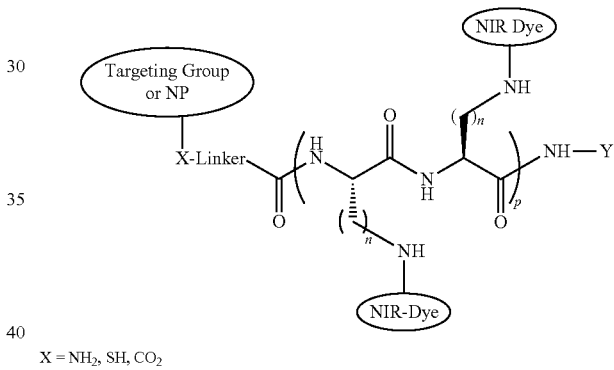

X = NH$_2$, SH, CO$_2$
Y = H, or SS or Pep
n = 1-10
m = 1 ->100
p = 1-20

Scheme 4 illustrates the synthesis of a single amino acid TMIA as shown below. This could be applicable to the amino acid imaging agent containing a NIR dye (not shown).

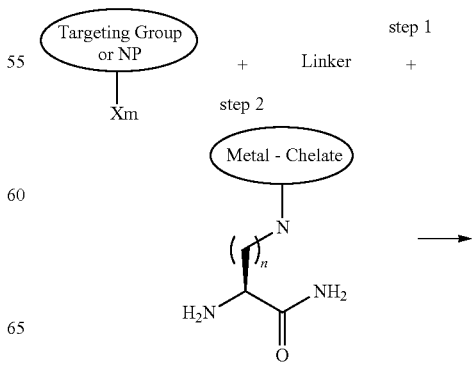

-continued

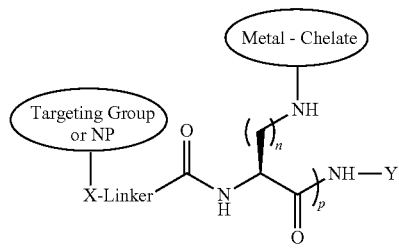

X = NH₂, SH, CO₂
Y = H, or SS or Pep
n = 1-10
m = 1 -> 100

Scheme 5 illustrates the synthesis of a single amino acid TMIA by direct conjugation with no linker. This is applicable to any of the approaches in Schemes 1-4 as well.

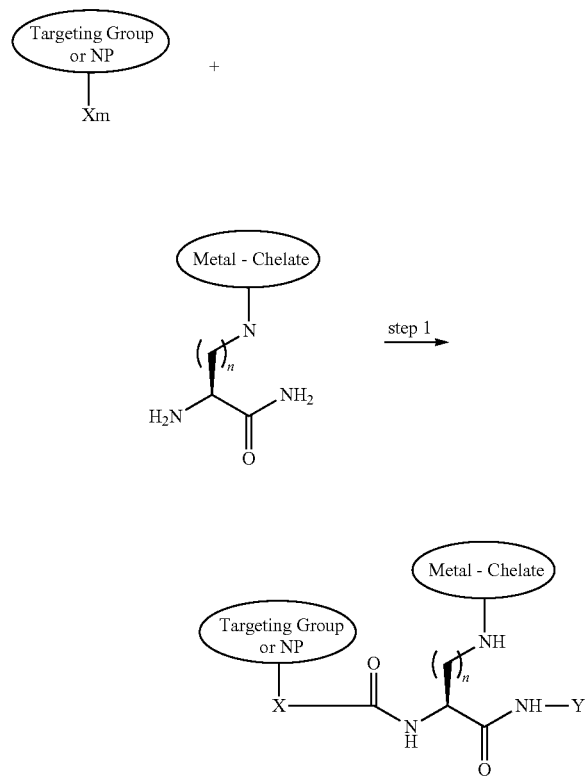

X = NH₂, SH, CO₂
Y = H, or SS or Pep
n = 1-10
m = 1 -> 100

In addition, in each of the examples of Schemes 1-5 it is clear that the targeting groups could be conjugated, via linkers or direct coupling, to multiple imaging agents as denoted by m above. An example of this is proteins or antibodies which may have multiple free amines and sulfides, or nanoparticles which may similarly have multiple amine functionalized sites.

Compounds (I), (II), and (III) shown below illustrate amino acid modules useful for synthesis of molecular imaging agents. Each amino acid can be composed as follows:

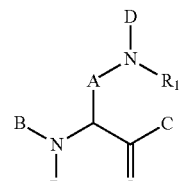  (I)

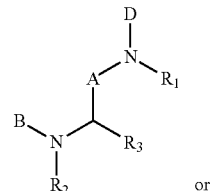  (II)

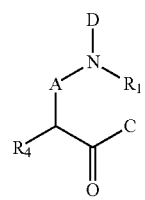  (III)

wherein:

A is $(CH_2)_n$, wherein n is 1-10;
B is a moiety selected from H, Fmoc, Cbz, Boc, Mtt, Alloc, a peptide chain, or a linker selected from SMCC, sulfo-SMCC, DSS, Su, G, Ad, or a targeting moiety selected from a targeting peptide, protein, antibody, nanobody, aptamer, or small molecule by attachment through one or more amines, sulfides, or carboxylic acids on the targeting group attached to a linker or attached directly to the alpha nitrogen, N, adjacent to B;
C is a moiety selected from OH, OBn, OPMB, $OR_5$, an activated acid, such as an NHS ester, OBt ester, TFP ester, isocyante and isothiocyanate, a peptide chain, or linker, such as a preformed DSS or SMCC, or a targeting moiety selected from a targeting peptide, protein, antibody, nanobody, aptamer, or small molecule by attachment through one or more amines, sulfides, or carboxylic acids on the targeting group attached to a linker or attached directly to the carbonyl C; D is a moiety selected from a dye, including NIR and NIRF dyes selected from Cy5.5, Cy7 and other Cy dyes, Alexafluor 680, Alexafluor 750 and other Alexafluor dyes, IR800CW and related NIR dyes, Dylight 680, Dylite 750, Dylite 800 and other Dylite dyes, quencher dyes, and sensitizing dyes, metal-chelate complexes selected from chelating groups DOTA, DTPA, NOTA, TETA, NOTA, TACN, CB-TE2A, Cyclen, DO2A, DO3A, DOT, DOTAM, CB-Cyclam that have been chelated to metals selected from Gd, Eu, Ce, Cu, Tc, Ga, Ge, In, Ho, Tm in their non-radioactive and radioactive forms; or the metal chelate groups selected from these chelating and metal groups conjugated via a linker such as an amide bond, an acetamide bond, or that derived from an activated acid attached to the chelating group via an NHS ester, isocyanate, isothiocyanate, or other activated acid, or chelating groups selected from this group or groups contained within DO3A (DOTAla) and other derivatives of Cyclen;
$R_1$ is H, $CH_3$, or $CH_2CH_3$;
$R_2$ is H, $CH_3$, or $CH_2CH_3$;
$R_3$ is H, $CH_3$, or $CH_2CH_3$;

$R_4$ is H, $CH_3$, or $CH_2CH_3$; and
$R_5$ is H, $CH_3$, or $CH_2CH_3$.

Compounds (IV) and (V) shown below illustrate amino acid modules useful for synthesis of molecular imaging agents. A further description of a di-peptide formed from the aforementioned amino acids module and combination of modules follows. Each amino acid module can be composed as follows:

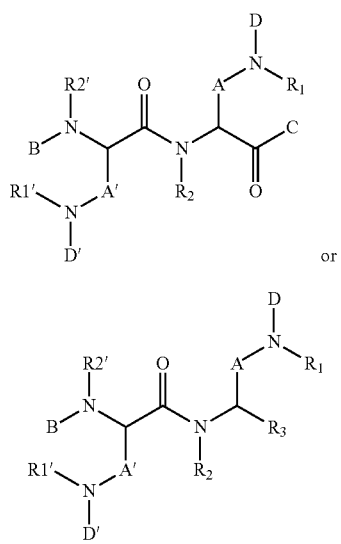

wherein:
A and A' are independently $(CH_2)_n$, wherein n is 1-10;
B is a moiety selected from H, Fmoc, Cbz, Boc, Mtt, Alloc, a peptide chain, or a linker selected from SMCC, sulfo-SMCC, DSS, Su, Gl, Ad, or a targeting moiety selected from a targeting peptide, protein, antibody, nanobody, aptamer, or small molecule by attachment through one or more amines, sulfides, or carboxylic acids on the targeting group attached to a linker or attached directly to the alpha nitrogen, N, adjacent to B;
C is a moiety selected from OH, OBn, OPMB, $OR_5$, an activated acid, such as an NHS ester, OBT ester, TFP ester, isocyanate and isothiocyanate, a peptide chain, or linker, such as a preformed DSS or SMCC, or a targeting moiety selected from a targeting peptide, protein, antibody, nanobody, aptamer, or small molecule by attachment through one or more amines, sulfides, or carboxylic acids on the targeting group attached to a linker or attached directly to the carbonyl C;
D and D' are independently dyes including NIR and NIRF dyes selected from Cy5.5, Cy7 and other Cy dyes, Alexafluor 680, Alexafluor 750 and other Alexafluor dyes, IR800CW and related NIR dyes, Dylight 680, Dylite 750, Dylite 800 and other Dylite dyes, quencher dyes, and sensitizing dyes; metal-chelate complexes selected from chelating groups DOTA, DTPA, NOTA, TETA, NOTA, TACN, CB-TE2A, Cyclen, DO2A, DO3A, DOT, DOTAM, CB-Cyclam that have been chelated to metals selected from Gd, Eu, Ce, Cu, Tc, Ga, Ge, In, Ho, Tm in their non-radioactive and radioactive forms; or the metal chelate groups selected from these chelating and metal groups conjugated via a linker such as an amide bond, an acetamide bond, or that derived from an activated acid attached to the chelating group via an NHS ester, isocyanate, isothiocyanate, or other activated acid, or chelating groups selected from this group or groups contained within DO3A (DOTAla) and other derivatives of Cyclen;
$R_1$ and $R_1'$ are independently H, $CH_3$, or $CH_2CH_3$;
$R_2$ and $R_2'$ are independently H, $CH_3$, or $CH_2CH_3$;
$R_3$ is H, $CH_3$, or $CH_2CH_3$;
$R_4$ is H, $CH_3$, or $CH_2CH_3$; and
$R_5$ is H, $CH_3$, or $CH_2CH_3$;

Compounds (VI) and (VII) shown below illustrate amino acid modules useful for synthesis of molecular imaging agents. A further description of peptides greater than di-peptides formed from the aforementioned amino acids module and combination of modules follows. Each amino acid module can be composed as follows:

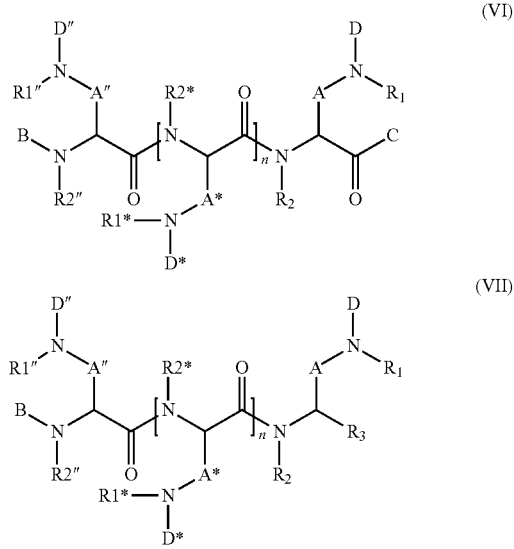

wherein:
$[\ ]_n$ represents a polypeptide chain of variable length;
A, A'' and A* are each independently $(CH_2)_n$, wherein n is 1-10, and A* is a variable designation, for example that is analogous to the series A, A', A'', A''' in the case of a tetra-peptide;
B is a moiety selected from H, Fmoc, Cbz, Boc, Mtt, Alloc, a peptide chain, or a linker selected from SMCC, sulfo-SMCC, DSS, Su, Gl, Ad, or a targeting moiety selected from a targeting peptide, protein, antibody, nanobody, aptamer, or small molecule by attachment through one or more amines, sulfides, or carboxylic acids on the targeting group attached to a linker or attached directly to the alpha nitrogen, N, adjacent to B;
C is a moiety selected from OH, OBn, OPMB, $OR_5$, an activated acid, such as an NHS ester, OBT ester, TFP ester, isocyanate and isothiocyanate, a peptide chain, or linker, such as a preformed DSS or SMCC, or a targeting moiety selected from a targeting peptide, protein, antibody, nanobody, aptamer, or small molecule by attachment through one or more amines, sulfides, or carboxylic acids on the targeting group attached to a linker or attached directly to the carbonyl C; D, D'' and D* are each independently dyes including NIR and NIRF dyes selected from Cy5.5, Cy7 and other Cy dyes, Alexafluor 680, Alexafluor 750 and other Alexafluor dyes, IR800CW and related NIR dyes, Dylight 680, Dylite 750, Dylite 800 and other Dylite dyes, quencher dyes, and sensitizing dyes, metal-chelate complexes selected from the chelating groups DOTA, DTPA, NOTA, TETA, NOTA, TACN, CB-TE2A, Cyclen, DO2A, DO3A, DOT, DOTAM, CB-Cyclam that have been pre-chelated to metals selected from Gd, Eu, Ce, Cu, Tc, Ga, Ge, In, Ho, Tm and other metals in their non-radioactive and radioactive forms; and D* is a variable designation;

$R_1$, $R_1"$ and $R_1*$ are each independently H, $CH_3$, or $CH_2CH_3$; and $R_1*$ is a variable designation;

$R_2$, $R_2"$ and $R_2*$ are each independently H, $CH_3$, or $CH_2CH_3$; and $R_2*$ is a variable designation;

$R_3$ is H, $CH_3$, or $CH_2CH_3$;

$R_4$ is H, $CH_3$, or $CH_2CH_3$; and $R_5$ is H, $CH_3$, or $CH_2CH_3$.

Compound (VIII) represents the general structure of a high-relaxivity agent for MRI where M=Gd or other metal suitable for MRI contrast and where $P_1$ and $P_2$ are acid and amine protecting groups respectively or elaborated peptides or peptide chains. This is a unique ligand metal complex as the N is attached directly to the side chain alpha carbon on Alanine. The novelty and difference from the reported approach (Eszter, et al) is the introduction of the Gd early in the synthesis, prior to incorporation into a peptide chain and in turn, prior to conjugation with a targeting agent or linker-targeting agent system. In this and other cases P1 and P2 can also designate extensions of a peptide chain, or a solid support for peptide synthesis, or a targeting agent, or a linker to any of these including amino acids spacers in a peptide chain.

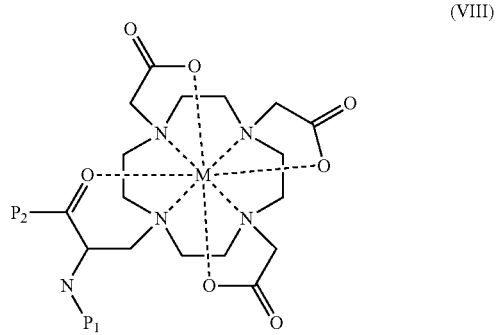

(VIII)

An embodiment includes the use of various metals such as gadolinium (Gd) as a protecting group for DOTA or DTPA in the synthesis of imaging agents for magnetic resonance imaging (MRI). This synthesis allows placement of the metal inside the chelating agent early in the synthesis and thereby allows carrying the metal through the synthesis to avoid the harsh reaction conditions necessary to incorporate the metal later. In addition to the metal functioning as an imaging agent, the metal serves as a "chelate protecting agent" for a wide variety of aforementioned chelating groups.

Other metals include cerium (Ce), europium (Eu) and copper (Cu) and other suitable metals. These metals can be incorporated early in the synthesis and then exchanged in the last step for radioactive metals or mixtures of radioactive and natural isotopes. In some cases, mixtures of radioactive and non-radioactive Cu, In, Tc, are used to provide a suitable dilution of radioactivity and a calculated percentage could be exchanged from mixtures of radioactive and non-radioactive metals of a like or different element in the final step of the synthesis.

The present invention includes methods of incorporating metals early in the synthesis of imaging agents by incorporating metals using pre-formed amino acid side chains. These metals can be utilized directly as imaging agents, such as Gd for MRI, or exchanged for different metals, including radioactive metals for PET or SPECT imaging in the final steps of the synthesis.

By incorporating pre-formed amino acids, such as lysine containing Gd-DOTA, into the peptide early in the synthesis it was found that Gd-DOTA was stable to standard acid, base and hydrogenation conditions for removal of standard protecting groups such as Boc, Mtt, Fmoc, Cbz, and Alloc. This methodology saves numerous steps, reduces the severity of conditions, and greatly simplifies the complexity of side chain manipulations after a peptide having protected side chains is formed. The reduction of complexity in the synthesis increases with increasing number of Gd-DOTA groups introduced in the peptide. Other amino acids containing amine side chains can be utilized as well, including ornithine and B-amino alanine (2,3 amino propionic acid) by introducing Gd into the reported DO3A (DOTAla) in an earlier synthetic step which improves on the reported method by providing all of the advantages described above.

The utility of this concept has been enhanced by developing a simplified purification method. When chelating the four amines and three acid groups in DOTA with a single metal, such as Gd, the resulting compounds, as their single amino acid precursors, or as di- and larger peptides were much more readily purified in standard reverse phase liquid chromatography (LC) and solid phase extraction (SPE) conditions. In the same way that DOTA behaved as a chelate-protecting agent in synthesis, DOTA behaves as a chelate-protecting agent in purification.

The advancement in concept is to synthesize a pre-formed NIR dye containing side chains on amino acids such as readily available lysine residues. The methodology of the present invention creates peptide based imaging agents by assembling pre-formed amino acids containing imaging agents on their side chains in an assembly line type fashion, in a "modular" approach. This brings in the actual imaging agent on the side chain each time a new amino acid is coupled to the peptide backbone, resulting in a completed imaging agent synthesis after the coupling steps. In the case of MRI, as an example, Gd is introduced into a DOTA on the side chain of the amino acid lysine early in the synthesis.

In the case of radioactive metals for PET or SPECT, we allow for incorporation of an easily displaced metal and provide for the radioactive metal by metal exchange or displacement reactions after the peptide based agent is formed. In a further embodiment therefore, a metal exchange occurs in which a metal with suitable kinetic and/or thermodynamic dissociation constant is exchanged by suitable manipulation of pH prior to exchange by a radioactive metal. For example, in the case of a low dissociation constant Ce is displaced by Cu, in mildly acidic medium. Bringing in a more stable oxidation state metal, such as $Eu^{+3}$, followed by reduction to lower oxidation state to $Eu^{2+}$ provides facile exchange with radioactive Cu, In, Tc, Ga and other radioactive metals used in PET and SPECT. This method is designed to enable the last step, exchange to radioactive metal, to occur in a clinical setting or pre-clinical laboratory location where the testing is occurring. This would minimize, transport and would avoid a time delay when handling radioactive imaging agents.

In another embodiment, amino acids containing pre-formed dyes on the side chains are constructed and used as "modules" in peptide coupling reactions. These modules are stable to a variety of deprotection and coupling steps. In some cases the strength of the acid needs to be reduced. For example, some dyes are stable in 20% TFA and this is adequate for deprotection of most acid labile groups such as OtBu esters and Boc groups. In contrast, the t-Butyl groups on DOTA required harsh 100% TFA due to the close proximity of ring nitrogen's to the carboxyl acid site. This further increases the need to remove them early in a synthesis in order to provide for a versatile approach to imaging agents. Side chain dyes were also stable to Fmoc deprotection with a secondary amine, and hydrogenation conditions. The amino acids containing dyes on their side chains can be incorporated into the imaging peptide by standard coupling reagents such as TBTU, HATU, COMU and EDC.

The method of the present invention of assembling a peptide template containing pre-formed amino acids containing imaging groups is applicable to multi-modal agents (i.e., MRI-NIR or MRI-PAI) and agents containing multiple metals (i.e., Multi-Gd agents for MRI). Other examples include two dyes for use in FRET, either as a system for detection, or as an imaging agent, or as a TMIA. It is expected that tri-modal imaging agents would also be available from this method, (i.e., for NIR-MR, PA-MR).

In another aspect, by choosing a combination of metals, one of which exchanges easily (such as Cerium or $Eu^{2+}$) with a metal that is more stable (such as Gd), the modular method can be utilized for incorporation of two different metal groups. Methods include exchange (i.e., from Ce or Eu to a radioactive metal, such as Cu, Ga or Tc for PET or SPECT) and direct insertion (Gd for MRI). Thus, in accordance with the present invention the creation of mixed metal, multi-modal agents by the modular method described to provide molecular imaging agents for PET-MRI or SPECT-MRI and tri-modal agents including NIR-PET-MRI, NIR-SPECT-MRI, PAI-PET-MRI or PAI-SPECT-MRI is provided.

The same approach can be applied to other syntheses of other small molecules in addition to peptides. The present invention includes the concept of bringing in pre-formed imaging agents on side chains or linker chains and coupling them together using standard amine to acid coupling conditions.

This approach also gives the opportunity to assemble and activate the pre-formed imaging portion of a peptide scaffold containing the above systems, and couple or conjugate on a targeting peptide, protein, antibody, nanobody or aptamer, RNA or DNA, or small molecule inhibitor targeting system as the last step, or if a radioactive metal is required, second to last step prior to radioactive metal exchange.

Scheme 4, shown below, is an illustration of a multi-modal TMIA available by this synthetic approach. This portrays an embodiment of assembling modular amino acids containing imaging moieties on their side chains followed by conjugation by a targeting peptide to yield a bi-modal TMIA for MRI-NIR or MRI-PAI. The synthesis is completed right to left as is convention for peptide synthetic approaches with the final conjugation to yield the TMIA also shown. This same approach can be applied to yield mono-modal agents containing one or more metals, such as Gd (multi-Gd), one or more dyes (such as NIR dyes), multi-modal agents (metal-dye), or any combination of these.

Scheme 4 illustrates the modular synthesis of dual modal TMIA as shown below:

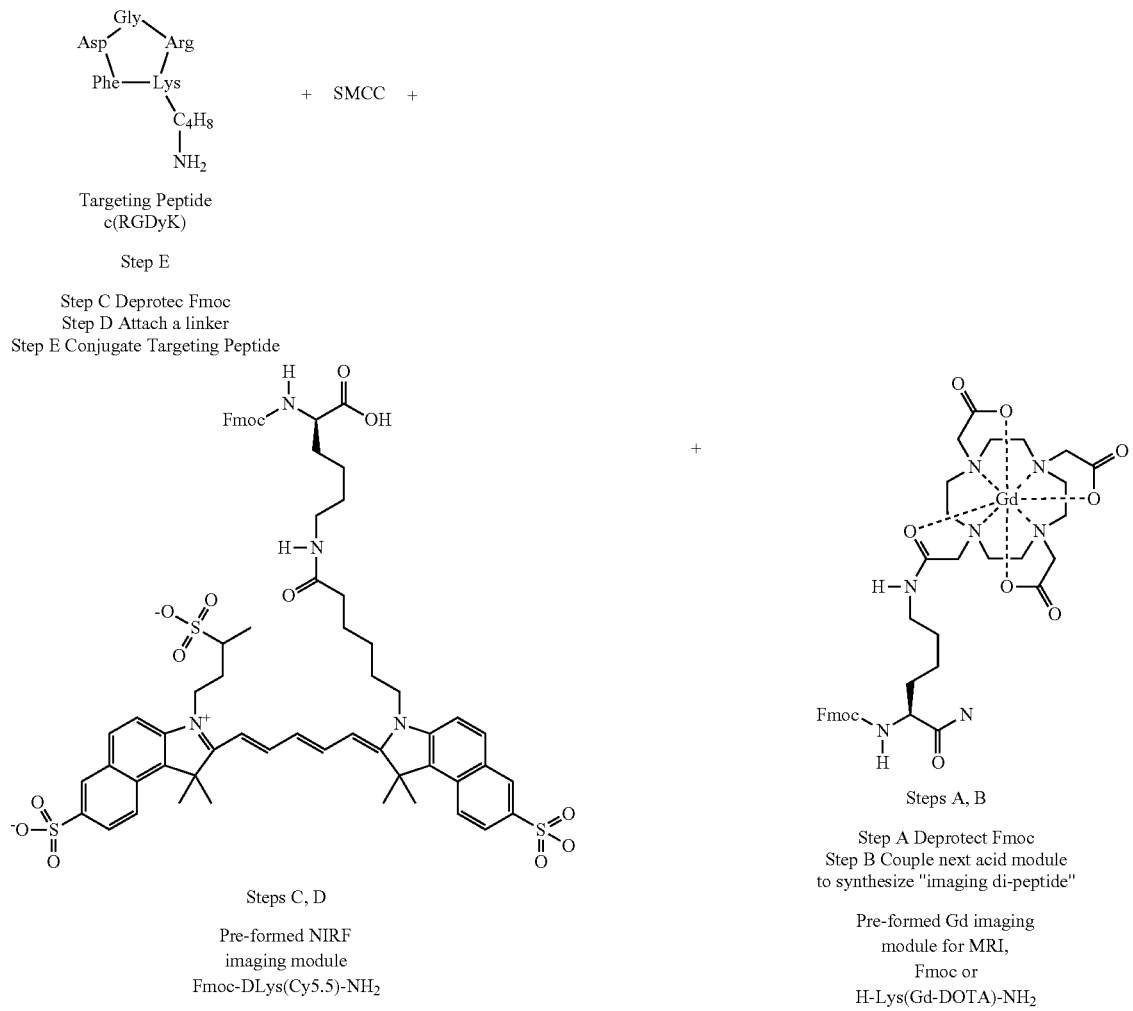

Scheme 5 illustrates the final step in modular synthesis of dual modal TMIA with a documented targeting agent for human A549 cancer cells, c(RGDyK), as shown below:

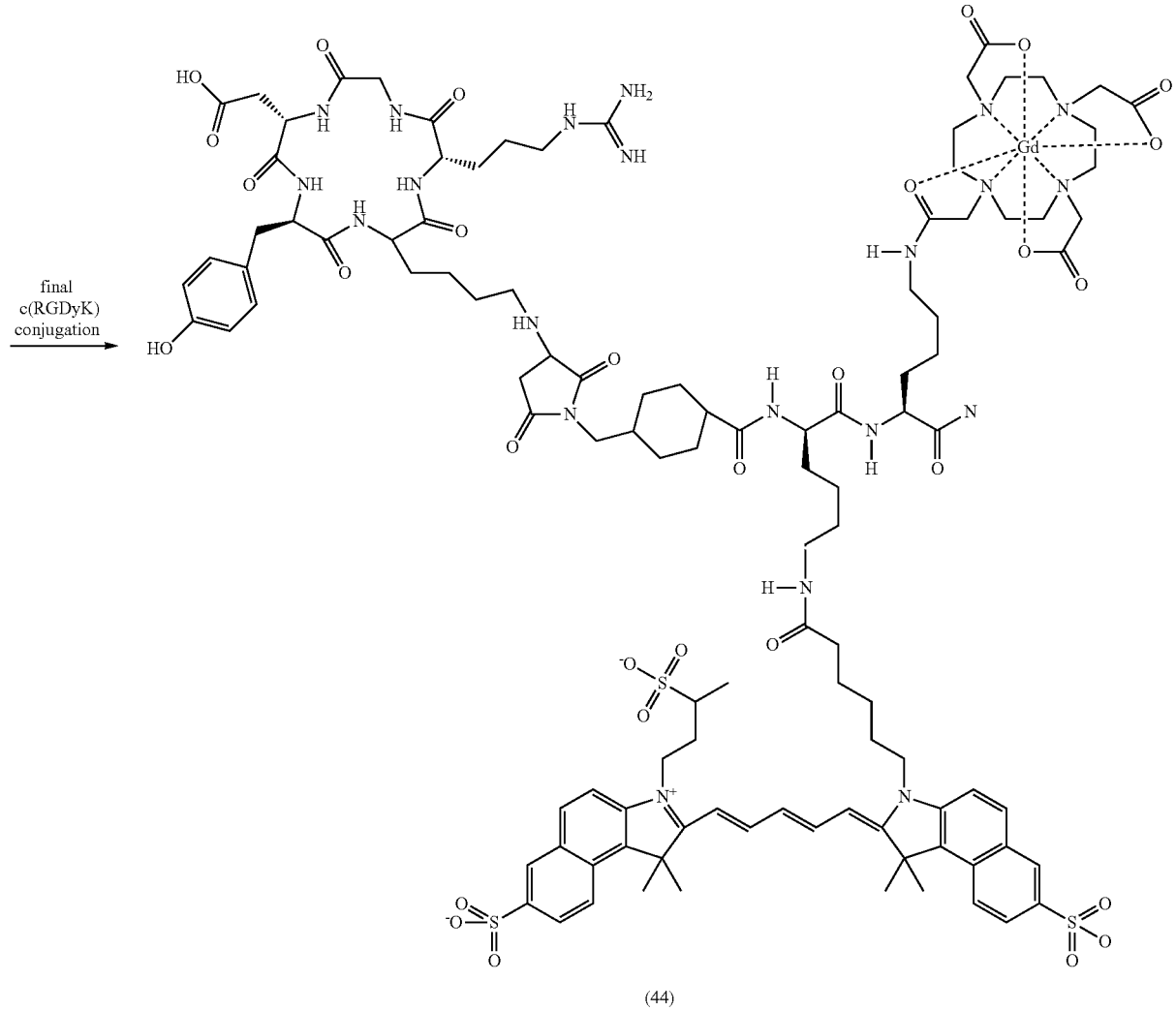

(44)

The methods of the invention enable assembly of non-targeted molecular imaging agents (MIAs) and targeted molecular imaging agents (TMIAs) from pre-formed amino acids containing individual imaging agents on their side chains. The amino acids contain metal-ligand groups tethered through a carbon chain to the backbone of an amino acid. Alternatively, a dye such as a NIR dye can be similarly tethered to an amino acid. These are assembled using peptide coupling methodology to provide peptide-based imaging agents with imaging groups on the side chains.

The chelating group is brought in early in the synthesis as is shown in the examples, followed by incorporation of the metal also early in the synthesis. In one aspect the invention a pre-formed amino containing a chelating group that complexes a metal atom, is separated by a short or long carbon chain to an acid group, or amino group, or in an amino-acid that contains both, and protects that ligand in the elaboration to imaging agents, i.e., a "chelate-protecting agent".

The chain could be made of an amino acid suitable for peptide synthesis where the amine could be protected and the acid free, or the acid protected and the amine free. On the side chain of such an amino acid is a chelating group, for example DOTA or DTPA, containing any metal atom (for example Gd, Cu, Eu) suitable for complexation by the chelating group.

The amino acid containing a metal chelating side chain is designed to be used, and to be useful in, the syntheses of molecular imaging agents for the diagnosis of diseases.

As described further in the examples, both the free amine and the free acid in amino acids and small peptides containing metal chelating agents and NIR dyes on the side chains have been reacted and have shown they behave well in standard peptide coupling reactions. The Gd-DOTA has been shown to be stable to deprotection of Fmoc with a secondary amine stable to hydrogenation conditions to remove Cbz, as an example, and is stable to up to 100% TFA, with side chain NIR dyes stable up to 20% TFA. Other metals are stable for the duration of time to remove Mtt, OtBu, tBoc and other acid-labile protecting groups used in peptide synthesis in acid conditions ranging from 1-100% acids. These conditions are also used to remove solid phase resins from their support, furthering their utility in solid phase peptide synthesis and other similar conditions necessary for organic structural transformations.

A further example includes the use of one or more Gd's on one side chain for MRI, and radioactive metals including Cu, Tc, In and others for PET and SPECT imaging on one or more additional side chains for multi-modal MRI-PET and MRI-SPECT imaging.

A further example includes coupling this first metal containing amino acid to a standard protected amino acid such as Cbz or Mtt which can be further converted to an additional imaging agent, such as a NIR dye on the side chain.

Other examples include the synthesis of modular imaging peptides containing metals or that contain modular amino acids with a NIR dye, such as such as Cy7, Alexa 750, IR800CW, or a lower wavelength dye such as Cy 5.5, Alexa 680, Cy 5, Alexa 650, Texas Red, Oregon Green, Fluorescein and numerous other dyes.

It has been discovered that the amine and acid groups within the chelating sphere unexpectedly remain unreactive in coupling reaction conditions during peptide synthesis and during standard conjugation conditions in the preparation of targeted imaging agents. In addition, they remain stable and unreactive in the aforementioned protection and deprotection reactions that are common to organic synthesis and peptide synthesis. This provides a highly desirable use for them as a method of directly incorporating metals useful in medical imaging agents by the use of standard peptide reactions in solution or solid phase peptide synthesis and standard peptide elaboration conditions. This usefulness extends to their conjugation to targeting agents and agents, such as nanoparticles in the final steps of the synthesis.

By this method a preformed single modal or multi-modal imaging agent may be conjugated to a wide variety of targeting groups in the final step or second last step. In contrast, most TMIA's and peptide based imaging agents reported in the literature have incorporated the targeting group prior to incorporation of all final imaging groups. The latter approach requires individual tailoring of synthetic methods that are compatible with targeting groups. This method is advantageous in providing a means to introduce a wide variety of targeting agents to a preformed imaging agent in the final step or steps.

The compounds drawn in the primary examples are novel and their use in synthesis, including peptide synthesis, standard coupling conditions, and stability in standard deprotection conditions used in both solution and solid phase peptide synthesis is novel.

Gd has been placed on side chains using two procedures. In the first, a three step procedure is used whereby DOTA is incorporated by coupling a commercially available tri-butyl protected DOTA, followed by deprotection, and then followed by chelating Gd. In the second procedure, an unexpected route to the metal protected chelate on side chain can be applied to any primary or secondary amine. It is possible to couple an unprotected DOTA containing four tertiary amines and four carboxylic acids, directly with a coupling reagent such as TBTU, HATU, or COMU. This is done in the presence of Gd in the same step, or with Gd added in a second step to provide the Gd-DOTA reactions from the unprotected DOTA itself and Gd (for example $Gd(OAc)_2$ in one step.

For these methods a way of purifying these compounds has been developed by use of a chromatography method (i.e., preparative SPE) as above, thereby synthesizing the aforementioned useful Gd containing precursors in a multi-step or two step reactions. We have also shown that other metals ($Eu^{2+}$, $Eu^{3+}$, Ce, and Cu) may be used to synthesize the amino acid precursors in this manner and many other metals (Tc, In, Ga) may be likewise incorporated in this manner and that this method could be used to couple or conjugate a wide variety of similar chelating agents including DOTA, DTPA and others.

The shortened synthesis of the precursors described above and this synthesis method combined with simple purification is an additional aspect of the present invention.

Utilizing the pre-formed precursors of steps 1 and 2 shows that linear peptides can be elaborated that may contain multiple side chains or chains containing complexes of metals by the same standard coupling or conjugation processes. An example is shown in which a Di-Gd complex is prepared. A second example is shown whereby a multi-modal agent containing a NIR dye for fluorescence imaging or photoacoustic imaging can be prepared.

It is possible to use this modular method to couple amino acids, such as lysines containing multiple metal atoms, or multiple dyes, in any number and in any combination limited only by solubility in solution, solid phase peptide synthesis methods, or other coupling methods. It is likewise possible to conjugate virtually any amine, sulfur or acid containing targeting group such as a peptide, protein, antibody, aptamer or small molecule to this imaging peptide.

In a variant of the modular method, the introduction of a second amino acid with standard protecting groups such as Mtt and Cbz coupled to an amino acid module containing a chelated metal method, followed by conversion of that Mtt or Cbz protecting group to a NIR dye is provided. Thus, is it is possible to use the metal "chelate-protecting agent" to elaborate with non-functionalized amino acid with non-functionalized chains or amino acids in conventional peptide chains as well.

The examples further illustrate metal chelates such as Ce-DOTA, or Eu-DOTA on amino acid side chains or as modular precursors to other metals including radioactive Tc, In, Ga, Cu by metal exchange reactions.

By this method amino acids could also contain targeting peptides, proteins, antibodies, nanobodies, and aptamers bonded to the side chain of amino acids and that these resulting pre-formed targeting amino acids could also be assembled in an "assembly line" like fashion. By analogy, this would be coupling together pre-formed modules to create a template based single, double, or triple (multi-modal) targeted molecular imaging agent (TMIA) with each amino acid in the final peptide containing an imaging agent or a targeting agent.

The modular approach includes coupling together pre-formed amino acids containing imaging groups placed on the side chain. Examples of this are shown below. In general, it is favorable to synthesize and couple together the pre-formed agents so that the targeting groups can come in as the last step. In this manner, pre-formed single or multi-modal agents can be pre-made then attached to a variety of peptides, proteins, antibodies, nanobodies, aptamers, small molecules or other targeting agents containing a nucleophilic amine (N atom), sulfide (S atom), or a electrophilic form of a carboxylic acid in the final step, avoiding the necessity of performing further chemistry with the targeting groups present. An exception is metal exchange for radioactive metals which could occur in the last step to avoid use of a radiochemical prior to transport to the location where testing occurs.

The invention will be further illustrated with reference to the following specific examples. It is understood that these examples are given by way of illustration and are not meant to limit the disclosure or the claims to follow.

EXAMPLES

Example 1

This Example illustrates the synthesis of amino acid metal-ligand modules, Compounds (1)-(5). In this synthesis an Fmoc-protected lysine is used to form the amide form and Fmoc protected and free alpha amine forms of the amino acid metal-ligand modules where "b" refers to product of the second step. Amino acids are L form, unless otherwise donated with D. A terminal caboxamide is employed in solution phase synthesis to emulate an extended peptide or solid support resin.

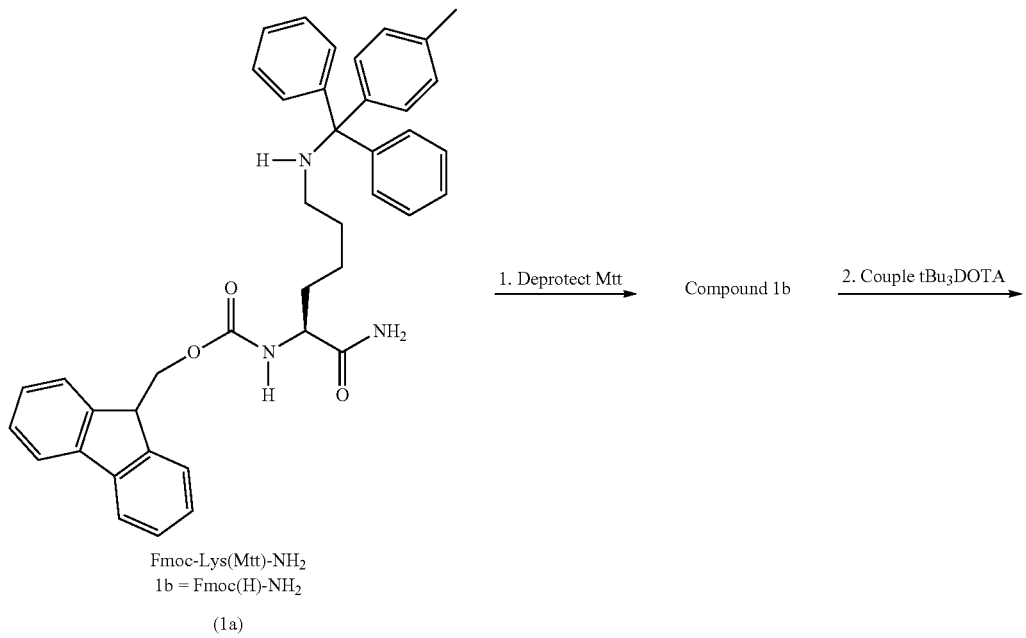

Fmoc-Lys(Mtt)-NH$_2$
1b = Fmoc(H)-NH$_2$ (1a)

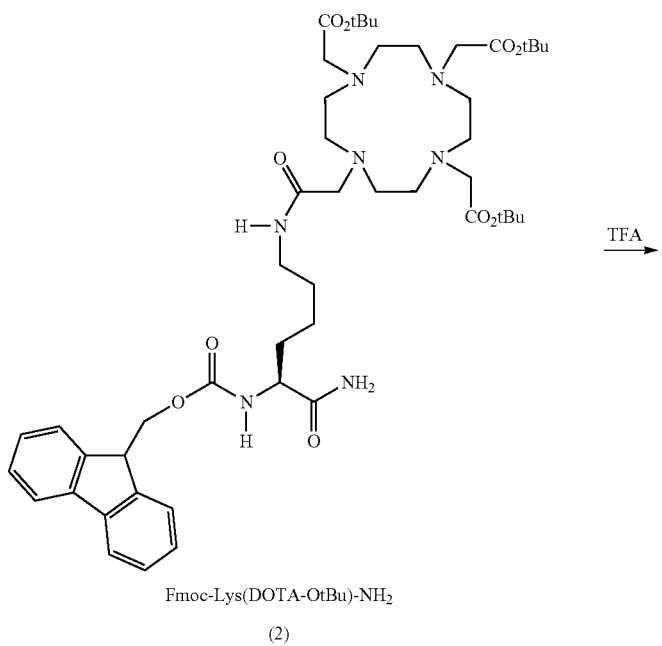

Fmoc-Lys(DOTA-OtBu)-NH$_2$ (2)

-continued
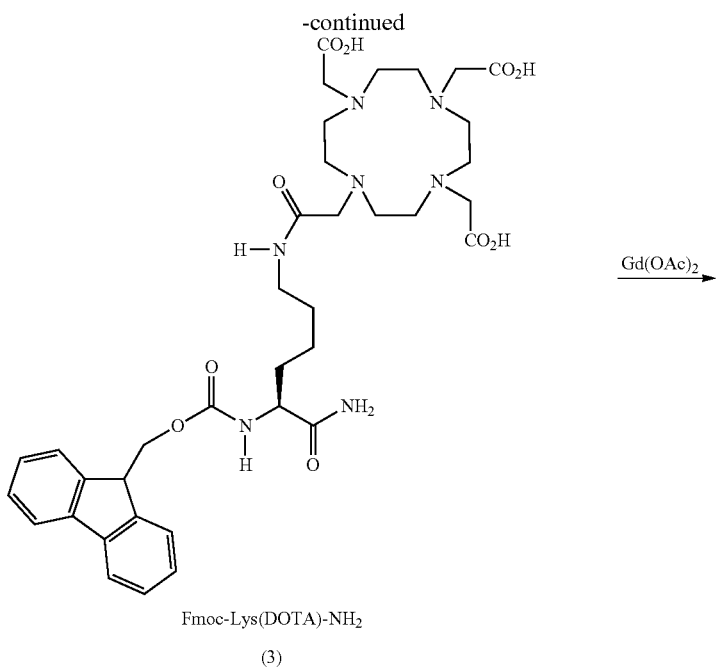
Fmoc-Lys(DOTA)-NH$_2$
(3)
Gd(OAc)$_2$
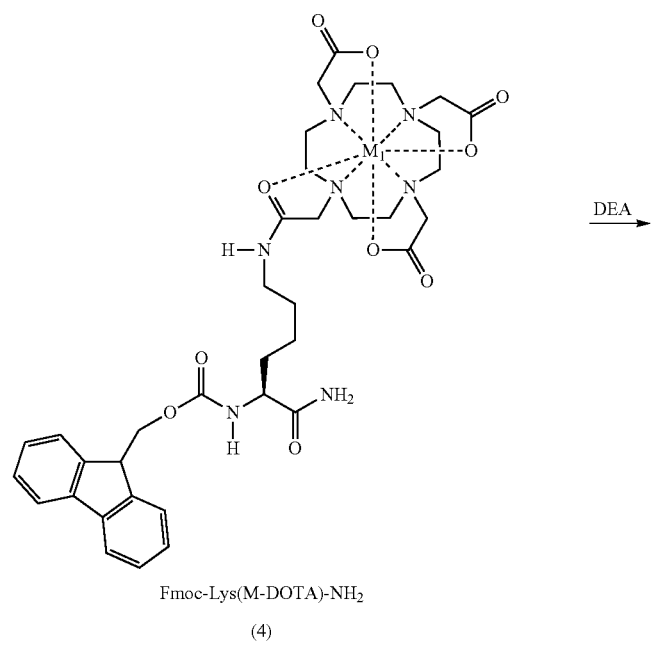
Fmoc-Lys(M-DOTA)-NH$_2$
(4)
DEA

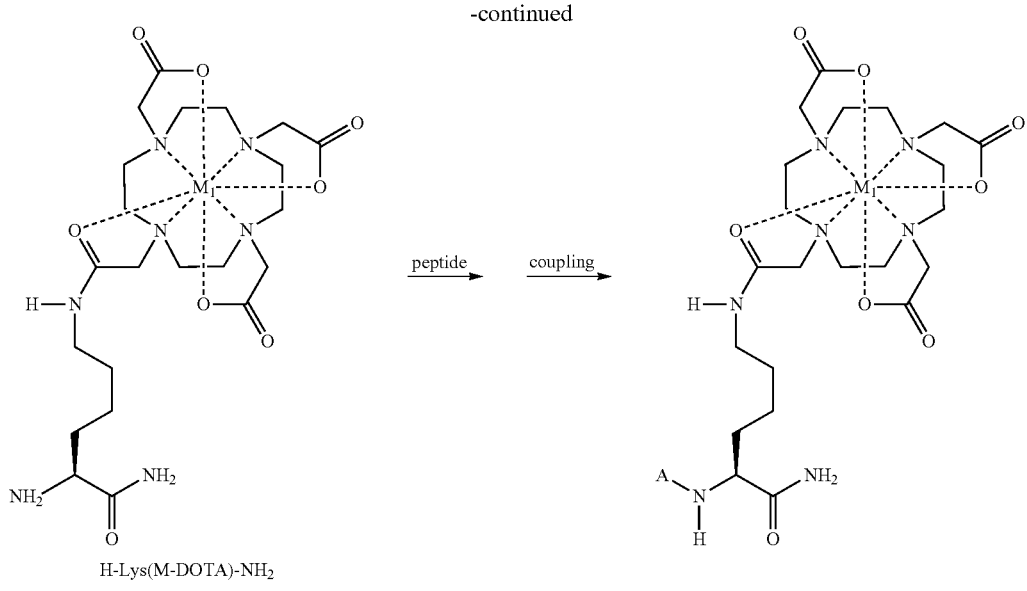

H-Lys(M-DOTA)-NH₂
(5)

wherein:

M₁ is Gd in Compounds (4)-(5); and

A is elongated peptide chain, or linker, or targeting agent, or linker to targeting agent.

In this case "A" above could denote a peptide, a peptide containing additional imaging agents by the modular method described, or Compound (5) could be conjugated directly or via a linker to any targeting agent (i.e., a peptide, protein, antibody, nanobody, imaging group, linker, assembly of targeting groups and/or imaging agents or biomarker or larger assembly, such as a dendrimers, polymers, or nanoparticles).

Example 2

This Example illustrates the synthesis of amino acid metal-ligand modules, Compounds (6)-(8). In this synthesis an Fmoc-protected lysine is used to form free acid and activated acid forms of the amino acid metal-ligand modules.

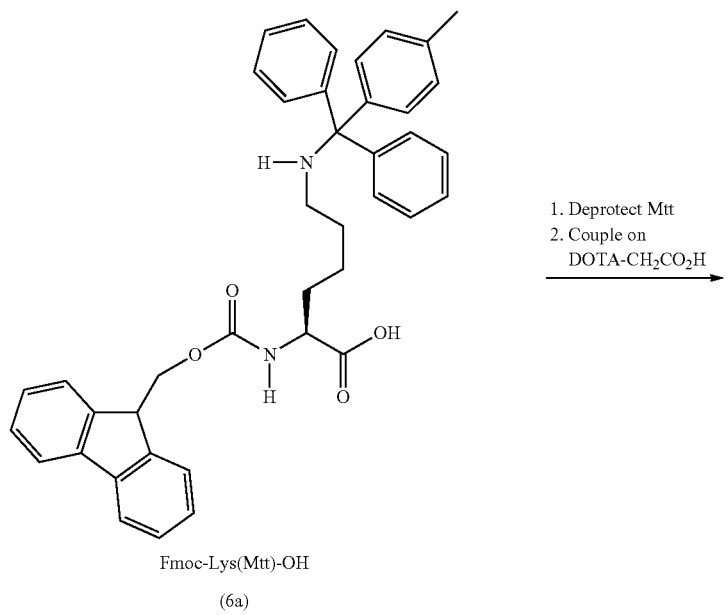

Fmoc-Lys(Mtt)-OH
(6a)

-continued
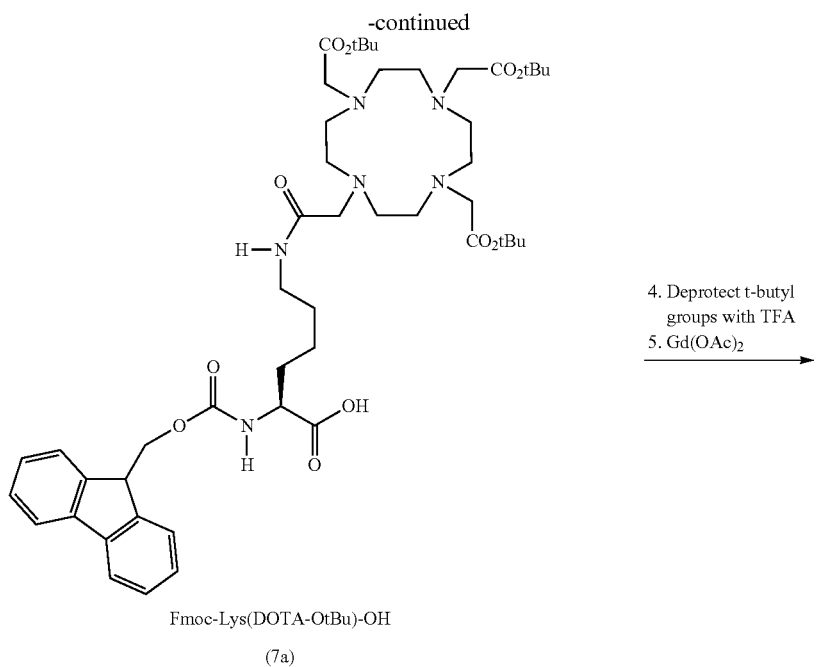
Fmoc-Lys(DOTA-OtBu)-OH
(7a)
4. Deprotect t-butyl groups with TFA
5. Gd(OAc)₂
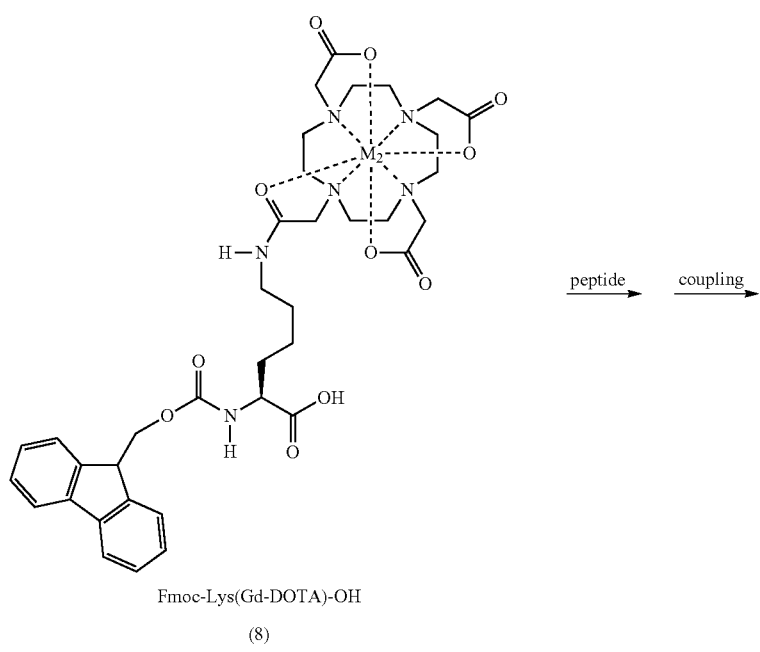
Fmoc-Lys(Gd-DOTA)-OH
(8)
peptide coupling -continued

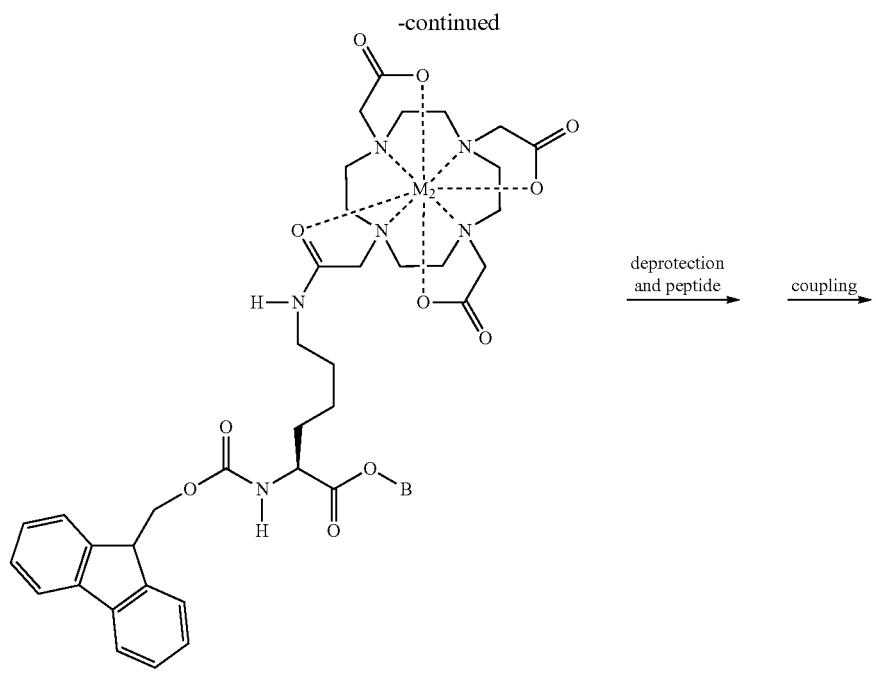

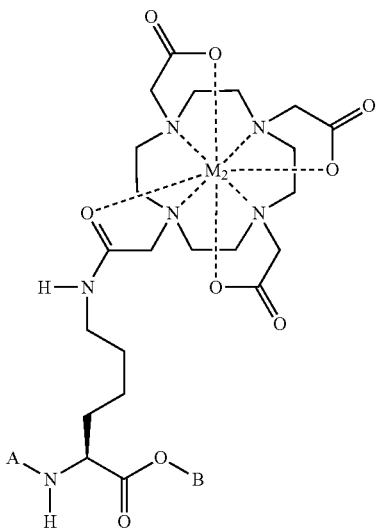

wherein:

M₂ is Gd in Compound (8).

A, B=In this case A and B above could denote a solid support, elongated peptide chain, linker, targeting agent, or linker to targeting agent, a peptide containing additional imaging agents by the modular method described, or Compound (8) could be deprotected and conjugated directly or via a linker to any targeting agent (peptide, protein, antibody, nanobody, imaging group, linker, assembly of targeting groups and/or imaging agents, biomarker, larger assembly such as a dendrimers, polymers, or nanoparticles).

Example 3

This Example illustrates one step synthesis of amino acid metal-ligand modules, Compound (8). The butyl protected precursor is expensive, so a "one-pot" reaction with both the side-chain deprotected lysine acid and the backbone terminal carboxamide (not shown) is proposed as a less expensive method.

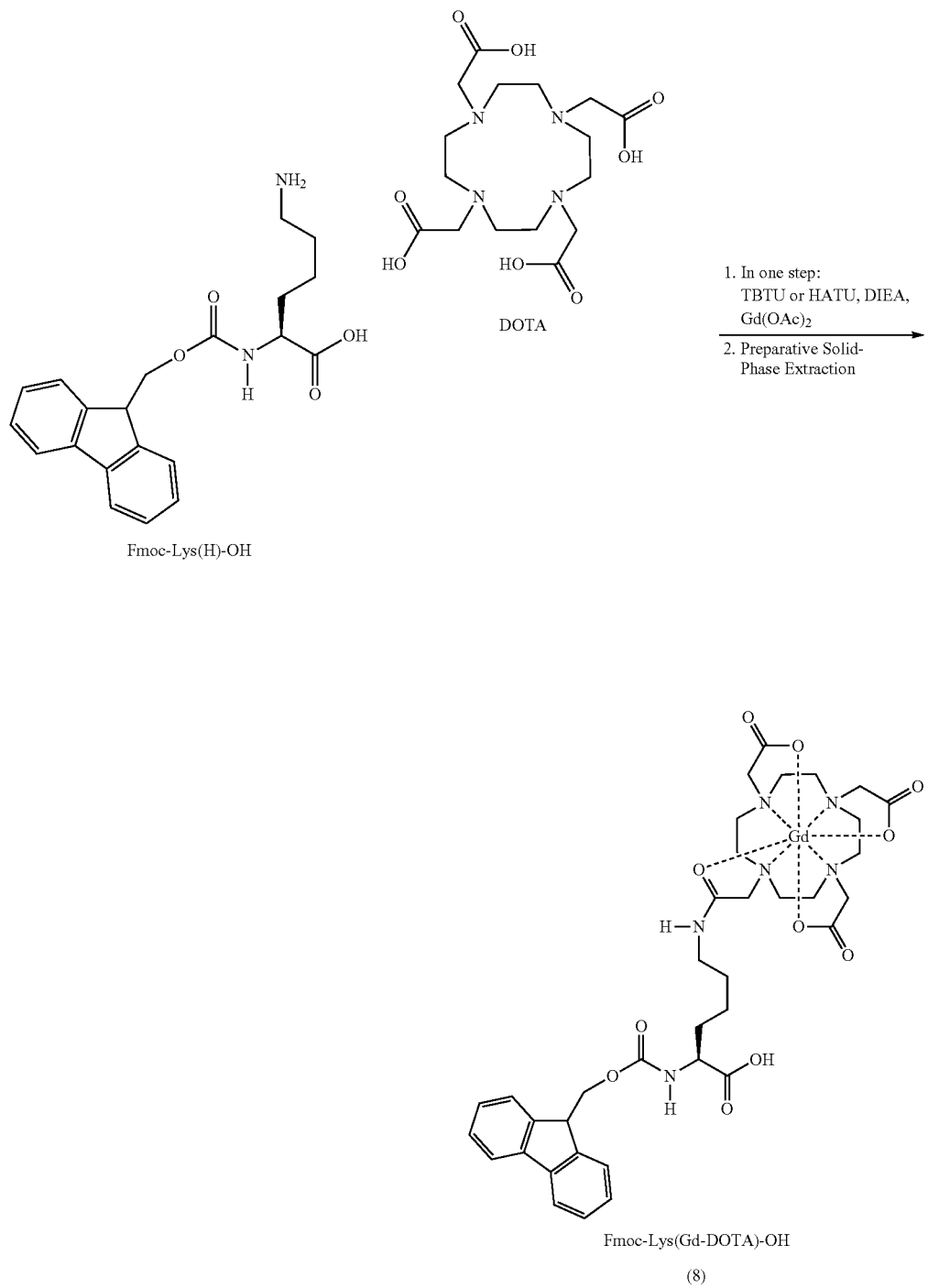

The product was formed, albeit in less than optimal yield. However, in consideration of multiple steps and the cost of the t-butyl precursor this method was utilized for synthesis of precursors. The purification by SPE or HPLC was somewhat easier in the case of the acid Compound (8) versus the amide Compound (5).

Example 4

This Example illustrates the synthesis of amino acid metal-ligand modules, Compounds (9)-(12).

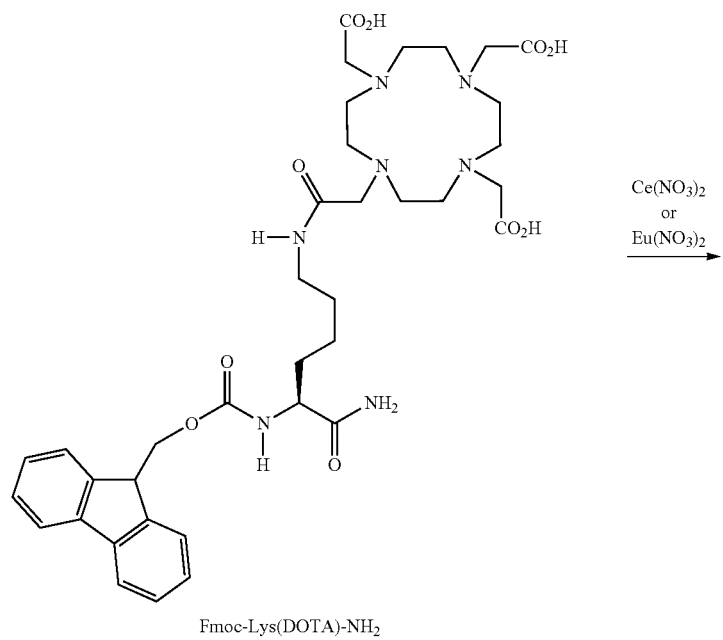
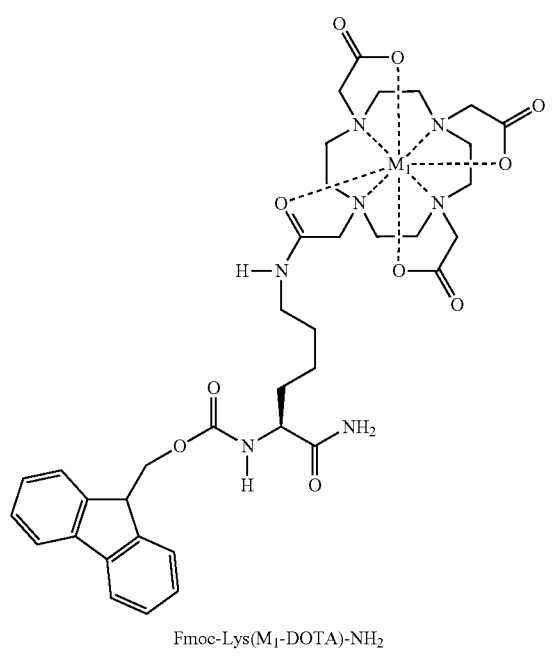

wherein:
M₁ is $Eu^{3+}$ in Compound (9), $Eu^{2+}$ in Compound (10), Ce in Compound (11), and Cu in Compound (12).

Compounds (9)-(12) can be prepared by the three step procedure in Example 1 or by the one step procedure in Example 3. A method of exchanging radioactive metals for PET from non-radioactive metals with weak dissociation constants with those of somewhat stronger dissociation constants is also provided. To model the exchange of metals in the final steps of the synthesis of a TMIA, metal analogs of Compound (5) were prepared. The objective was to use "cold" (non-radioactive) metals as test cases for radioactive metals as the chelating activity would surely be identical. Exchange was possible utilizing Cerium and Europium in the +2 oxidation state, made by the same two methods for synthesizing Compound (5).

Example 5

This Example illustrates the metal exchange in solution and in SPE cartridge of Compounds (11), (12).

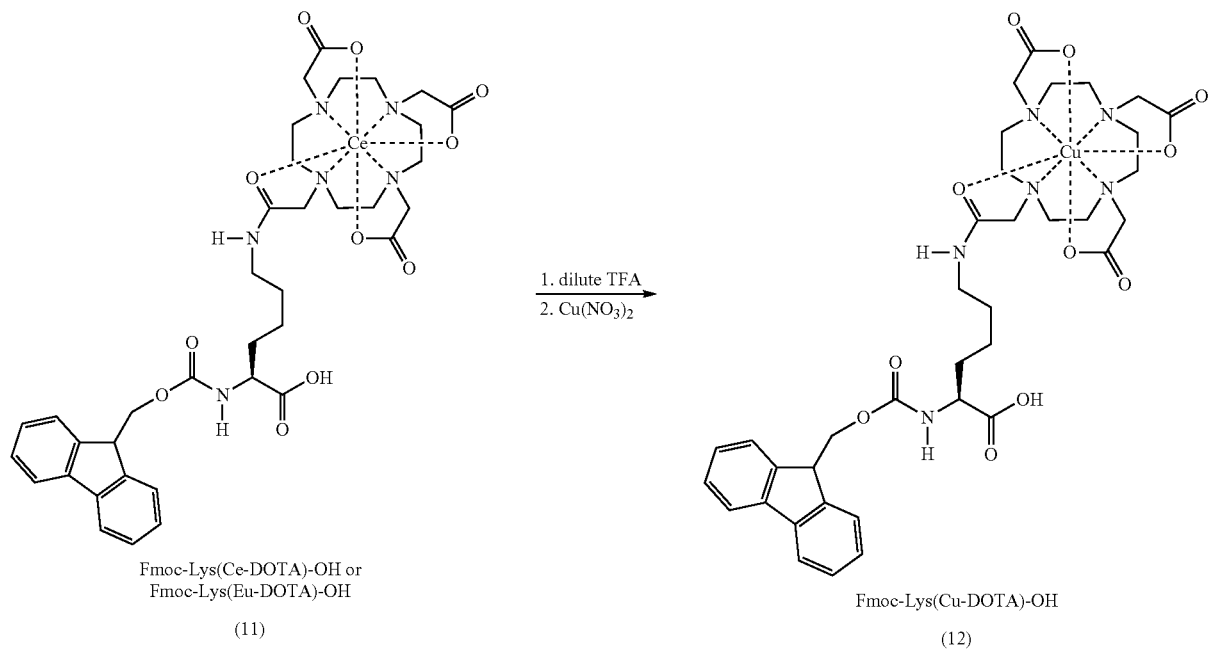

The exchange above may be carried out by a solution technique involving mild acidification followed by either exchange of metal or followed by loading onto a preparative SPE cartridge, eluting with a solution of the desired metal followed by elution from the column with an appropriate solvent.

Example 6

This Example illustrates the synthesis of amino acid-dye modules, Compounds (13)-(18). In this synthesis Fmoc-protected lysine's where used to form the basis of amino acid-NIR dye modules. For our purpose various alternative sulfonated forms of the well-known Cy5.5 and Cy7 were available. Related NIR and NIRF dyes as delineated above such as IR800CW could also be provided as side chains in modular amino acids as follows.

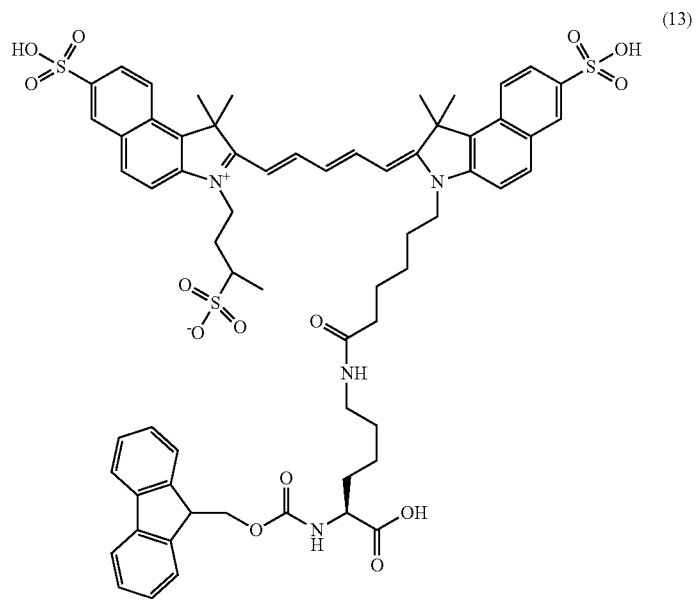
Fmoc-Lys(Cy5.5)-OH = (13a)
Fmoc-DLys(Cy5.5)-OH = (13b)
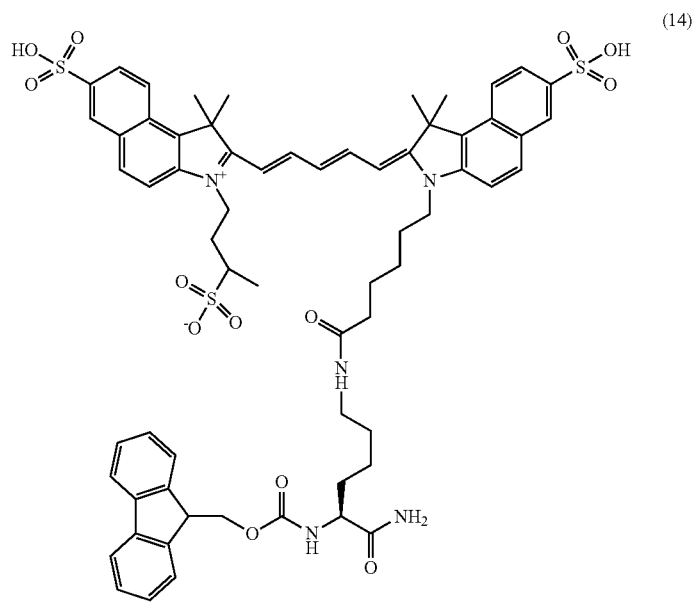
Fmoc-Lys(Cy5.5)-NH2 = (14)
H-Lys(Cy5.5)-NH2 = (15)

-continued
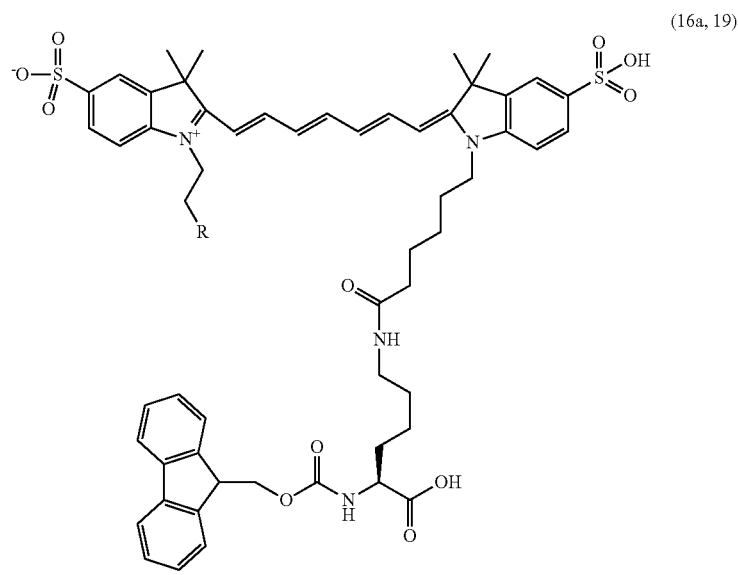
Fmoc-Lys(Cy7)-OH, R = SO₃H (16a)
Fmoc-DLys(Cy7)-OH, R = SO₃H (16b)
Fmoc-Lys(Cy7)-OHm R = H (19
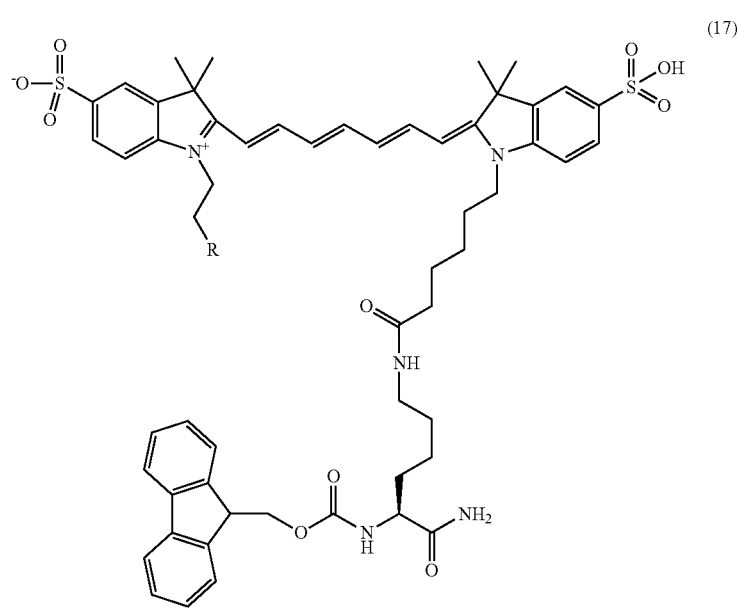
Fmoc-Lys(Cy7)-NH₂, R = SO₃H (17)
H-Lys(Cy7)-NH₂, R = SO₃H (18)

Example 7

This Example illustrates the synthesis of generic forms of modular dye amino acids, as shown below.

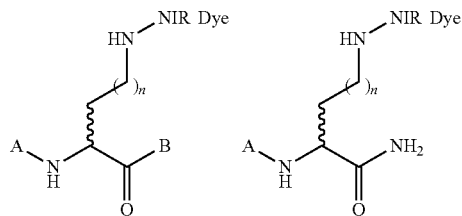

The amino-acid dye modules could be represented broadly by these two examples. As in the prior examples, the peptide could be elongated as in A and B described where these could denote a peptide, a peptide containing additional imaging agents by the modular method described. Backbone protecting groups could be deprotected and conjugated directly or via a linker to any targeting agent (peptide, protein, antibody, nanobody, imaging group, linker, assembly of targeting groups and/or imaging agents or biomarker or larger assembly such as a dendrimers, polymers or nanoparticles.

Example 8

This Example illustrates the synthesis of high relaxivity MRI amino acid modules, Compounds (20)-(26).

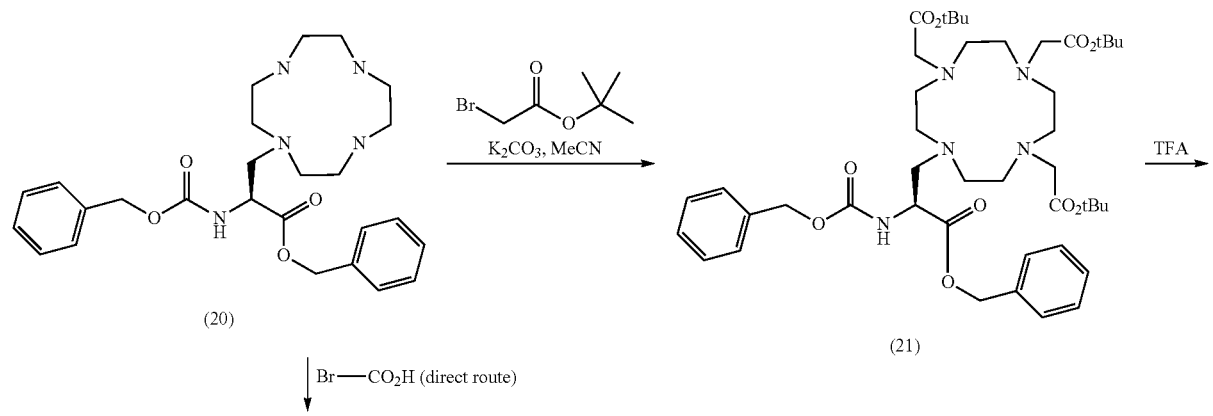

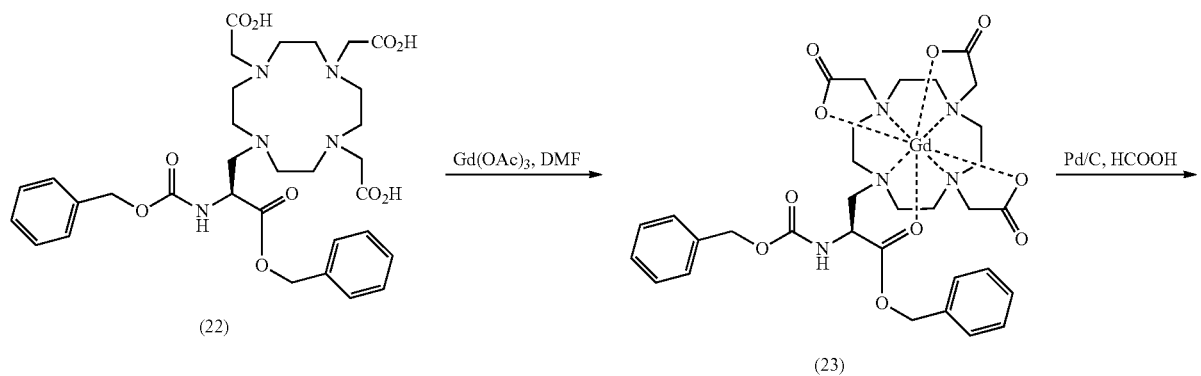

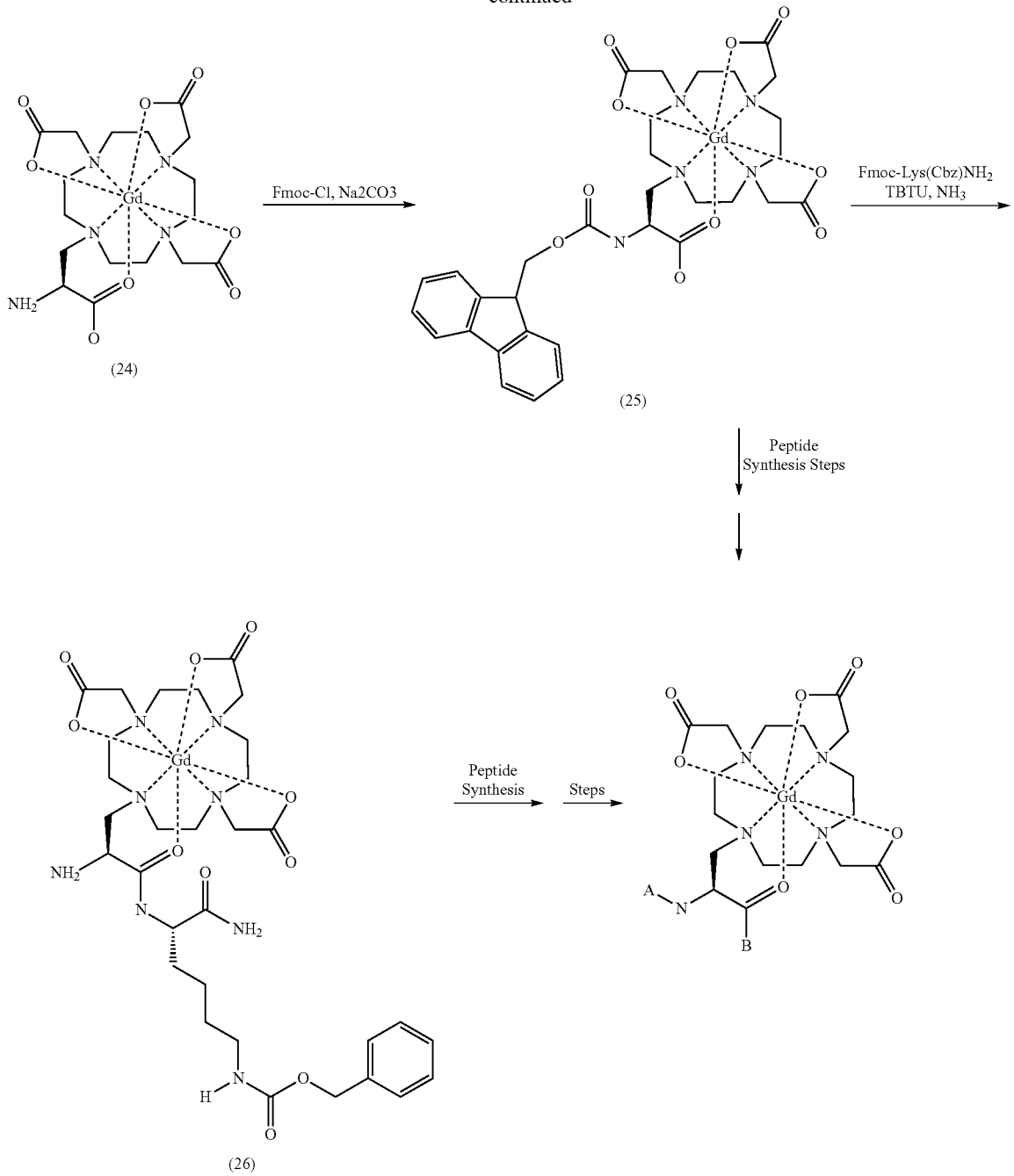

In this synthesis, the application of the metal chelate-protecting agent, in which the Gd is introduced early, is shown in a synthesis of high-relaxivity MRI agents containing "DOTAla" (or DO3A)". The high relaxivity agents containing DOTala (or DO3A) offers an improved T1 relaxation time in MRI which results in greater MRI contrast (Sherry, et al, Ferreira, et al).

The method enables the preparation of high-relaxivity agents for MRI from pre-formed modules of the type shown above in Compounds (23)-(25). This has been coupled to a second protected amino acid and thus illustrates peptide chain elaboration as designated by A and B (peptide chains, or other imaging agent amino acids or peptides, or targeting agents or linkers to targeting agents. In addition, the approach would be applicable to the attachment of additional Gd-DO3A (DOTAla) residues coupling them together in a peptide synthesis approach.

As in most peptide syntheses using Gd, the method reported in the literature utilizes tri-butyl groups on DOTA during peptide incorporation and elongation steps. These are deprotected with harsh acid and Gd introduced in the final steps, a non-ideal method that is incompatible with many targeting groups and precludes many alternative imaging groups such as NIR dyes in the same molecule as NIR dyes are not stable in strong acid. By introducing Gd early by the availability of (25) these difficulties are avoided.

By introducing the Gd early in an analogous manner as the prior introduction into the lysine side chain, a vastly improved, synthesis of agents for MRI is offered that would be applicable to a wide variety of peptide based imaging agents, including agents available by incorporation of (25) or the deprotected amine after Fmoc removal in peptide synthesis. The coupling of the acid (25) has been shown to proceed well to produce (26).

The amino acids containing metal-chelate complexes can be brought into a solution or solid phase peptide synthesis in the initial steps of the synthesis of a TMIA via the following examples.

Example 9

This Example illustrates the synthesis of di-Gd contrast agent with SMCC linker, Compounds (27)-(29).

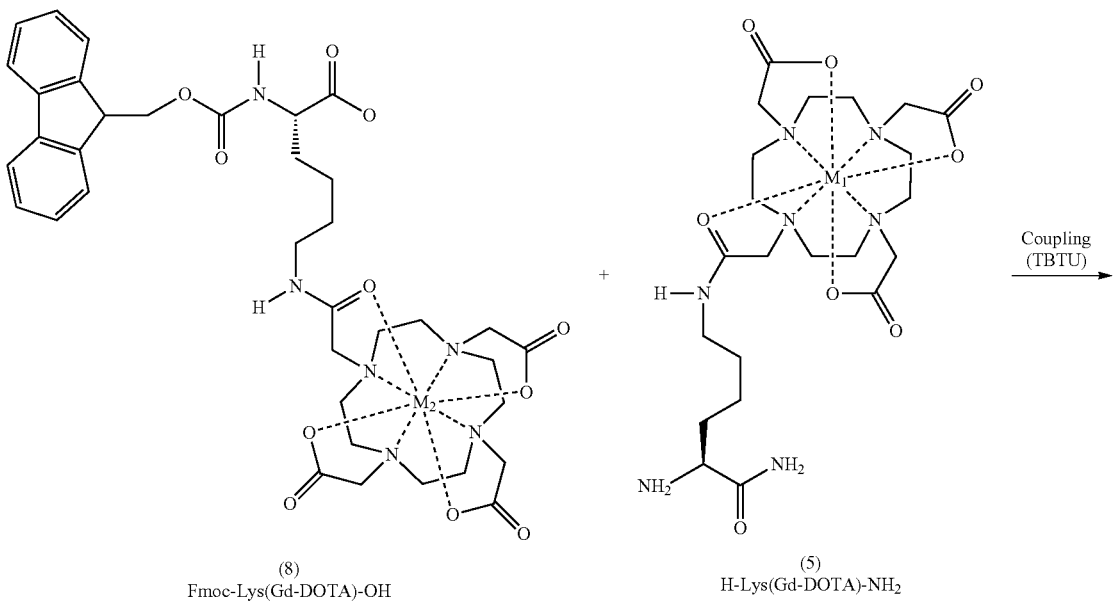

(8)
Fmoc-Lys(Gd-DOTA)-OH (5)
H-Lys(Gd-DOTA)-NH$_2$

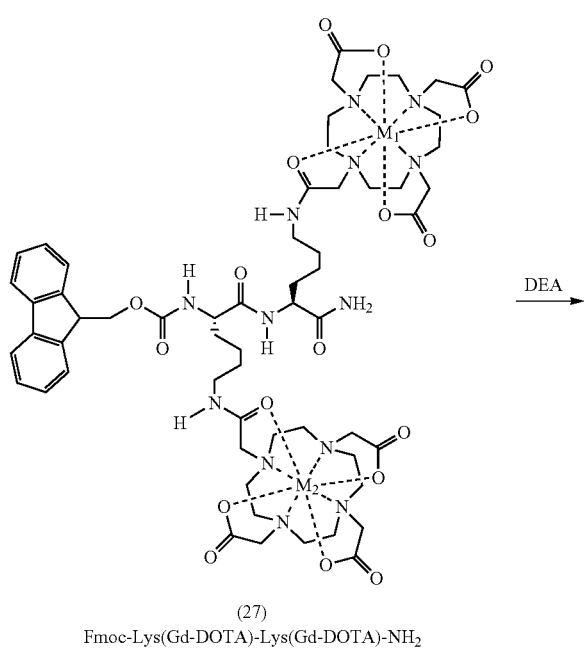

(27)
Fmoc-Lys(Gd-DOTA)-Lys(Gd-DOTA)-NH$_2$ 45    46
-continued
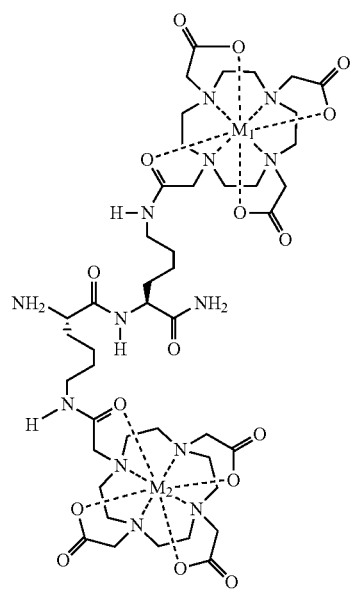
(28)
H-Lys(Gd-DOTA)-Lys(Gd-DOTA)-NH₂
SMCC →
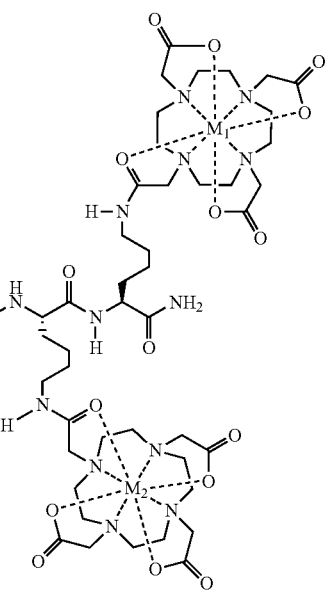
(29)
SMCC-Lys(Gd-DOTA)-Lys(Gd-DOTA)-NH₂
wherein $M_1$ and $M_2$ are each Gd in Compounds (27)-(29). Compound 29 was then conjugated via the attached SMCC linker as follows:
Compound 29 —c(RGDyK)→
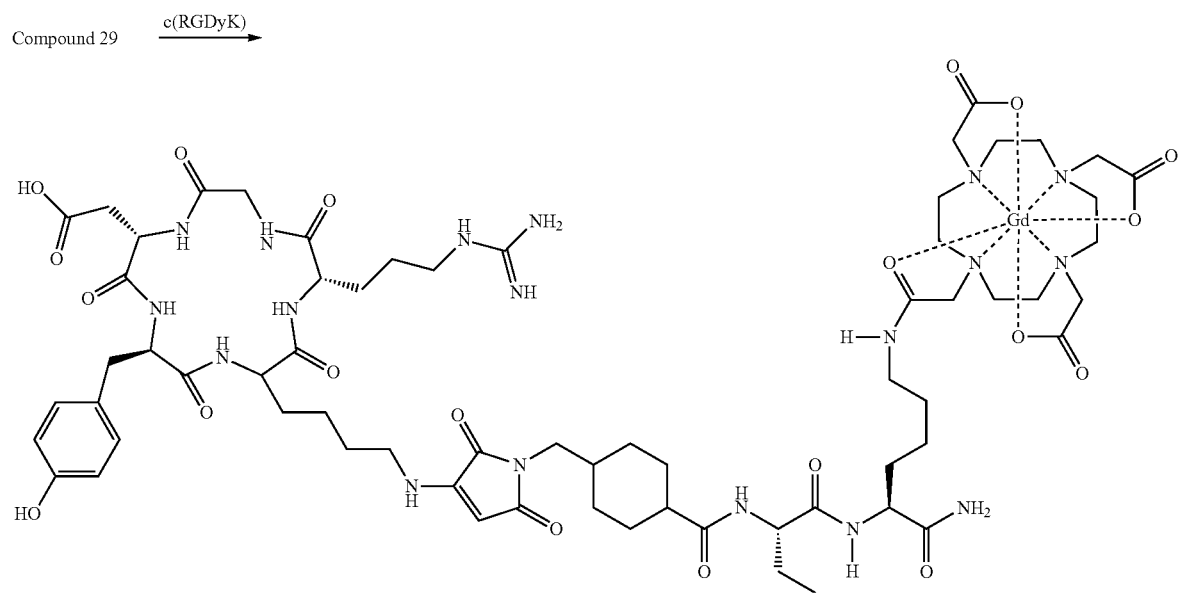

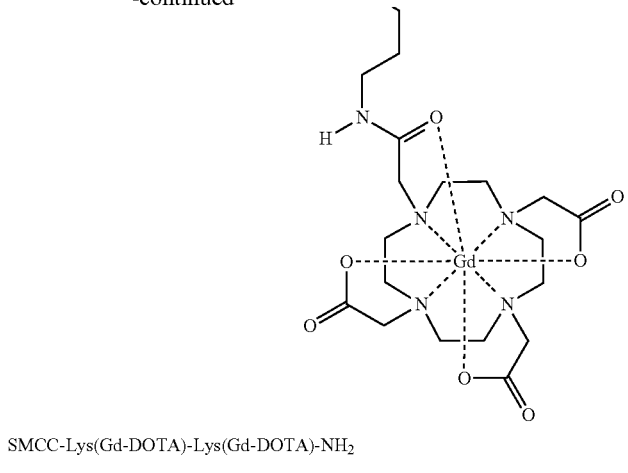

SMCC-Lys(Gd-DOTA)-Lys(Gd-DOTA)-NH₂

(30)

The compounds above provide a second method of providing increased contrast in MRI by placement of multiple Gd atoms in an imaging agent is shown by the synthesis of a di-Gd image contrast agent. Two lysine amino acid residues, each containing a Gd-DOTA (chelated metal) have been incorporated on the side chain. In one case the amine is free and the acid is elaborated into a terminal carboxamide. This also serves to emulate an extended peptide chain and a solid support in solid phase synthesis. In the second module the same Gd-DOTA side chain is utilized, but in this case the amine is protected as a standard Fmoc group and the acid is left free to react.

As noted above, the Gd-DOTA moiety is shown to be stable to peptide deprotection conditions including by base, acid and hydrogenation and is stable to peptide coupling conditions. The synthesis is a straightforward approach to Di-Gd agents and differs with existing di-Gd syntheses in that the Gd is introduced early in the synthesis by introduction into the initial precursors or modules. This method is also applicable for continued elaboration to provide tri, tetra and other multi-Gd agents utilizing the same methodology.

To demonstrate the versatility and stability of the side-chain metal chelating complex (Gd-DOTA) the deprotected H-Lys(Gd-DOTA)-NH2 was conjugated to Fmoc-Lys(Cbz)-OH and to Fmoc-Lys(Mtt)-OH in standard peptide coupling reactions. This showed stability to removal of Fmoc by DEA, to coupling conditions (TBTU or HATU in DIPA or DIEA), to hydrogenation conditions to remove the Cbz group, as well as stability to 20% TFA conditions to remove the Mtt protecting group.

Amino acid-metal module and Cbz or Mtt protected Lysine were coupled followed by deprotection and conjugation to NIR dye. This shows that lysine containing a pre-formed metal complex can be coupled to an acid, and it is stable to deprotection of the side chain Cbz by hydrogenation and of Mtt by acid (TFA) hydrolysis. This shows that Gd also behaves as a chelating protecting agent for the tetra-acetic acids, such as in DOTA and DTPA disallowing their coupling in favor of coupling to the acid desired.

Example 10

This Example illustrates the synthesis of imaging dipeptide by Method A, Compounds (31)-(34).

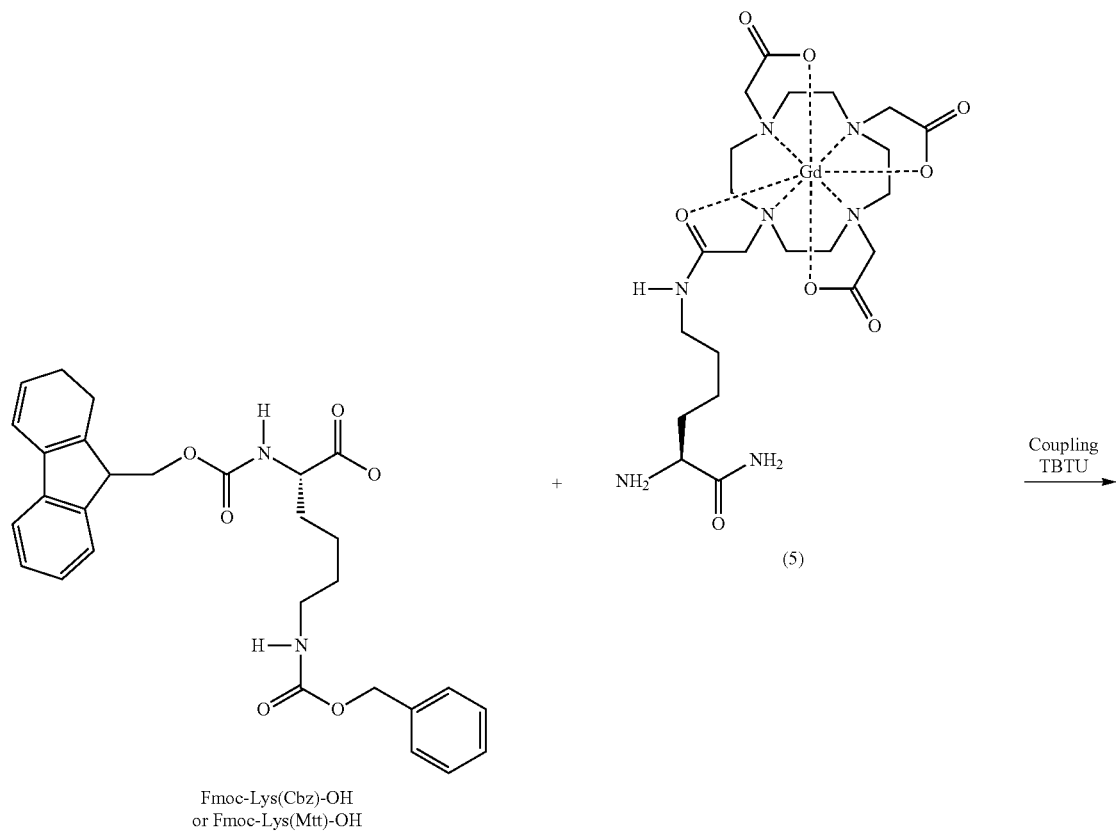
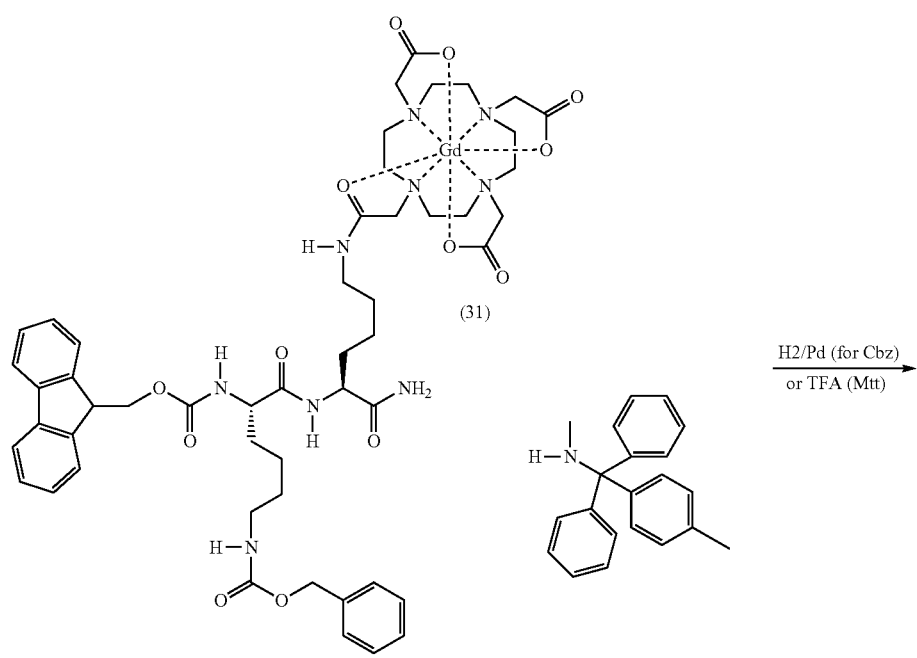

-continued
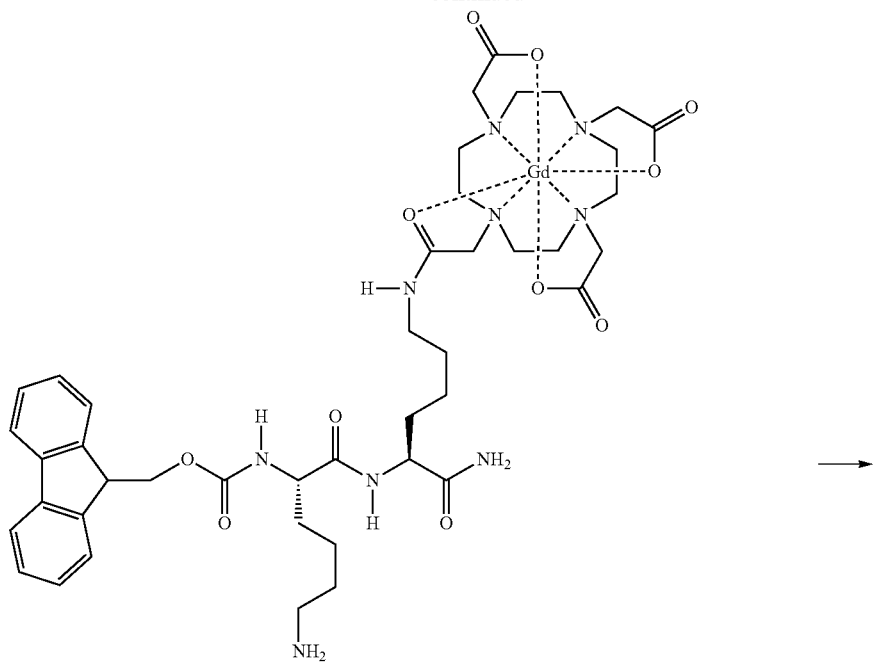
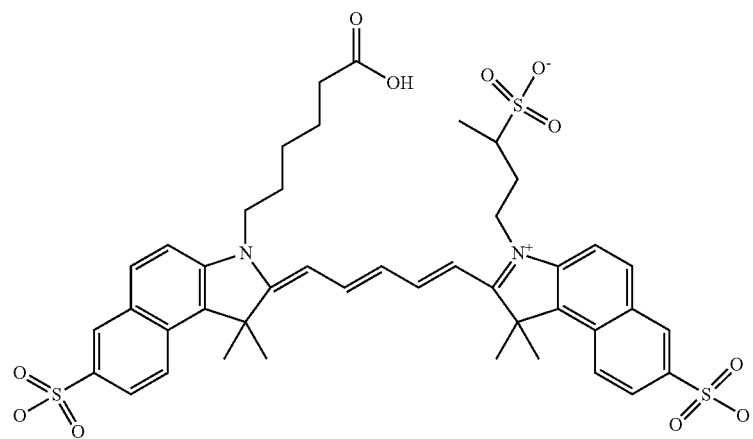
Cy 5.5 (activated)

-continued

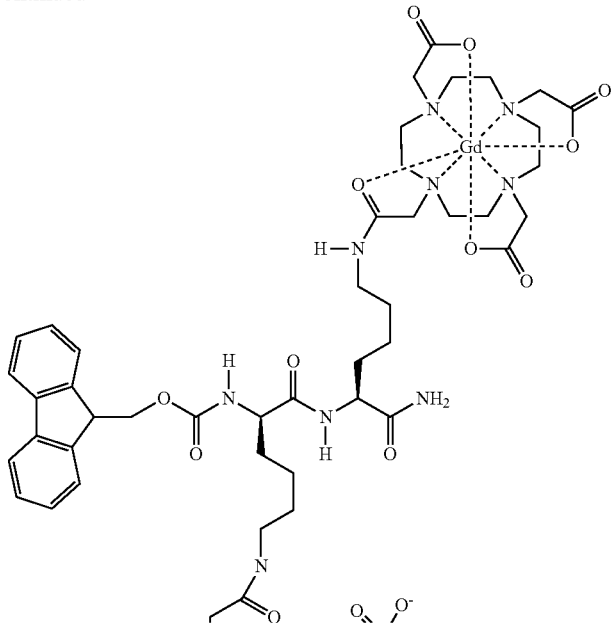

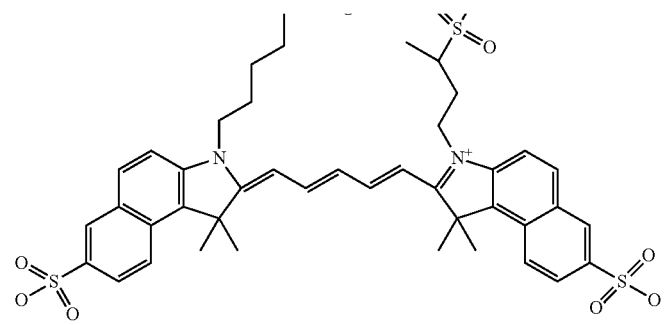

Fmoc-DLys(Cy5.5)-Lys(Gd-DOTA)NH2

(34) D isomer

In the inverse sequence of the above coupling step, the versatility of the amino acid modules was demonstrated by coupling the acid of the Fmoc-Lys(Gd-DOTA)-OH to an amine of the right hand amino acid, in this case H-Lys(Cbz)-NH2. As in the prior example, this shows that the Gd behaves as a protecting group and that a pre-formed metal complex can be coupled to for further elaboration of the imaging peptide.

Example 11

This Example illustrates an alternative approach to imaging di-peptides, Compound (35).

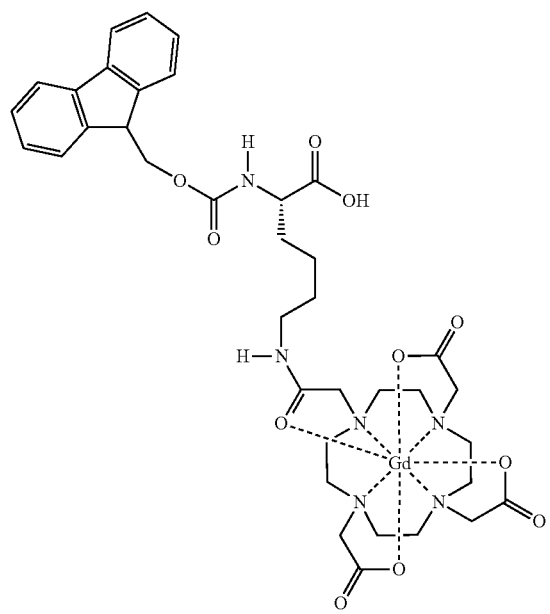
(8)
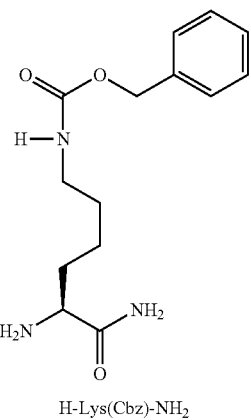
H-Lys(Cbz)-NH$_2$
1. TBTU or HATU DIEA in DMF →
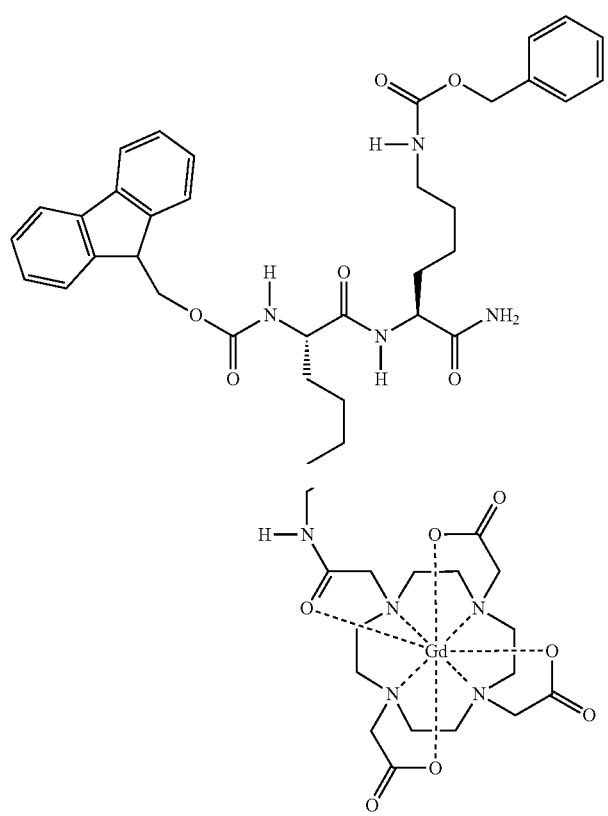
Fmoc-Lys(Gd-DOTA)-Lys(Cbz)-NH$_2$
(35)
2. Deprotrection of Cbz with H$_2$/Pd →
Compound 35b: Fmoc-Lys(Gd-DOTA)-Lys(H)-NH$_2$ By coupling an amino-acid—dye module (Compound (IV)-(V)) with an amino acid—metal-Ligand Module (Scheme 3) a fully modular synthesis of multi-modal imaging agents is available. The result was an Fmoc protected dipeptide containing a Gd-DOTA chelate and a NIR dye as shown. The terminal carboxamide is an emulation of a further peptide chain or solid phase support. This agent is designed for subsequent conversion to final TMIAs by removal of final Fmoc protecting group, attaching a linker, following by attaching a targeting agent as shown in following sections.

Example 12

This Example illustrates the modular synthesis of a multi-modal agent, Compounds (34), (36).

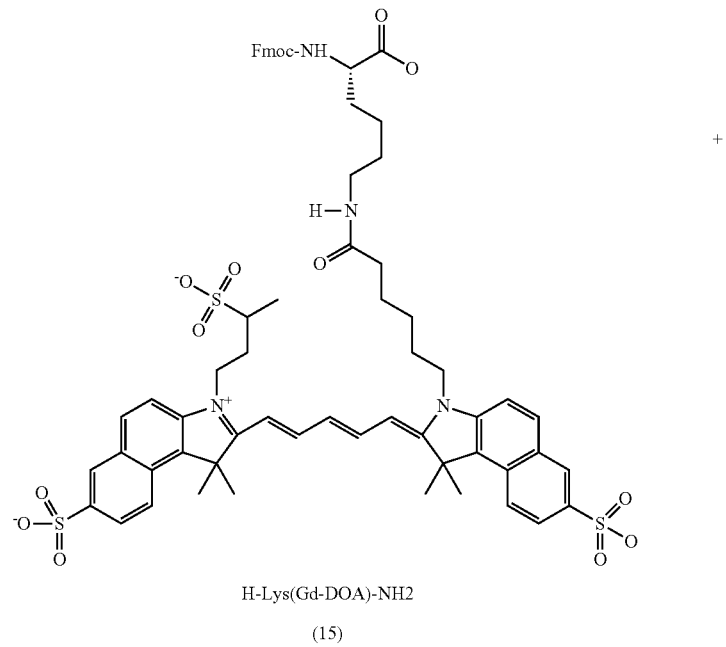

H-Lys(Gd-DOA)-NH2

(15)

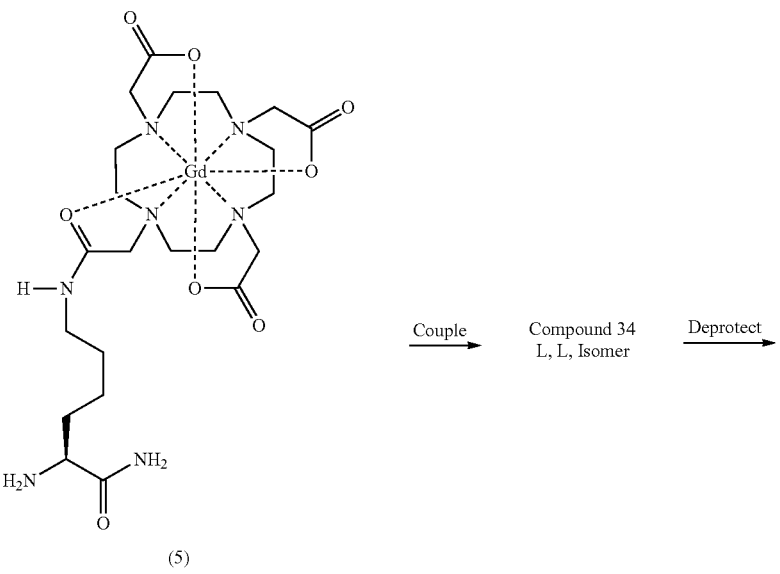

(5)

-continued
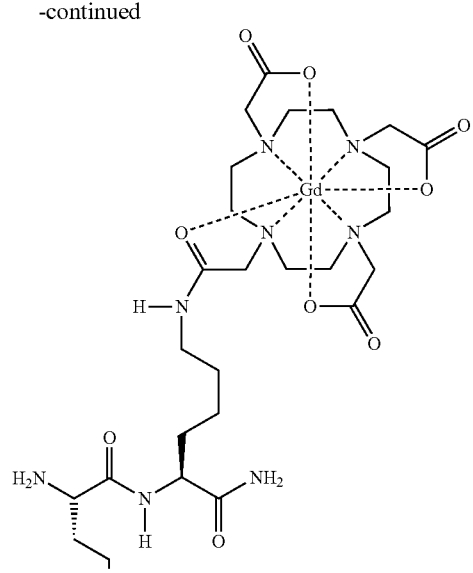
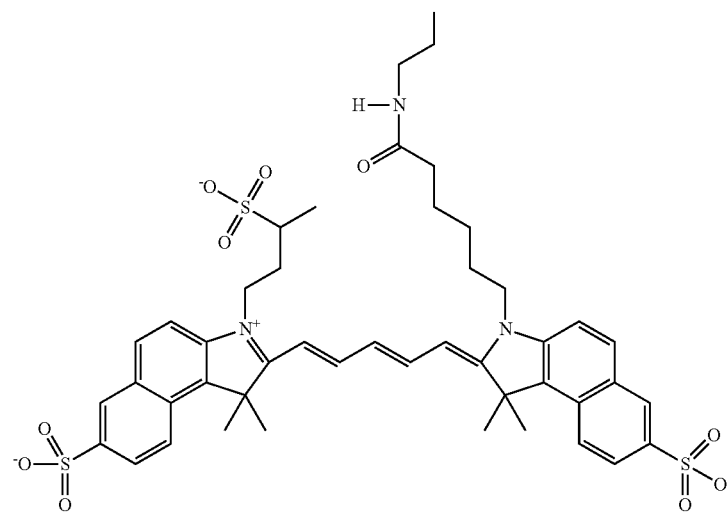
(36)

An initial application of the modular approach to TMIA's is the design and synthesis of single-modal agents. These examples below show two linkers which were successful in preparation of the final TMIAs establishing that linker chemistry is viable. These were then applied to dual modal agents in subsequent examples.

Example 13

This Example illustrates the synthesis of single modal agent c(RGDyK) Gd agent for MRI using succinate linker, Compounds (37), (38):

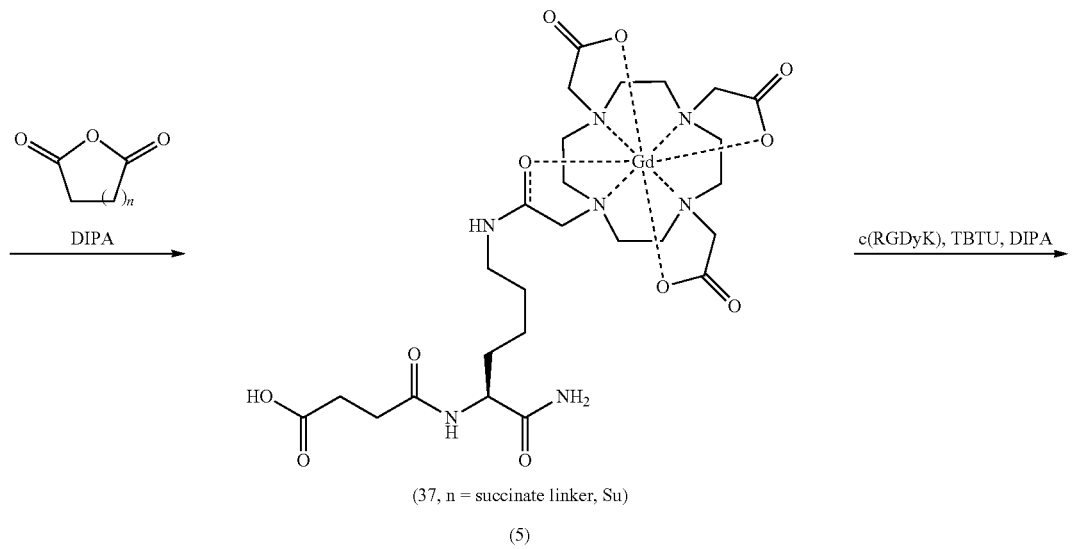

(37, n = succinate linker, Su)

(5)

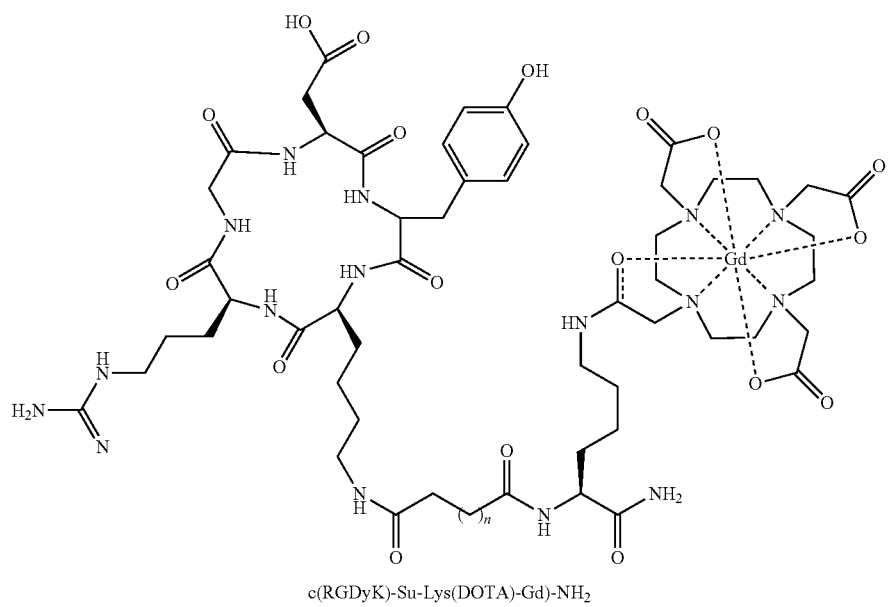

c(RGDyK)-Su-Lys(DOTA)-Gd-NH$_2$ (38, n = 1, Su)

Example 14
This Example illustrates the synthesis of single modal agent c(RGDyK) Gd agent for MRI using an SMCC linker, Compounds (39), (40).
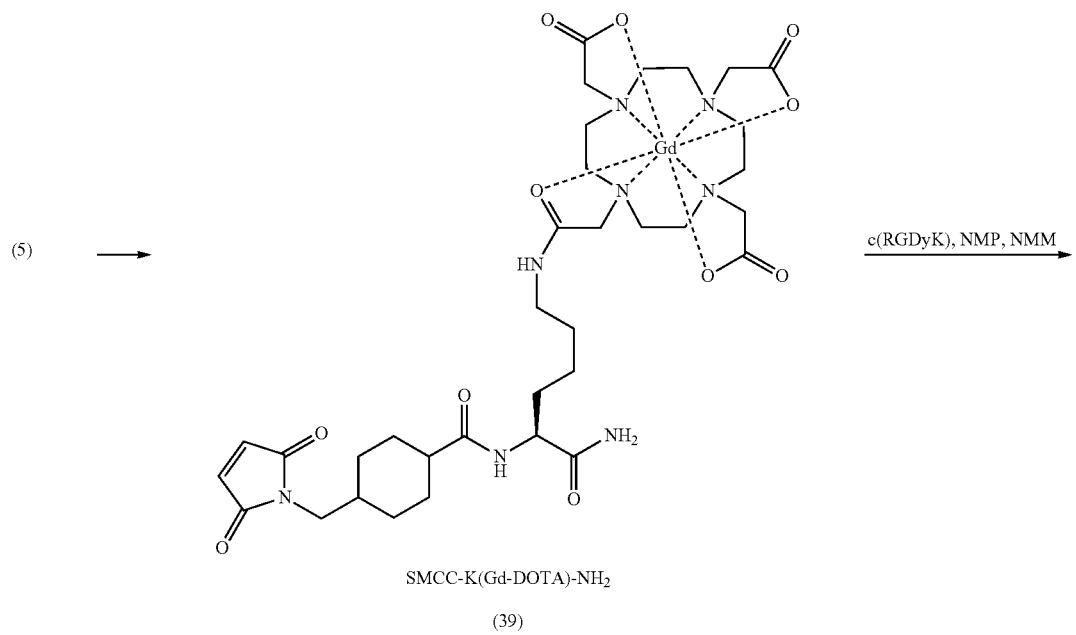
SMCC-K(Gd-DOTA)-NH₂
(39)
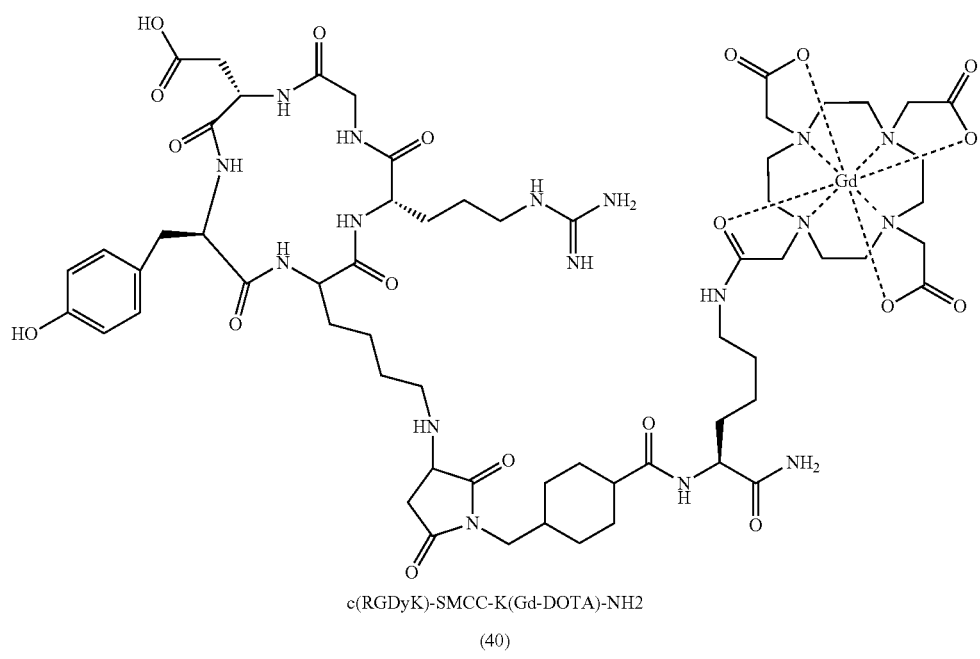
c(RGDyK)-SMCC-K(Gd-DOTA)-NH2
(40)

The following Examples 14 and 15 provide the final TMIA in which there is a NIR for use in NIR or PAI imaging and a Gd for use in MRI. The peptide RGDyK was chosen since methods were developed for evaluation of binding to human A549 lung cancer cells by confocal fluorescence microscopy (CFM).

Example 14

This Example illustrates synthesis of bi-modal TMIA, RGDyK-SMCC-K(Cy5.5)-K(Gd-DOTA)-NH2 by modular method, Compounds (41), (42).

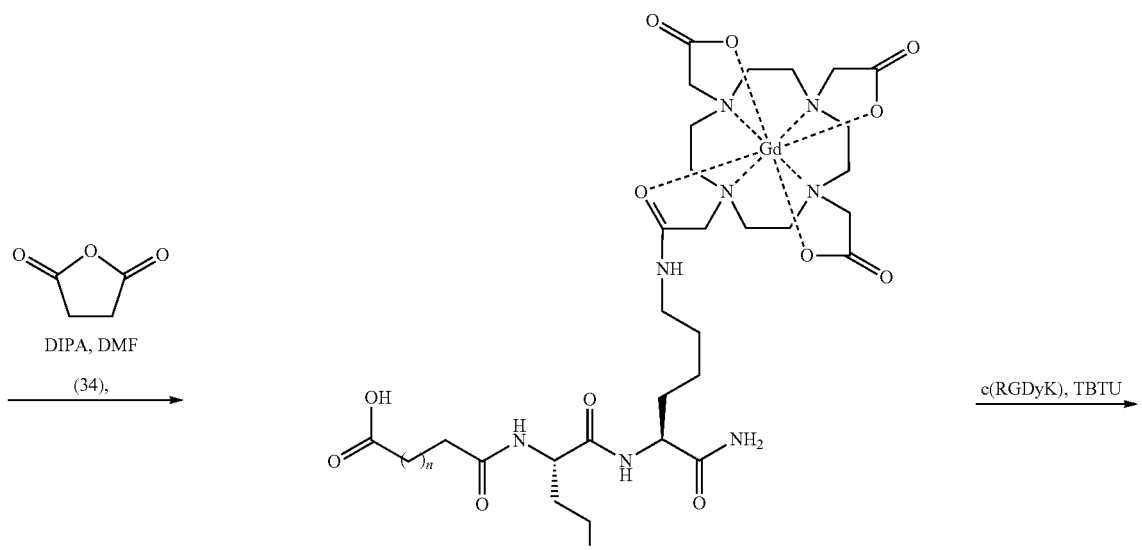

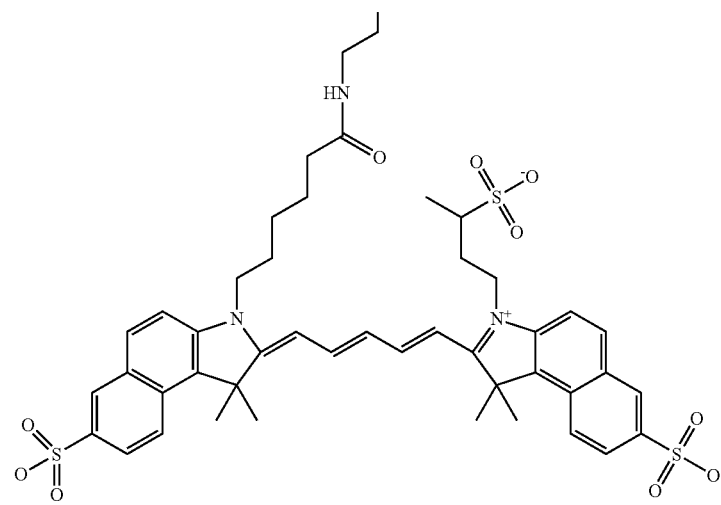

Su-Lys(Cy 5.5)-Lys(Gd-DOTA)-NH₂

(41)

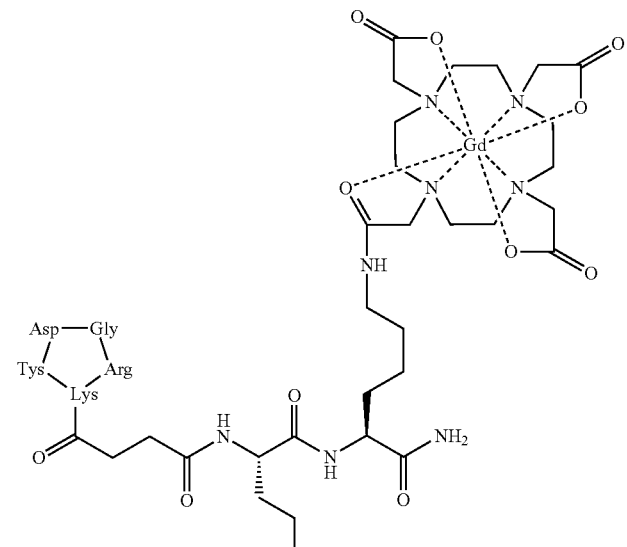
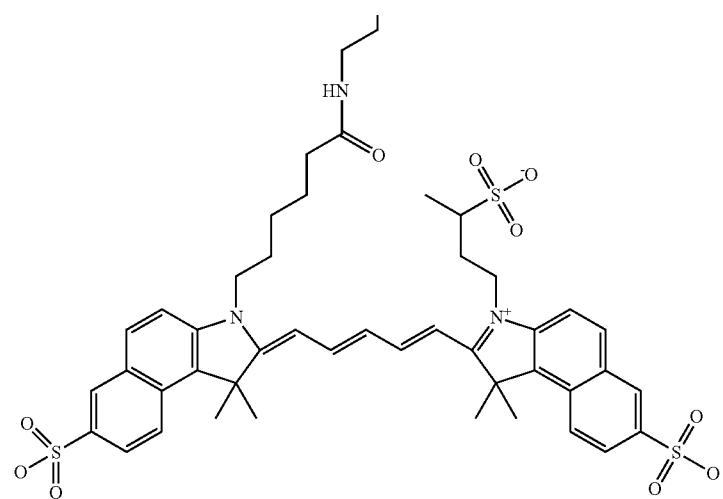
c(RGDyK)-Su-Lys(Cy 5.5)-Lys(Gd-DOTA)-NH₂
(42)

Example 15
This Example illustrates the synthesis of bi-modal TMIA, RGDyK-SMCC-K(Cy5.5)-K(Gd-DOTA)-NH2 by modular method, Compounds (43), (44).
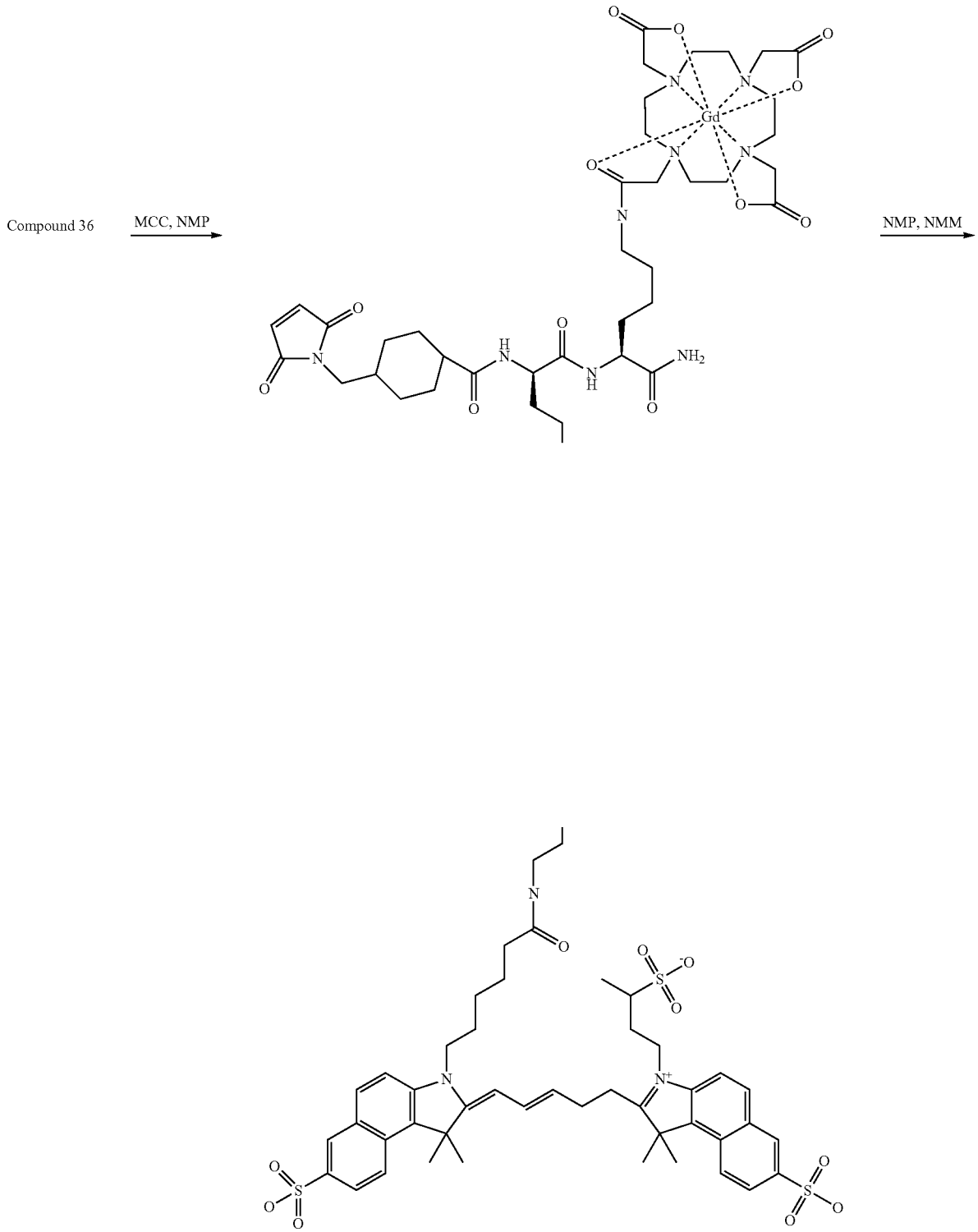
SMCC-DLys(Cy 5.5)-Lys(Gd-DOTA)-NH₂
(43) D, L isomer

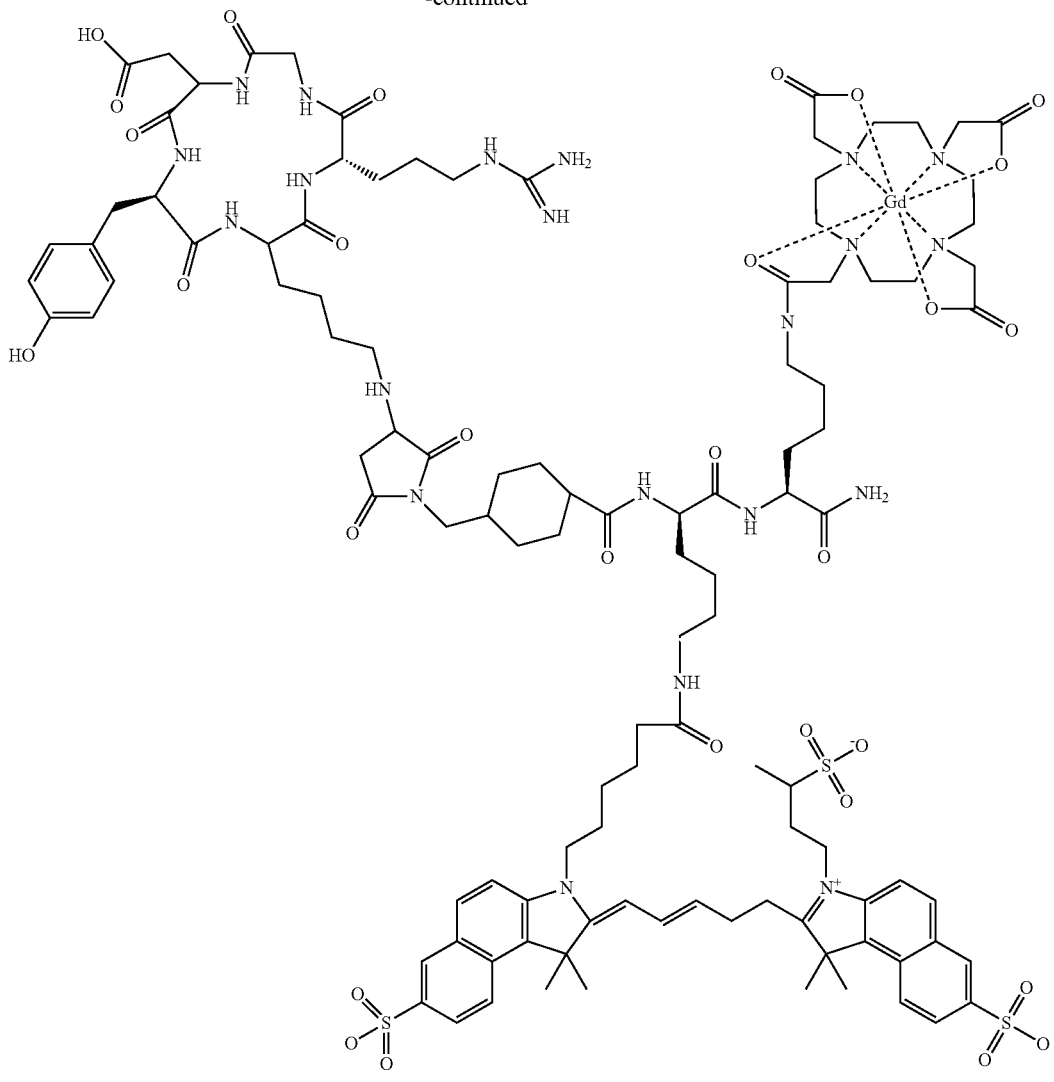

c(RGDyK)-SMCC-DLys(Cy 5.5)-Lys(Gd-DOTA)-NH₂

(44) D, L Isomer

Example 16

Synthesis of Compounds (1)-(44)

Compound (1a): Fmoc-Lys(Mtt)-NH$_2$

The solid Fmoc-Lys(Mtt)-OH (Bachem)(1 g, 1.6 mmol) was dissolved in of DCM (50 mL). Added in quick succession were HOBt (43.3 mg, 3.20×10⁻¹ mmol), DIPA (620 mg, 4.80 mmol), and TBTU (617 mg, 1.92 mmol). After 5 minutes, 30% ammonia (294.4 mg, 5.76 mmol) was added to the solution. The reaction was monitored every 0.5 h by TLC (50:50 mixture of EtAc:Hexanes). The reaction was run for 1 h. The solution was rotary evaporated and dried under high vacuum. Purification was done by extraction using DCM versus potassium sulfate, sodium carbonate, and sodium chloride with a sequential back extraction of aqueous layers with a single DCM layer. The product in organic phase was rotary evaporated and dried under high vacuum to yield an off-white foam. Yield: 934 mg (1.50 mmol, 93.6%); LC-MS=Calcd. for $C_{41}H_{41}N_3O_3$: 623.8 found: 624.6 [M+H]⁺.

Compound (1b): Fmoc-Lys(H)—NH$_2$

A solution of (1a) Fmoc-Lys(Mtt)-NH$_2$ (500 mg, 8.0×10⁻¹ mmol) in DCM (5 mL) was cooled to 4° C. in an ice bath. Once removed from the ice bath, TFA (0.5 mL, 10%) was added to the cooled down solution. The solution was then stirred for 0.5 h and was monitored via HPLC method A 20-100% every 0.25 h. The reaction was run for 1 h. The solution was rotary evaporated and dried under high vacuum. Purification was done through SPE using method B: 5-70%. The fractions were tested in the LC-MS with the same method used for the reaction. Pure product was found in fractions 30-40%. These fractions were combined, rotary evaporated, and dried under high vacuum. Yield: 280 mg (7.63×10⁻¹ mmol, 95.2%); LC-MS=Calcd. for $C_{21}H_{25}N_3O_3$: 367.2 (m/z), found: 368.4 [M+H]⁺.

Compound (2): Fmoc-Lys(DOTA-OtBu)-NH$_2$

The solid (1b) Fmoc-Lys(H)—NH$_2$ (60 mg, $1.63 \times 10^{-1}$ mmol) was heated in a 50:50 solution of DCM:DMF (6 mL) to dissolve the solid. Separately, the solid DOTA-triTBu (TCI) (112.23 mg, $1.96 \times 10^{-1}$ mmol) was dissolved in DCM (5 mL). To the dissolved DOTA-triTBu, HOBt (4.41 mg, $3.27 \times 10^{-2}$ mmol), TBTU (62.92 mg, $1.96 \times 10^{-1}$ mmol), and DIPA (84.42 mg, $6.53 \times 10^{-1}$ mmol) were added. These two separate solutions were then combined and the reaction was monitored every 0.5 h through LC-MS method A: 20-100%. The reaction was run for 3.5 h. The solution was rotary evaporated and dried under high vacuum. Purification was done via extraction using EtOAc and water with a sequential back extraction of aqueous layers with a single EtOAc layer. The product in organic phase was rotary evaporated and dried under high vacuum. Yield: 103.5 mg ($1.12 \times 10^{-1}$ mmol, 68.73%); LC-MS=Calcd. for $C_{49}H_{75}N_7O_{10}$: 922.6 (m/z), found: 921.9 [M−H]$^-$.

Compound (2): Fmoc-Lys(DOTA-OtBu)-NH$_2$, Scale Up

The solid (1b) Fmoc-Lys(H)—NH$_2$ (322.5 mg, $6.70 \times 10^{-1}$ mmol) was heated in a 50:50 solution of DCM:DMF (8 mL) to dissolve the solid. Separately, the solid DOTA-triTBu (TCI) (345.3 mg, $6.03 \times 10^{-1}$ mmol) was dissolved in DCM (5 mL). To the dissolved DOTA-triTBu TBTU (258.1 mg, $8.04 \times 10^{-1}$ mmol), and DIPA (519.4 mg, 4.02 mmol) were added. These two separate solutions were then combined and the reaction was monitored every 0.5 h through LC-MS method A: 20-100%. The reaction was run for 3.5 h. The solution was rotary evaporated and dried under high vacuum. Purification was done via extraction using EtOAc and water with a sequential back extraction of aqueous layers with a single EtOAc layer. The product in organic phase was rotary evaporated and dried under high vacuum. Yield: 609.4 mg ($6.6 \times 10^{-1}$ mmol, 98.6%); LC-MS=Calcd. for $C_{49}H_{75}N_7O_{10}$: 922.6 (m/z), found: 921.9 [M−H]$^-$.

Compound (3): Fmoc-Lys(DOTA-OH)—NH$_2$

To a solution of (2) Fmoc-Lys(DOTA-OtBu)-NH$_2$ (247.1 mg, $1.34 \times 10^{-1}$ mmol) in pure TFA (3 mL), 6 drops of deionized water was added (2 drops per 1 mL of TFA). The solution was stirred for 3.5 h at room temperature while using LC-MS method A: 50-100% to check the reaction progress every 0.5 h. Once the reaction was complete, the material was rotary evaporated, dried under high vacuum, and used without further purification in the subsequent step. Yield: 100.3 mg ($1.33 \times 10^{-1}$ mmol, 83.0%); LC-MS=Calcd. for $C_{37}H_{51}N_7O_{10}$: 753.4 (m/z), found: 752.7 [M−H]$^-$.

Compound (3): Fmoc-Lys(DOTA-OH)—NH$_2$, Scale Up

To a solution of (2) Fmoc-Lys(DOTA-OtBu)-NH$_2$ (626.0 mg, $6.79 \times 10^{-1}$ mmol) in pure TFA (5 mL), 10 drops of deionized water was added (2 drops per 1 mL of TFA). The solution was stirred for 3.5 h at room temperature while using LC-MS method A: 50-100% to check the reaction progress every 0.5 h. Once the reaction was complete, the material was rotary evaporated, dried under high vacuum, and used without further purification in the subsequent step. Yield: 502.0 mg ($6.66 \times 10^{-1}$ mmol, 98.1%); LC-MS=Calcd. for $C_{37}H_{51}N_7O_{10}$: 753.4 (m/z), found: 752.7 [M−H]$^-$.

Compound (4): Fmoc-Lys(Gd-DOTA)-NH$_2$

The solid (3) Fmoc-Lys(DOTA-OH)—NH$_2$ (176.2 mg, $2.34 \times 10^{-1}$ mmol) was dissolved in a buffer solution of pH 6 (6 mL). Separately, the solid Gd(OAc) (Alfa Aesar) (113.98 mg, $2.8 \times 10^{-1}$ mmol) was added to the solution. The reaction was stirred under argon gas and was monitored every 0.5 h by LC-MS method A. The reaction was run for 1.5 h. The solution was rotary evaporated and dried under high vacuum to remove the solvent. Purification was done through SPE using method B. The fractions were tested in the LC-MS with the same method used for the reaction. Pure product was found in fractions 50-60%. These fractions were combined, rotary evaporated, and dried under vacuum to yield a white solid. Yield: 77.2 mg ($8.49 \times 10^{-2}$ mmol, 36.3%); LC-MS=Calcd. for $C_{37}H_{49}GdN_7O_{10}$: 909.2 (m/z), found: 909.9 [M+H]$^+$.

Compound (4): Fmoc-Lys(Gd-DOTA)-NH$_2$, DMF Method

The solid (3) Fmoc-Lys(DOTA-OH)—NH$_2$ (250 mg, $3.32 \times 10^{-1}$ mmol) was dissolved in DMF (5 mL). Separately, the solid Gd(OAc) (Alfa Aesar) (269.5 mg, $6.63 \times 10^{-1}$ mmol) was added to the solution. The reaction was stirred under argon gas and was monitored every 0.5 h by LC-MS method A. The reaction was run for 1.5 h. The solution was rotary evaporated and dried under high vacuum to remove the solvent. Purification was done through SPE using method A. The fractions were tested in the LC-MS with the same method used for the reaction. Pure product was found in fractions 30-35%. These fractions were combined, rotary evaporated, and dried under vacuum to yield a white solid. Yield: 155.0 mg ($1.71 \times 10^{-1}$ mmol, 51.4%); LC-MS=Calcd. for $C_{37}H_{49}GdN_7O_{10}$: 909.2 (m/z), found: 909.9 [M+H]$^+$.

Compound (5): H-Lys(Gd-DOTA)-NH$_2$

To a solution of (4) Fmoc-Lys(Gd-DOTA)-NH$_2$ (20.0 mg, $2.00 \times 10^{-2}$ mmol) dissolved in DMF(2 mL), DEA (16.3 mg, $2.21 \times 10^{-1}$ mmol) was added drop-wise. The solution was stirred for 1 h at room temperature while using LC-MS method A: 20-100% to check the reaction progress every 0.5 h. Once the reaction was complete, the material was rotary evaporated. This concentrated material was then dissolved in H$_2$O and added to a separatory funnel for extraction using pure EtOAc for the organic layer and water for the aqueous layer. A sequential back extraction was done on the aqueous layers with a single layer of EtOAc. Product was found in the aqueous layer. Yield: 12.6 mg ($1.83 \times 10^{-2}$ mmol, 82.4%); LC-MS=Calcd. for $C_{22}H_{39}GdN_7O_8$: 686.9 (m/z), found: 685.6 [M−H]$^-$.

Compound (6b): Fmoc-Lys(H)—OH

A solution of (6a) Fmoc-DLys(Mtt)-OH (Anaspec) (1 g, 1.6 mmol) in DCM (10 mL) was cooled to 4° C. in an ice bath. Once removed from the ice bath, TFA (1 mL, 10%) was added to the cooled down solution. The solution was then stirred for 0.5 h and was monitored through LC-MS method A: 20-100% every 0.25 h. The reaction was run for 1 h. The solution was rotary evaporated. Ether was added followed by continued concentration and the product was dried under vacuum. Purification was not done on this product; the crude residue was used for the subsequent reactions. Yield: 380 mg (1.03 mmol, 64.4%); LC-MS=Calcd. for $C_{21}H_{24}N_2O_4$: 368.4 (m/z), found: 367.2 $[M-H]^-$.

Compound (7a): Fmoc-Lys(DOTA-OtBu)-OH

The solid (6c) Fmoc-Lys(H)—OH (196.5 mg, $5.33 \times 10^{-1}$ mmol) was dissolved in DCM (4 mL). Separately, the solid DOTA-OtBu (274.92 mg, $4.80 \times 10^{-1}$ mmol) was also dissolved in DCM (2 mL). To this dissolved DOTA compound, HATU (182.51 mg, $4.80 \times 10^{-1}$ mmol), and DIPA (413.58 mg, 3.20 mmol) were added. These two separate solutions were then combined and monitored every 0.5 h through LC-MS method A: 50-100%. The reaction was run for 2 h. The solution was rotary evaporated and dried under high vacuum to take off the solvent. Purification was done through SPE using method A: 20-100%. Product was found in fractions 70-80%. Yield: 0.216 g ($2.35 \times 10^{-1}$ mmol, 44.1%); LC-MS=Calcd. for $C_{49}H_{74}N_6O_{11}$: 923.1 (m/z), found: 921.9 $[M-H]^-$.

Compound (7b): Fmoc-Lys(DOTA-OH)—OH
(Deprotected DOTA not Shown)

To a solution of (7a) Fmoc-Lys(DOTA-OtBu)-OH (216.9 mg, $2.35 \times 10^{-1}$ mmol) in pure TFA (3 mL), 6 drops of deionized water was added (2 drops per 1 mL of TFA). The solution was stirred for 3.5 h at room temperature while using LC-MS method A: 50-100% to check the reaction progress every 0.5 h. Once the reaction was complete, the material was rotary evaporated, dried under vacuum, and used without further purification in the subsequent reaction step. Yield: 0.1602 g ($2.12 \times 10^{-1}$ mmol, 90.3%); LC-MS=Calcd. for $C_{37}H_{50}N_6O_{11}$: 754.8 (m/z), found: 753.6 $[M-H]^-$.

Compound (8): Fmoc-Lys(Gd-DOTA)-OH

The solid (7b) Fmoc-Lys(DOTA-OH)—OH (160 mg, $2.12 \times 10^{-1}$ mmol) was dissolved in a buffer solution of pH 6 (6 mL). Separately, the solid Gd(OAc) (103.37 mg, $2.54 \times 10^{-1}$ mmol) was added to the solution. A white precipitate was formed when the compounds were combined in solution. To dissolve the solid, methanol (6 mL) was added. The reaction was stirred and kept under argon gas and was monitored every 0.5 h through LC-MS method A: 20-100%. After 2 h the reaction was completed. The solution was rotary evaporated and dried under high vacuum to remove the solvent. Purification was done through SPE using method B. The fractions were tested in the LC-MS with the same method used for the reaction. Pure product was found in fractions 20-40%. These fractions were combined and rotary evaporated for further use. Yield: 0.084 g ($9.23 \times 10^{-2}$ mmol, 43.54%); LC-MS=Calcd. for $C_{37}H_{48}GdN_6O_{11}$: 910.1 (m/z), found: 908.9 $[M-H]^-$.

Compound (8): Fmoc-Lys(Gd-DOTA)-OH (one step method)

The solid DOTA-OH (Macrocyclics) (208.7 mg, $2.71 \times 10^{-1}$ mmol) was dissolved in DMF (10 mL). Once dissolved, DIPA (526.2 mg, 4.07 mmol) was added drop-wise to the solution to achieve a pH of 8. Next, TBTU (87.15 mg, $2.71 \times 10^{-1}$ mmol) dissolved in DMF (1 mL) was added drop-wise to the solution. The reaction was allowed to stir for 5 min. (6b) Fmoc-Lys(H)—OH (100 mg, $2.71 \times 10^{-1}$ mmol) dissolved in DMF (3 mL) was added drop-wise. Again, the reaction was allowed to stir for 5 min. Next, Gd(OAc)$_3$ (132.4 mg, $3.26 \times 10^{-1}$ mmol) dissolved in DMF (2 mL) was added to the solution. The reaction was stirred under argon gas and was monitored every 0.5 h through LC-MS method A: 20-100%. After 2 h DIPA (175.4 mg, 1.36 mmol) and TBTU (10.5 mg, $3.26 \times 10^{-2}$ mmol) were added to the reaction mixture. After 5 h the reaction was complete. The solution was rotary evaporated and dried under high vacuum to remove the solvent. Purification was done through SPE using method B. The fractions were tested in the LC-MS with the same method used for the reaction. Pure product was found in fractions 40-50%. The purest fractions were combined and rotary evaporated for further use. Yield (pure fractions): 37.6 g ($2.13 \times 10^{-2}$ mmol, 15.2%); Total with slightly impure fractions which were separately re-purified, 91 mg ($1.02 \times 10^{-1}$ mmol, 37.2%); ((LC-MS=Calcd. for $C_{37}H_{48}GdN_6O_{11}$: 910.1 (m/z), found: 908.7 $[M-H]^-$.

Compound (9): Fmoc-Lys(Eu$^{III}$-DOTA)-NH$_2$

The solid (3) Fmoc-Lys(DOTA-OH)—NH$_2$ (10.0 mg, $1.33 \times 10^{-2}$ mmol) was dissolved in DMF (1 mL). Separately, the solid Eu(NO$_3$)$_3$ (Aldrich) (17.0 mg, $3.98 \times 10^{-2}$ mmol) was added to the solution. The reaction was stirred under argon gas for 40 min after which the reaction was complete by LC-MS method A: 20-100%. The solution was rotary evaporated and dried under high vacuum to remove the solvent. Purification was done through SPE using method A: 10-100%. The fractions were tested in the LC-MS with the same method used for the reaction. Pure product was found in fractions 25-30%. These fractions were combined, rotary evaporated and dried under vacuum to yield a white solid. Yield: 4.0 mg ($4.43 \times 10^{-3}$ mmol, 34.1%); LC-MS=Calcd. for $C_{37}H_{48}EuN_7O_{10}$: 903.27 (m/z), found: 902.8 $[M+H]^+$.

Compound (10): Fmoc-Lys(Eu$^{II}$-DOTA)-NH$_2$

The solid (3) Fmoc-Lys(DOTA-OH)—NH$_2$ (10.0 mg, $1.33 \times 10^{-2}$ mmol) was dissolved in DMF (1 mL). Separately, the solid EuBr$_2$ (Alfa Aeser) (12.41.0 mg, $3.98 \times 10^{-2}$ mmol) was added to the solution. The reaction was stirred under argon gas for 40 min after which the reaction was complete by LC-MS method A: 20-100%. The solution was rotary evaporated and dried under high vacuum to remove the solvent. Purification was done through SPE using method A: 10-100%. The fractions were tested in the LC-MS with the same method used for the reaction. Pure product was found in fractions 25-30%. These fractions were combined, rotary evaporated, and dried under vacuum to yield a white solid. Yield: 11.0 mg ($1.20 \times 10^{-2}$ mmol, 90.6%); LC-MS=Calcd. for $C_{37}H_{48}EuN_7O_{10}$: 903.27 (m/z), found: 902.8 $[M+H]^+$.

Compound (11): Fmoc-Lys(Ce-DOTA)-NH$_2$

The solid (3) Fmoc-Lys(DOTA-OH)—NH$_2$ (10.0 mg, $1.33 \times 10^{-2}$ mmol) was dissolved in DMF (1 mL). Separately, the solid Ce(NO$_3$)$_2$ (Alfa Aeser) (12.41.0 mg, $3.98 \times 10^{-2}$ mmol) was added to the solution. The reaction was stirred under argon gas for 40 min after which the reaction was complete by LC-MS method A: 20-100%. The solution was rotary evaporated and dried under high vacuum to remove the solvent. Purification was done through SPE using method A: 10-100%. The fractions were tested in the LC-MS with the same method used for the reaction. Pure product was found in fractions 25-30%. These fractions were combined, rotary evaporated, and dried under vacuum to yield a white solid. Yield: 11.0 mg ($1.20\times10^{-2}$ mmol, 90.6%); LC-MS=Calcd. for $C_{37}H_{48}EuN_7O_{10}$: 890.25 (m/z), found: 889.4[M−H]$^+$. (With Eu isotope pattern)

Compound (12): Fmoc-Lys(Cu-DOTA)-NH$_2$: Method A.

The freeze-dried solid (11) F-K(DOTA-Ce(III))-NH$_2$ (11.2 mg, $1.25\times10^{-3}$ mmol) was dissolved in 2 mL of 50% acetonitrile then sonicated for approximately 20 minutes. The resulting solution had a concentration of 0.0063M. 115.1 mg of Cu(NO$_3$)$_2$ was dissolved in 9.7 mL of water to make a 0.063M solution. 200 µL of the F-K(DOTA-Ce(III))-NH$_2$ solution and 200 µL of the Cu(NO$_3$)$_2$ solution were added to an HPLC vial. To make the reaction environment acidic, 400 µL of 0.2M TFA at pH 2.01 was added to the HPLC vial. The reaction was monitored after 24 hours (by LC-MS method A: 20-100%) and found to be partial conversion to the Cu complex. After five days conversion was complete. In subsequent experiments in HPLC vials, it was determined that by increasing acidity the Ce could be removed faster. This could be followed by introducing the Cu solution and purification or insertion of metal and purification could be accomplished by SPE (SPE Method A: 50-100%). The product was left in solution and assayed by LC-MS=Calcd. for $C_{37}H_{48}CuN_7O_{10}$: 813.3 (m/z), found: 813.8 [M] (with Cu isotope pattern)

Compound (12): Fmoc-Lys(Cu-DOTA)-NH$_2$: Method B.

The freeze-dried solid (1×) F-K(DOTA-Eu(II))-NH$_2$ (3.5 mg $3.87\times10^{-3}$ of F-K(DOTA-Eu(II))-NH$_2$ was dissolved in 0.6 mL of 50% acetonitrile. The resulting solution had a concentration of 0.0065M. 200 µL of the F-K(DOTA-Eu(II))-NH$_2$ solution and 200 µL of a 0.063M Cu(NO$_3$)$_2$ solution were added to an HPLC vial. To make the reaction environment acidic, 400 µL of 0.2M TFA at pH 2.01 was added to the HPLC vial. The reaction was monitored after one 24 and 48 h (by LC-MS method A: 20-100%) and found to be partial conversion to the Cu complex. After five days conversion was still a mixture. It was determined that increasing acidity speeds up the exchange. The product was left in solution and assayed by LC-MS=Calcd. for $C_{37}H_{48}CuN_7O_{10}$: 813.3 (m/z), found: 813.7 [M] (with Cu isotope pattern)

Compound (13b): Fmoc-DLys(Cy5.5)—OH

The NIRF dye Cy5.5 (25.0 mg, $2.89\times10^{-2}$ mmol) was dissolved in DMF (2.5 mL) followed by addition of HOBt (1.8 mg, $1.30\times10^{-2}$ mmol) and DIPA (93.49 mg, $7.23\times10^{-1}$ mmol). HATU (14.0 mg, $3.62\times10^{-2}$ mmol) was added and the activation was monitored through a dilute benzyl amine quench through HPLC method B: 30-100%. After 20 minutes, (6d) Fmoc-DLys(H)—OH (Bachem) (10.7 mg, $2.89\times10^{-2}$ mmol) was added. The reaction was stirred for 30 min. The reaction was cooled and concentrated under high vacuum, followed by purification by SPE method B: 10-100%. The product was found in fractions 30-40%. The purest fractions were concentrated and freeze dried. Pure Yield: 12 mg ($0.988\times10^{-2}$, 34.2%). Total yield: 17 mg ($1.40\times10^{-2}$ mmol, 48%). LC-MS=Calcd. for $C_{64}H_{72}N_5O_{13}S_3$: 1214.4, found: 1213.6 [M−H]$^-$, 606.3 [M−H/2]$^-$.

Compound (14): Fmoc-Lys(Cy5.5)-NH$_2$

The solid, NIRF dye Cy5.5 (25.0 mg, $2.89\times10^{-2}$ mmol) was dissolved in NMP (1.5 mL) and the solution was dried with two 3A molecular sieves for 10 min, followed by addition of HOBt (0.5 mg, $3.60\times10^{-3}$ mmol) and DIPA (18.6 mg, $1.45\times10^{-1}$ mmol). HATU (16.48 mg, $4.34\times10^{-2}$ was added to the reaction. After pre-activation, (1b) Fmoc-Lys (H)—NH$_2$ (16.70 mg, $3.47\times10^{-2}$ mmol) was added followed by stirring at ambient temperature for 2 h. The reaction was cooled and concentrated under high vacuum, followed by purification by SPE method B: 10-100%. The product was found in fractions 40-50%. The purest fractions were concentrated and freeze dried. Pure Yield: 13 mg ($1.07\times10^{-2}$, 37.0%). LC-MS=Calcd. for $C_{64}H_{71}N_5O_{13}S_3$: 1213.4, found: 1212.5 [M−H]$^-$, 607.2 [M−H/2]$^-$.

Compound (15): H-Lys(Cy5.5)-NH$_2$

To a solution of (14) Fmoc-Lys(Cy5.5)-NH$_2$ (12.1 mg, $1.0\times10^{-2}$ mmol) dissolved in DMF (2 mL), DEA (10.0 mg, $1.39\times10^{-1}$ mmol) was added drop-wise. The solution was stirred for 6 h at room temperature while using LC-MS method A: 20-100% to check the reaction progress every 2 h. Once the reaction was complete, the material was rotary evaporated. This concentrated material was then dissolved in H$_2$O and added to a separatory funnel for extraction using pure EtOAc for the organic layer and water for the aqueous layer. A sequential back extraction was done on the aqueous layers with a single layer of EtOAc. Product was found in the aqueous layer. Yield: 5.2 mg ($5.25\times10^{-3}$ mmol, 52.5%); LC-MS=Calcd. for $C_{49}H_{60}N_5O_{11}S_3$: 990.3.3 (m/z), found: 989.4.4 [M−H]$^-$.

Compound (16b) Fmoc-DLys(Cy7s)-OH

The NIRF dye Cy7 (50.0 mg, $6.55\times10^{-2}$ mmol) was dissolved in DMF (1.5 mL) followed by the addition of DIPA (169.4 mg, 1.31 mmol). The coupling agent COMU (42.1 mg, $9.83\times10^{-2}$ mmol) was added and the activation was monitored through a dilute benzyl amine quench through HPLC method B: 30-100%. After 5 min, (6d) Fmoc-DLys(H)—OH (26.5, $6.55\times10^{-2}$ mmol) was added. The reaction was stirred for 30 min. The reaction was cooled, quenched with 5 mL water and concentrated under high vacuum, followed by purification by SPE method B:10-80%. The product was found in fractions 30-40%. The purest fractions were concentrated and freeze dried. Pure yield: 7.0 mg ($6.28\times10^{-3}$, 10.0%). Total yield including second recycled SPE: 18 mg ($1.60\times10^{-2}$ mmol, 24.7%). LC-MS=Calcd. for $C_{56}H_{64}N_4O_{14}S_3$: 1112.4, found: 1211.5 [M−H]$^-$, 605.3[M−H/2]$^-$.

Compound (17): Fmoc-Lys(Cy7)-NH$_2$

The solid, NIRF dye Cy7 (25.0 mg, $3.28\times10^{-2}$ mmol) was dissolved in DMF (1.5 mL) and the solution was dried with two 3A molecular sieves for 10 min, followed by addition of HOBt (0.4 mg, $2.89\times10^{-3}$ mmol), DIPA (50.82 mg, $3.93\times10^{-1}$ mmol), and TBTU (13.15 mg, $4.10\times10^{-2}$ mmol). After pre-activation, (1b) Fmoc-Lys(H)—NH$_2$ (15.78 mg, $3.28\times10^{-2}$ mmol) was added followed by stifling at ambient temperature for 2 h. The reaction was cooled and concentrated under high vacuum, followed by purification by SPE method B: 10-100%. The product was found in fractions 40-50%. The purest fractions were concentrated and freeze dried. Pure Yield: 12 mg ($1.07\times10^{-2}$, 32.9%). LC-MS=Calcd. for $C_{56}H_{65}N_5O_{13}S_3$: 1111.4, found: 1110.6 [M−H]$^-$, 555.3 [M−H/2]$^-$.

Compound (18): H-Lys(Cy7)-NH$_2$

To a solution of (17) Fmoc-Lys(Cy7)-NH$_2$ (6.0 mg, $5.39\times10^{-3}$ mmol) dissolved in DMF (2 mL), DEA (9.87 mg, 1.35×10⁻¹ mmol) was added drop-wise. The solution was stirred for 6 h at room temperature while using LC-MS method A: 20-100% to check the reaction progress every 2 h. Once the reaction was complete, the material was rotary evaporated. This concentrated material was then dissolved in H$_2$O and added to a separatory funnel for extraction using pure EtOAc for the organic layer and water for the aqueous layer. A sequential back extraction was done on the aqueous layers with a single layer of EtOAc. Product was found in the aqueous layer. Yield: 4.2 mg (4.72×10⁻³ mmol, 87.5%); LC-MS=Calcd. for C$_{41}$H$_{55}$N$_5$O$_{11}$S$_3$: 889.3 (m/z), found: 688.4 [M−H]⁻.

Compound (19): Fmoc-Lys(Cy7)-OH

The solid, NIRF dye Cy7 (9.1 mg, 1.36×10⁻² mmol) was dissolved in NMP (2.0 mL) and the solution was dried with two 3A molecular sieves for 10 min, followed by addition of DSC 13.4 mg, 5.23×10⁻² mmol) and NHS (3.44 mg, 2.99×10⁻² mmol) and after stirring 5 minutes DIPA (38.65 mg, 2.99×10⁻¹ mmol) was added. The solution was warmed at 50° C. 30 min. (1b) Fmoc-Lys(H)—NH$_2$ (5.0 mg, 1.36×10⁻² mmol) was added followed by stifling at ambient temperature for 2 h. The reaction was cooled and concentrated under high vacuum, followed by purification by SPE method B: 10-100%. The product was found in fractions 40-50%. The purest fractions were concentrated and freeze dried. Pure Yield: 10 mg (9.8×10⁻³, 72.1%). LC-MS=Calcd. for C$_{55}$H$_{62}$N$_4$O$_{11}$S$_2$: 1018.4, found: 1017.6 [M−H]⁻, 508.6 [M−H/2]⁻.

Compound (20): Cbz-Ala(Cyclen)-Bn was made by the method of Eszter, et al[12].

Compound (21): Cbz-Ala(DOTA-OtButyl)-Bn

The (20) Cbz-Ala(Cyclen)-Bn (1.81 g, 3.72 mmol)[12] was dissolved in ACN (50 mL) along with potassium carbonate (5.16 g, 37.2 mmol). tbutyl bromoacetate (2.32 g, 11.9 mmol) was added drop-wise to the cloudy mixture. The reaction was stirred at room temperature overnight. The mixture was vacuum-filtered to remove the precipitate. The solvent was removed through rotary evaporation and high vacuum. The residue was dissolved in EtOAc and extracted with water, a mild acid, and brine. The organic layer was dried with Na$_2$SO$_4$ which was then filtered out. The solvent was removed through rotary evaporation. Yield: 3.33 g (4.03 mmol, >theorized). LC-MS=Calcd. for C$_{44}$H$_{67}$N$_5$O$_{10}$: 826.0 (m/z), found: 824.8 [M−H]⁻.

Compound (22): Cbz-Ala(DOTA-OH)-Bn

The (21) Cbz-Ala(DOTA-OtButyl)-Bn (0.25 g, 0.303 mmol) was chilled in an ice bath for several min. The solid was dissolved in pure TFA (5 mL) and the ice bath was removed. The reaction stirred overnight at room temperature. Solvent removal through rotary evaporation was followed by the addition of ethyl ether (3 mL) to precipitate the product from the remaining TFA. The liquid was vacuum dried, leaving behind a white solid. The product was not purified; the crude material was used for further reactions. Yield: 0.1025 g (1.56×10⁻¹ mmol, 51.5%). LC-MS=Calcd. for C$_{32}$H$_{43}$N$_5$O$_{10}$: 657.7 (m/z), found: 658.6 [M+H]⁺.

Compound (23): Cbz-Ala(Gd-DOTA)-Bn

The (22) Cbz-Ala(DOTA-OH)-Bn (0.1025 g, 0.156 mmol) was dissolved in DMF (3 mL). Gd(OAc)$_3$ (0.127 g, 0.312 mmol) was added to the solution. The reaction was stirred at room temperature for 3 h. The solvent was removed with rotary evaporation. The residue was suspended in a roughly 20% mixture of ACN in water and purified through SPE using method A: 5-60%. The product was found in fractions 45-55%. These fractions were combined and rotary evaporated. Yield: 0.0955 g (1.18×10⁻¹ mmol, 75.6%). LC-MS=Calcd. for C$_{32}$H$_{40}$N$_5$O$_{10}$Gd: 811.9 (m/z), found: 813.6 [M+H]⁺.

Compound (24): NH$_2$-Ala(Gd-DOTA)-OH

Catalytic hydrogenation of (23) Cbz-Ala(Gd-DOTA)-Bn (0.0955 g. 0.118 mmol) was carried out by dissolving the Gd compound in methanol (10 mL). Formic acid (250 µL) was added to the solution followed immediately by activated Pd—C (100 mg, 0.940 mmol). The flask was sealed and stirred at room temperature for 2 h. The Pd—C was filtered and the solvent was removed through rotary evaporation. The product was not purified and used directly in subsequent reactions. Yield: 0.050 g (8.51×10⁻² mmol, 72.1%). LC-MS=Calcd. for C$_{17}$H$_{28}$N$_5$O$_8$Gd: 587.7 (m/z), found: 589.4 [M+H]⁺.

Compound (25): Fmoc-Ala(DOTA-Gd)—OH

The unprotected (24) NH$_2$-Ala(Gd-DOTA)-OH (0.050 g, 0.0851 mmol) was dissolved in ACN (3 mL). Sodium Carbonate (0.02705 g, 0.255 mmol) was dissolved in deionized water (3 mL) and added to the reaction mixture. The clear solution was stirred in an ice bath for 5 minutes while Fmoc-Cl (0.0264 g, 0.102 mmol) was dissolved in ACN (2 mL). The ice bath was removed and the Fmoc-Cl was added to the reaction. The solution was stirred 4 h. Purification was done through SPE method A: 5-50% with pure product found in fractions 10-15%. Those fractions were combined and the solvent was removed through rotary evaporation. Yield: 0.0121 g (1.49×10⁻² mmol, 17.6%). LC-MS=Calcd. for C$_{32}$H$_{38}$N$_5$O$_{10}$Gd: 809.9 (m/z), found: 811.3 [M+H]⁺.

Compound (26): Fmoc-Ala(DOTA-Gd)-Lys(Cbz)-NH$_2$

Compound (27): Fmoc-Lys(Gd-DOTA)-Lys(Gd-DOTA)-NH$_2$

The solid (8) Fmoc-Lys(Gd-DOTA)-OH (9.8 mg, 1.08×10⁻² mmol) was dissolved in DMF (0.5 mL). Added to this solution were DIPA (13.92 mg, 1.08×10⁻¹ mmol) and TBTU (4.84 mg, 1.51×10⁻² mmol). To this solution, (5) H-Lys(Gd-DOTA)-NH$_2$ (7.4 mg, 1.08×10⁻² mmol) dissolved in DMF (0.5 mL) was added. The reaction was stirred under argon gas and was monitored every 0.5 h through LC-MS method B. The LC-MS showed the mass of the product and its half weight as well as consecutive loss of one to three acetic acids. After 2 h the reaction was completed. The solution was rotary evaporated and dried under high vacuum to remove the solvent. Purification was done through SPE using method B. Product was found in fractions 50-60%. These pure fractions were combined, concentrated through rotary evaporation and dried under high vacuum. Yield: 5.1 mg (3.23×10⁻³ mmol, 30.0%); LC-MS=Calcd. for C$_{59}$H$_{85}$GdN$_{13}$O$_{18}$: 1578.9 (m/z), found: 1577.5 [M−H]⁻.

Compound (28): H-Lys(Gd-DOTA)-Lys(Gd-DOTA)-NH$_2$

To a solution of (27) Fmoc-Lys(Gd-DOTA)-Lys(Gd-DOTA)-NH$_2$ (3.70 mg, 2.34×10⁻³ mmol) dissolved in NMP (0.25 mL), DEA (3.43 mg, 4.69×10$^{-2}$ mmol) was added drop-wise. The solution was stirred for 2 h at room temperature while using LC-MS method B: 30-100% to check the reaction progress every 0.5 h. After 2 h, DEA (1.71 mg, 2.34×10$^{-2}$ mmol) was added. After 4 h, additional DEA (3.43 mg, 4.69×10$^{-2}$ mmol) was added. After 24 h the reaction was complete and the material was rotary evaporated. This concentrated material was then dissolved in H$_2$O and added to a separatory funnel for extraction using pure EtOAc for the organic layer and water for the aqueous layer. A sequential back extraction was done on the aqueous layers with a single layer of EtOAc. Product was found in the aqueous layer. Yield: 3.50 mg (2.58×10$^{-3}$ mmol, >theory); LC-MS=Calcd. for C$_{44}$H$_{75}$Gd$_2$N$_{13}$O$_{16}$: 1356.6 (m/z), found: 1354.7 [M–H]$^-$.

Compound (29): SMCC-Lys(Gd-DOTA)-Lys(Gd-DOTA)-NH$_2$

Figure 3:
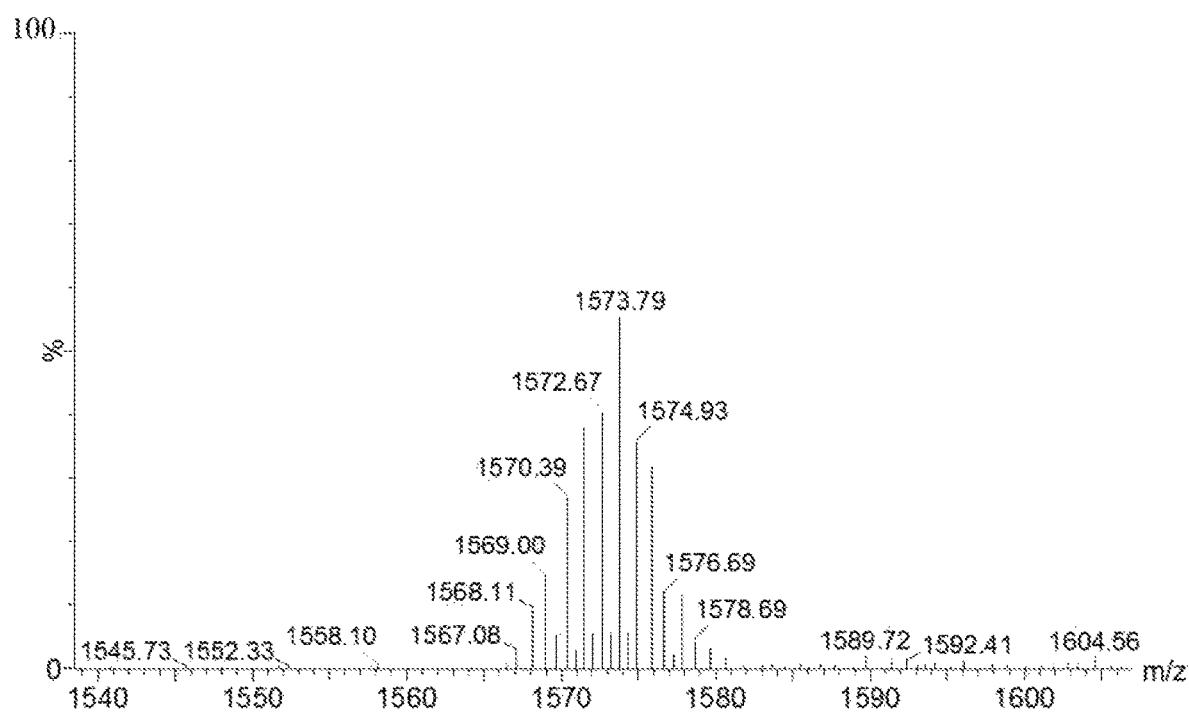
FIG. 3 is a mass spectra of Compound (29) (di-Gd isotope pattern)

To a solution of (28) H-Lys(Gd-DOTA)-Lys(Gd-DOTA)-NH$_2$ (3.50 mg, 2.58×10$^{-3}$ mmol) dissolved in PBS buffer (0.25 mL) of pH 8.5, the SMCC linker (2.20 mg, 6.45×10$^{-3}$ mmol) in DMF (0.25 mL) was added. The solution was stirred for 1.5 h at room temperature while using LC-MS methanol B: 20-100% to check the reaction progress every 0.5 h. Once the reaction was complete, the material was concentrated down. The product was purified through SPE method B: 10-50%. The product was found in fractions 15-25%. Yield: 4.0 mg (2.54×10$^{-2}$ mmol, 98.3%); LC-MS=Calcd. for C$_{56}$H$_{88}$Gd$_2$N$_{14}$O$_{19}$: 1575.8 (m/z), found: 1573.8 [M–H]$^-$. The mass spectra of this compound is shown in FIG. 3, displaying the di-Gd isotope pattern.

Compound (30) c(RGDyK)-SMCC-DLys(Gd-DOTA)-Lys(Gd-DOTA)-NH$_2$

To a solution of (29) SMCC-Lys(Gd-DOTA)-Lys(Gd-DOTA)-NH$_2$ (4.0 mg, 2.70×10$^{-3}$ mmol) dissolved in NMP (0.80 mL), the targeting peptide c(RGDyK) (Peptides, International) (1.70 mg, 2.75×10$^{-3}$ mmol) in NMP (0.25 mL) with NMM (0.22 mg, 2.17×10$^{-3}$ mmol) was added. The solution was stirred for 6 h at room temperature while using LC-MS method B: 30-100% to check the reaction progress. After 6 h 6, additional NMM (1.36 mg, 1.34×10$^{-3}$ mmol) was added. The reaction was completed in 76 h. Once the reaction was complete, the material was concentrated down through rotary evaporation. The product was purified through SPE method B: 10-50% with product found in fractions 30-40%. Yield: 2.2 mg (1.03×10$^{-3}$ mmol, 38.1%); LC-MS=Calcd. for C$_{83}$H$_{129}$Gd$_2$N$_{23}$O$_{27}$: 2195.79 (m/z), found: 728.6 [M–3H/3]$^-$ Compound (31): Fmoc-Lys(Cbz)-Lys(Gd-DOTA)-NH$_2$ The solid Fmoc-Lys(Cbz)-OH (9.21 mg, 1.83×10$^{-2}$ mmol) was dissolved in DMF (2 mL). Added to this solution were DIPA (2.37 mg, 1.83×10$^{-2}$ mmol) and HATU (6.97 mg, 1.83×10$^{-2}$ mmol). To this solution, (5) H-Lys(Gd-DOTA)-NH$_2$ (12.60 mg, 8.73×10$^{-2}$ mmol) dissolved in DMF (2 mL) was added. The reaction was stirred under argon gas and was monitored every 0.5 h through LC-MS method A: 20-100%. After 1 h the reaction was completed. The product was found in the LC-MS with a consecutive loss of acetic acid fragmentation. The solution was rotary evaporated and dried under high vacuum to remove the solvent. The product was purified through SPE using method A. The product was found in fractions 70-80%. Yield: 2.2 mg (1.88×10$^{-3}$ mmol, 10.2%); LC-MS=Calcd. for C$_{51}$H$_{67}$GdN$_9$O$_{13}$: 1171.4 (m/z), found: 1170.1 [M–H]$^-$.

Compound (32a): Fmoc-Lys(Mtt)-Lys(Gd-DOTA)-NH$_2$

The solid Fmoc-Lys(Mtt)-OH (Bachem)(18.2 mg, 2.91×10$^{-2}$ mmol) was dissolved in DMF (2 mL). Added to this solution were DIPA (37.6 mg, 2.91×10$^{-1}$ mmol) and TBTU (39.27 mg, 1.22×10$^{-1}$ mmol). The solution was cooled in an ice bath to 10° C. and allowed to pre-activate for 5 min. To this solution, (5) H-Lys(Gd-DOTA)-NH$_2$ (20 mg, 2.91×10$^{-2}$ mmol) dissolved in DMF (2 mL) was added once removed from the ice bath. The reaction was stirred and kept under argon gas and was monitored every 0.5 h through LC-MS method A: 50-100%. After 1.5 h the reaction was completed. The solution was rotary evaporated and dried under high vacuum to remove the solvent. The product was purified through SPE using method A: 20-100%. The product was found in fractions 60-70%. Yield: 0.010 g (7.73×10$^{-3}$ mmol, 26.53%); LC-MS=Calcd. for C$_{63}$H$_{77}$GdN$_9$O$_{11}$: 1293.6 (m/z), found: 1292.3 [M–H]$^-$.

Compound (32b): Fmoc-DLys(Mtt)-Lys(Gd-DOTA)-NH$_2$

The solid Fmoc-DLys(Mtt)-OH (Bachem) (54.49 mg, 8.74×10$^{-2}$ mmol) was dissolved in DMF (4 mL). Added to this solution were DIPA (112.89 mg, 8.74×10$^{-1}$ mmol) and TBTU (11.2 mg, 3.49×10$^{-2}$ mmol). The solution was cooled in an ice bath to 10° C. and allowed to pre-activate for 5 min. To this solution, (5) H-Lys(Gd-DOTA)-NH$_2$ (60.00 mg, 8.74×10$^{-2}$ mmol) dissolved in DMF (4 mL) was added once removed from the ice bath. The reaction was stirred under argon gas and was monitored every 0.5 h through LC-MS method A: 30-100%. After 1.5 h the reaction was completed. The solution was rotary evaporated and dried under high vacuum to remove the solvent. The product was purified through SPE using method A: 30-100%. The product was found in fractions 60-80%. Yield: 0.0471 g (3.64×10$^{-2}$ mmol, 41.7%); LC-MS=Calcd. for C$_{63}$H$_{77}$GdN$_9$O$_{11}$: 1293.6 (m/z), found: 1292.2 [M–H]$^-$.

Compound (33): Fmoc-DLys(H)-Lys(Gd-DOTA)-NH$_2$

A solution of (32b) Fmoc-DLys(Mtt)-Lys(Gd-DOTA)-NH$_2$ (47.10 mg, 3.64×10$^{-2}$ mmol) in DCM (5 mL) was cooled to 4° C. in an ice bath. TFA (0.5 mL) was added to the cooled solution. The solution was then stirred for 0.5 h at ambient temperature and was monitored through LC-MS method A: 20-100% every 0.25 h. After 1 h the reaction was complete. The solution was rotary evaporated and dried under high vacuum to take off the solvent. Purification was done through SPE using method B: 10-90%. The fractions were tested in the LC-MS with the same method used for the reaction. Pure product was found in fractions 20-30%. Yield: 0.0152 g (1.47×10$^{-2}$ mmol, 40.1%); LC-MS=Calcd. for C$_{43}$H$_{61}$GdN$_9$O$_{11}$: 1037.3 (m/z), found: 1036.4 [M–H]$^-$.

Compound (34): Fmoc-DLys(Cy5.5)-Lys(Gd-DOTA)-NH$_2$ by Method A

The solid Cy 5.5 dye (4.50 mg, 5.21×10$^3$ mmol) was dissolved in DMF (1 mL). One 3A and one 4A molecular sieve was added to the solution and allowed to dry for 10 min and then removed from the solution. Added to this solution were DIPA (13.46 mg, $1.04\times10^{-1}$ mmol), TBTU (2.09 mg, $6.51\times10^{-3}$ mmol), and HOBt (0.32 mg, $2.34\times10^{-3}$ mmol) and allowed to activate for 5 min. (33) Fmoc-DLys(H)-Lys(Gd-DOTA)-$NH_2$ (5.40 mg, $5.21\times10^{-3}$ mmol) dissolved in DMF (1 mL) and had one 4A and one 3A molecular sieve added and allowed to dry for 10 min. The two solutions were then combined and the reaction was stirred and kept under argon gas and was monitored every 0.5 h through LC-MS method B: 30-100%. After 1.5 h the reaction was completed. The solution was rotary evaporated and dried under high vacuum to remove the solvent. The product was purified through SPE using method B: 5-70%. The product was found in fractions 30-55%. These were combined and concentrated and dried under high vacuum.

Compound (35): Fmoc-Lys(Gd-DOTA)-Lys(Cbz)-$NH_2$

The solid (8) Fmoc-Lys(Gd-DOTA)-OH (24.0 mg, $2.64\times10^{-2}$ mmol) was dissolved in NMP (1.0 mL). Added to this solution were DIPA (34.0 mg, $2.64\times10^{-1}$ mmol) and HATU (10.03 mg, $2.64\times10^{-2}$ mmol). To this solution, H-Lys(Cbz)-$NH_2$ (7.4 mg, $2.64\times10^{-2}$ mmol) dissolved in NMP (0.5 mL) was added. The reaction was stirred under argon gas and was monitored every 1 h through LC-MS method A. The LC-MS showed the mass of the product as well as the half weight. After 2 h the reaction was completed. The solution was rotary evaporated and dried under high vacuum to remove the solvent. Purification was done through SPE method A. Product was found in fractions 30-50%. These pure fractions were combined, concentrated through rotary evaporation, and dried under high vacuum. Yield: 6.0 mg ($5.12\times10^{-3}$ mmol, 20.0%); LC-MS=Calcd. for $C_{51}H_{70}GdN_9O_{13}$: 1171.4 (m/z), found: 1170.5 $[M-H]^-$.

Compound (35b): H-Lys(Gd-DOTA)-Lys(H)—$NH_2$

Fmoc-Lys(Gd-DOTA)-Lys(Cbz)-$NH_2$ (35a) (6.0 mg, $5.13\times10^{-3}$ mmol) was dissolved in methanol (1.0 mL). Under argon, formic acid was added (70 μL) followed by activated 10% palladium on carbon (6.00 mg). The reaction was stirred at room temperature for 2 h before it was analyzed with LC-MS method A. The reaction was filtered, concentrated by rotary evaporation to yield the product as a solid: yield: 4.0 mg ($3.86\times10^{-3}$ mmol (75.2%)); LC-MS=Calcd. For $C_{43}H_{60}N_9O_{11}Gd$: 1036.2 (m/z) found: 1034.7 $[M-H]^-$.

Compound (36b): H-DLys(Cy5.5)-Lys(Gd-DOTA)-$NH_2$

To a solution of (34) Fmoc-DLys(Cy5.5)-Lys(Gd-DOTA)-$NH_2$ (11.7 mg, $6.21\times10^{-3}$ mmol) dissolved in DMF (2 mL), DEA (4.54 mg, $6.21\times10^{-2}$ mmol) was added dropwise. The solution was stirred for 1 h at room temperature while using LC-MS method A: 20-100% to check the reaction progress every 0.5 h. Once the reaction was complete, the material was rotary evaporated down. This concentrated material was then dissolved in $H_2O$ and added to a separatory funnel for extraction using pure EtOAc for the organic layer and water for the aqueous layer. A sequential back extraction was done on the organic layers with one single layer of EtOAc. Product was found in the aqueous layer, which had a characteristic blue color. This was then concentrated down and used for further reactions. Yield: 2.7 mg ($1.57\times10^{-3}$ mmol, 25.3%); LC-MS=Calcd. for $C_{71}H_{97}GdN_{11}O_{19}S_3$: 1662.1 (m/z), found: 830.6 $[M-H/2]^-$.

Compound (37): Su-Lys(Gd)—$NH_2$

To a solution of (5) H-Lys(Gd-DOTA)-$NH_2$ (10.0 mg, $1.45\times10^{-2}$ mmol) dissolved in DMF (2 mL), DIPA (7.54 mg, $5.79\times10^{-2}$ mmol) was added. Su linker (1.45 mg, $1.45\times10^{-2}$ mmol) in DMF (0.5 mL) was then added to the solution. The reaction was stirred for 1.5 h at room temperature under argon while using LC-MS method B: 5-100% to check the reaction progress every 0.5 h. The reaction was complete after 24 h and was then concentrated down under high vacuum. The product was not purified. Yield: 11.41 mg ($1.40\times10^{-2}$ mmol, 96.5%); LC-MS=Calcd. for $C_{26}H_{46}GdN_7O_{11}$: 789.9 (m/z), found: 788.3 $[M-H]^-$.

Compound (38): c(RGDyK)-Su-Lys(Gd)—$NH_2$

To a solution of (37) Su-Lys(Gd-DOTA)-$NH_2$ (5.50 mg, $6.96\times10^{-3}$ mmol) dissolved in DMF (1 mL), DIPA (3.60 mg, $2.79\times10^{-2}$ mmol), HOBt (0.19 mg, $1.39\times10^{-3}$ mmol), and TBTU (2.68 mg, $8.36\times10^{-3}$ mmol) were added. The solution was allowed to pre-activate for 10 minutes. After this pre-activation c(RGDyK) (4.75 mg, $7.66\times10^{-3}$ mmol) dissolved in DMF (1 mL) was added. The reaction was monitored though LC-MS method A. After 20 minutes the reaction was completed. The material was concentrated down under high vacuum and freeze dried. The product was not purified, Yield: 1.2 mg ($8.62\times10^{-4}$ mmol, 12.4%); LC-MS=Calcd. for $C_{51}H_{93}GdN_{17}O_{19}$: 1391.5 (m/z), found: 1389.7 $[M-H]^-$.

Compound (39): SMCC-Lys(Gd-DOTA)-$NH_2$

To a solution of (5) H-Lys(Gd-DOTA)-$NH_2$ (24.00 mg, $3.49\times10^{-2}$ mmol) dissolved in PBS buffer (1 mL) of pH 8.5, the SMCC linker (17.51 mg, $5.24\times10^{-2}$ mmol) in DMF (2 mL) was added. The solution was stirred for 1.5 h at room temperature while using LC-MS method B: 20-100% to check the reaction progress every 0.5 h. Once the reaction was complete, the material was concentrated down. The product was purified through SPE method B: 10-50%. The product was found in fractions 15-25%. Yield: 19.0 mg ($2.10\times10^{-2}$ mmol, 60.0%); LC-MS=Calcd. for $C_{34}H_{52}GdN_8O_{11}$: 906.07 (m/z), found: 904.9 $[M-H]^-$.

Compound (40): c(RGDyK)-SMCC-Lys(Gd-DOTA)-$NH_2$

Figure 4:
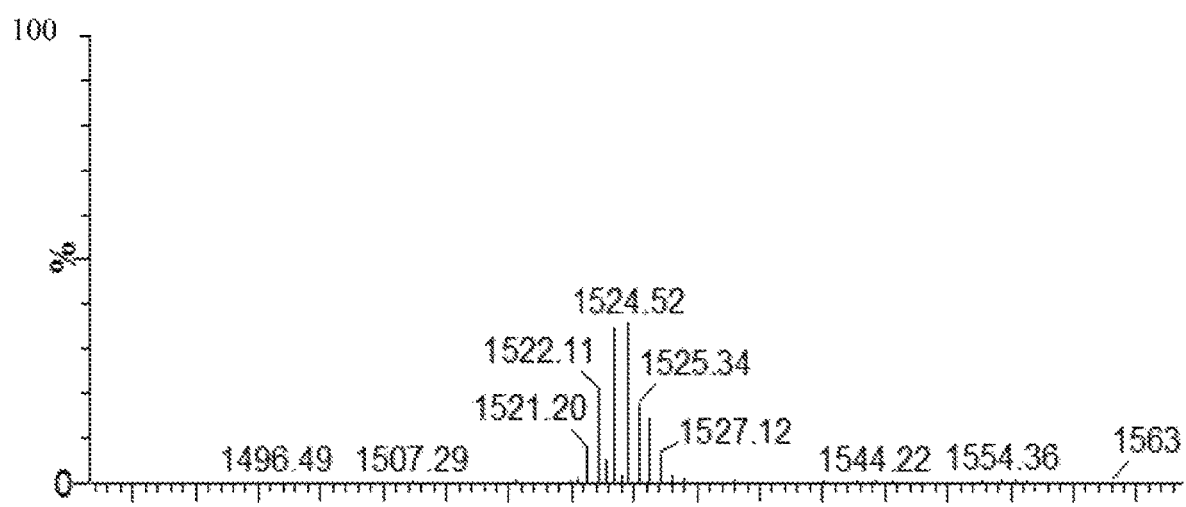
FIG. 4 is a mass spectra of Compound (40) (mono-Gd isotope pattern)

To a solution of (40) SMCC-Lys(Gd-DOTA)-$NH_2$ (4.25 mg, $4.69\times10^{-3}$ mmol) dissolved in NMP (0.25 mL), the targeting peptide c(RGDyK) (2.91 mg, $4.69\times10^{-3}$ mmol) in NMP (0.25 mL) with NMM (0.71 mg, $7.03\times10^{-3}$ mmol) was added. The solution was stirred for 74 h at room temperature while using LC-MS method B: 20-100% to check the reaction progress. After 74 h, additional NMM (1.66 mg, $1.64\times10^{-3}$ mmol) was added to the reaction mixture. After 96 h, additional NMM (0.95 mg, $9.38\times10^{-3}$ mmol) was added. The reaction was stirred during this time and completed after 120 h. Once the reaction was complete, the material was concentrated down. The product was extracted in water with EtOAc and freeze dried, Yield: 2.5 mg ($1.16^{-3}$ mmol, 34.9.0%); LC-MS=Calcd. for $C_{51}H_{93}GdN_{17}O_{19}$: 1525.7 (m/z), found: 1524.5 $[M-H]^-$. The mass spectra of this compound is shown in FIG. 4, displaying the typical Gd isotope pattern.

Compound (41): Su-Lys(Cy5.5)-Lys(Gd-DOTA)-NH$_2$

To a solution of (36a) H-Lys(Cy5.5)-Lys(Gd-DOTA)-NH$_2$ (3.7 mg, 2.22×10$^{-3}$ mmol) dissolved in 50:50 DMF:H$_2$O (1 mL), HOBt (0.03 mg, 2.22×10$^{-4}$ mmol), and TBTU (0.86 mg, 2.67×10$^{-3}$ mmol) were added. Su linker (0.22 mg, 2.22×10$^{-3}$ mmol) in DMF (1 mL) was then added to the solution. The reaction was stirred for 2 h at room temperature under argon while using LC-MS method A to check the reaction progress every 0.5 h. The reaction was complete after 6 h and was then concentrated down under high vacuum. The product was not purified. Yield: 2.0 mg (1.13×10$^{-3}$ mmol, 50.9%); LC-MS=Calcd. for C$_{75}$H$_{104}$GdN$_{11}$O$_{22}$S$_3$: 1765.1 (m/z), found: 1763.7 [M–H]$^-$.

Compound (42): c(RGDyK)-Su-Lys(Cy5.5)-Lys(Gd-DOTA)-NH$_2$

To a solution of (41) Su-Lys(Cy5.5)-Lys(Gd-DOTA)-NH$_2$ (0.53 mg, 2.85×10 mmol) dissolved in DMF (0.50 mL), the targeting peptide c(RGDyK) (0.176 mg, 2.85×10$^{-4}$ mmol) in NMP and DIPA (1.10 mg, 8.54×10$^{-3}$ mmol) were added. The solution was stirred for 4 h at room temperature monitored using LC-MS method B. After 2 h, additional TBTU (1.0 mg, 8.55×10$^{-4}$ mmol) and DIPA (3.0 mg, 2.14×10$^{-2}$ mmol) were added. The reaction was completed in 3 h. Once the reaction was complete, the material was concentrated down through rotary evaporation and high vacuum. Yield: 0.3 mg (1.28×10$^{-4}$ mmol, 45%); LC-MS=Calcd. for C$_{10}$H$_{153}$GdN$_{21}$O$_{30}$S$_3$: 2338.8 (m/z), found: 1168.4[M–H/2]$^-$, 778.6 [M–H/3]$^-$.

Compound (43): SMCC-DLys(Cy5.5)-Lys(Gd-DOTA)-NH$_2$

To a solution of (36b) H-DLys(Cy5.5)-Lys(Gd-DOTA)-NH$_2$ (24.00 mg, 3.49×10$^{-2}$ mmol) dissolved in PBS buffer (1 mL) of pH 7.4, the SMCC linker (17.51 mg, 5.24×10$^{-2}$ mmol) in DMF (2 mL) was added. The solution was stirred for 1 h at room temperature while using LC-MS methanol B: 20-100% to check the reaction progress every 0.5 h. Once the reaction was complete, the material was concentrated down. The product was not purified; the residue was used directly in the next reaction. Yield: 4.1 mg (2.18×10$^{-3}$ mmol, 88.17%); LC-MS=Calcd. for C$_{83}$H$_{112}$GdN$_{12}$O$_{22}$S$_3$: 1883.3 (m/z), found: 941.1 [M–H/2]$^-$.

Compound (44): c(RGDyK)-SMCC-DLys(Cy5.5)-Lys(Gd-DOTA)-NH$_2$

Figure 5:
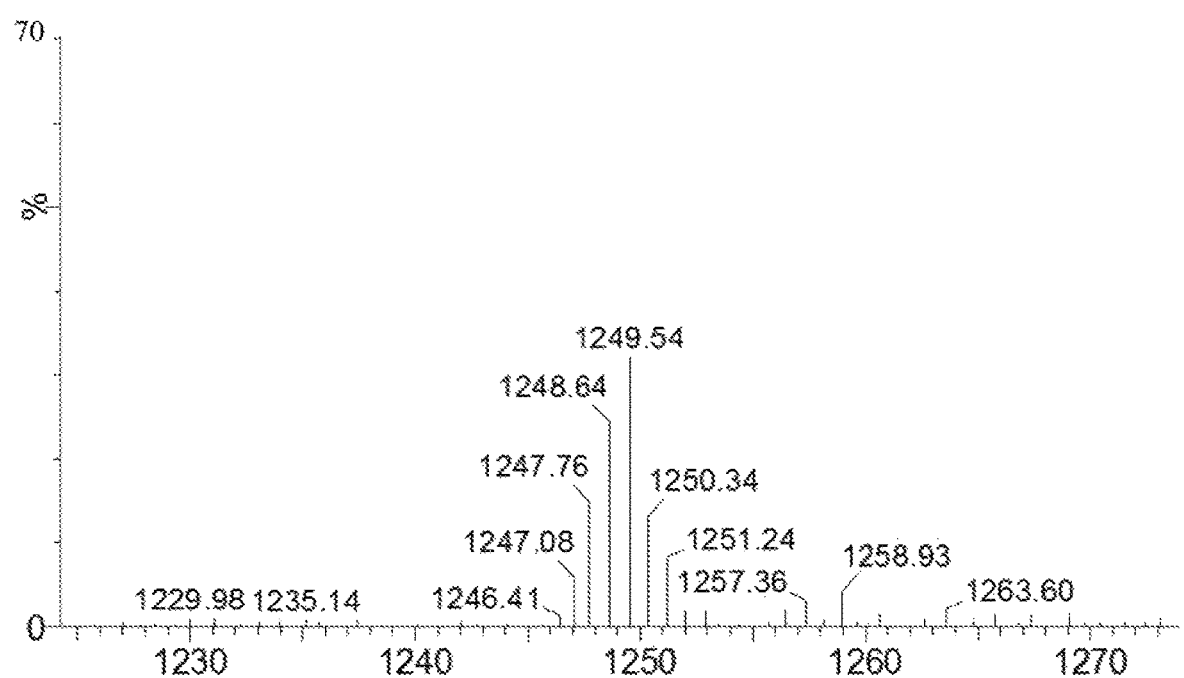
FIG. 5 is a mass spectra of Compound (44) ES:M/2 (mono-Gd isotope pattern)
Figure 6:
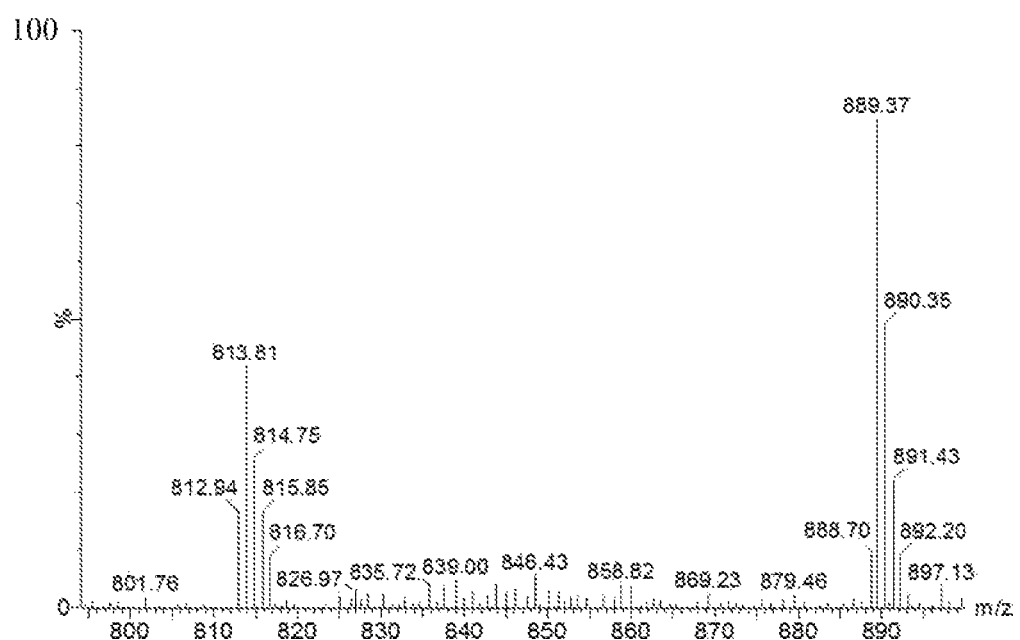
FIG. 6 is a mass spectra of the partial exchange of Cerium to Copper in Compound (11) to Compound (12)
Figure 7:
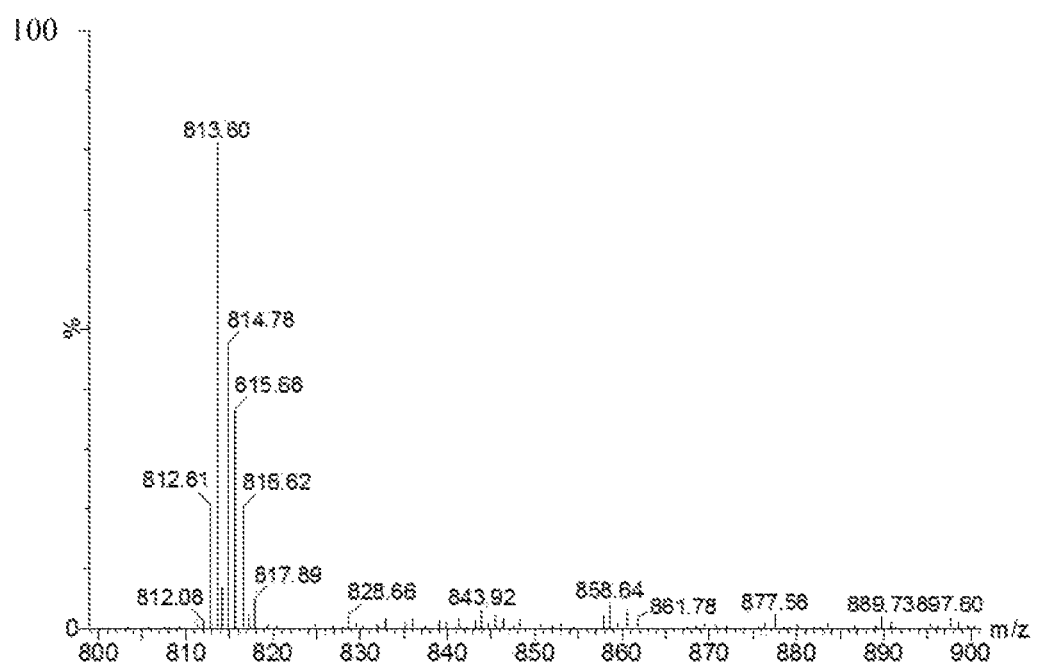
FIG. 7 is a mass spectra of the full exchange of Cerium to Copper in Compound (11) to Compound (12)(same solution vial as FIG. 6), as a model for exchange of Ce to radioactive Cu in a TMIA.

To a solution of (43) SMCC-DLys(Cy5.5)-Lys(Gd-DOTA)-NH$_2$ (4.10 mg, 2.17×10$^{-3}$ mmol) dissolved in NMP (0.25 mL), the targeting peptide c(RGDyK) (2.02 mg, 3.26×10$^{-3}$ mmol) in NMP (0.25 mL) with NMM (0.22 mg, 2.17×10$^{-3}$ mmol) was added. The solution was stirred for 74 h at room temperature while using LC-MS method B: 10-100% to check the reaction progress. After 24 h and 28 h, additional NMM (4.36×10$^{-3}$ mmol) was added. After 36 h, additional c(RGDyK) (3.26×10$^{-3}$ mmol) was added. After 72 h, additional NMM (4.36×10$^{-3}$ mmol) was added. The reaction was completed in 76 h. Once the reaction was complete, the material was concentrated down through rotary evaporation. The product was purified through SPE using method B: 5-50% with product found in fractions 30-40%. Yield: 2.0 mg (7.99×10$^{-4}$ mmol, 36.7%); LC-MS=Calcd. for C$_{110}$H$_{153}$GdN$_{21}$O$_{30}$S$_3$: 2503.1 (m/z), found: 1244.834.1 [M–H/3]$^-$. The molecular weight is beyond the mass range of the instrument utilized, however the half and third masses are clearly visible and are typical for such compounds. The mass spectra of this compound is shown in FIG. 5, displaying the typical Gd isotope pattern.

HPLC Methods

To routinely monitor reactions an Agilent 1100 equipped with a Diode Array detector and auto sampler was utilized with the following general method.

For HPLC-DAD Method A: An Agilent XDBC-18 column or Waters Sunfire C-18 column with an 8 or 10 minute gradient of 10-100% acetonitrile (solvent B) with resultant 90-0% A 0.1 M AmAc (Solvent A) was used unless otherwise denoted in the experimental section (i.e. 30-100% ACN).

Method B: An Agilent XDBC-18 column or Waters Sunfire C-18 column with an 8 or 10 min gradient of 10-100% methanol with resultant 90-0% A 0.1M AmAc (Solvent A) was used unless otherwise noted (i.e. 30-100% MeOH).

Column dimensions were 3 mm by 150 mm, 3 micron particle size, flow rate of 0.5 mL/min. Wavelengths were chosen to monitor distinct functional groups. For example 265 nm was often chosen if the compound contained an Fmoc protecting group. NIR dyes were monitored at their wavelengths as well. For compounds containing the targeting peptide, RGDyK, a wavelength of 270 was diagnostic for the presence of tyrosine (Y).

LC-MS Methods

To monitor reactions and obtain Mass Spectral data concomitantly a Waters 2695 Alliance HPLC with Waters 2998 Diode Array Detector with a Waters 3100 SQ Mass Spectrometer was utilized with the identical HPLC methods as above. Scans were typically monitored by positive and negative ion switching as most of the compounds in this record could be monitored by both, but as there were numbers carboxylates and sulfonates generally negative ionization yielded more sensitivity.

SPE Methods

Conditioning of SPE column: a 20 g C-18 Sep-pack ((Varian Mega Bond Elut 20CC/5GRM)) was conditioned with the organic solvent, then pure DI water followed by loading the column with the dissolved product proceeded by a DI water wash or first MeOH/H$_2$O solution.

Method A: A step gradient of 10-100" acetonitrile 10-100% in 5% increments, 3 or 4 10 mL fractions each, unless otherwise noted (i.e., 30-100% ACN)

Method B: A step gradient of 10-100" methanol 10-100% in 5% increments, 3 or 4 10 mL fractions each, unless otherwise noted (i.e., 30-100% ACN).

CFM Methods

The general protocol for Confocal Microscopy by Chen, et al was followed with the following detailed procedures for cell culture and staining.

Cell Preparation: An A549 culture obtained from the American Type Culture Collection (ATCC) was grown to 50-70% confluency in an In Vitro Scientific 35 mm culture dish with 10 mm Glass bottom well. The culture was incubated in DMEM (Dulbecco's Modified Eagle Medium) with 10% Fetal Bovine Serum (FBS) overnight at 37° C. and 5% CO$_2$. To obtain a suspension cell culture for transfer purpose, the cells were washed with Phosphate Buffered Saline (PBS) and then 0.25% Trypsin-EDTA (1×) (Invitrogen) was added to detach the cells.

Cell Staining: The cells were washed 3× with pre-heated PBS (Phosphate-buffered saline). 5 µM c(RGDyK) peptide conjugates (TMIAs) were added to the 10 mm glass bottom well and incubated at 37° C. and 5% CO$_2$. Cells were then washed 4× with chilled PBS. The samples were viewed immediately under the scanning laser confocal microscope (Leica Microsystems Inc.). Confocal Microscopy Scanning: Leica TCS SP5 II AOBS Filter Free Tunable Spectral Confocal Research Microscope with Resonant Scanner and Hybrid Detectors attached to Leica DMI6000 Fully Automated Microscope was used, with 40× water immersion objective. The 405 Diode and HeNe633 lasers were employed for visualizing suspected auto-fluorescence, c(RGDyK) Cy5.5-TMIA respectively. Images of stained cells were obtained using a sequential scan. The final image was captured at 1000 Hz with a resolution of 1024×1024 pixel and frame average of 6. LAS AF software was used to analyze the data. Shown in FIG. 1 is a CFM Image of live A549 human cancer cells after 2 hours incubation with of TMIA Compound (44). The image is of one cell with the illuminated areas a result of fluorescence of the TMIA. The dark area within the cell is the nucleus.

T1 Relaxation Time Measurements in NMR Methods

Figure 2:
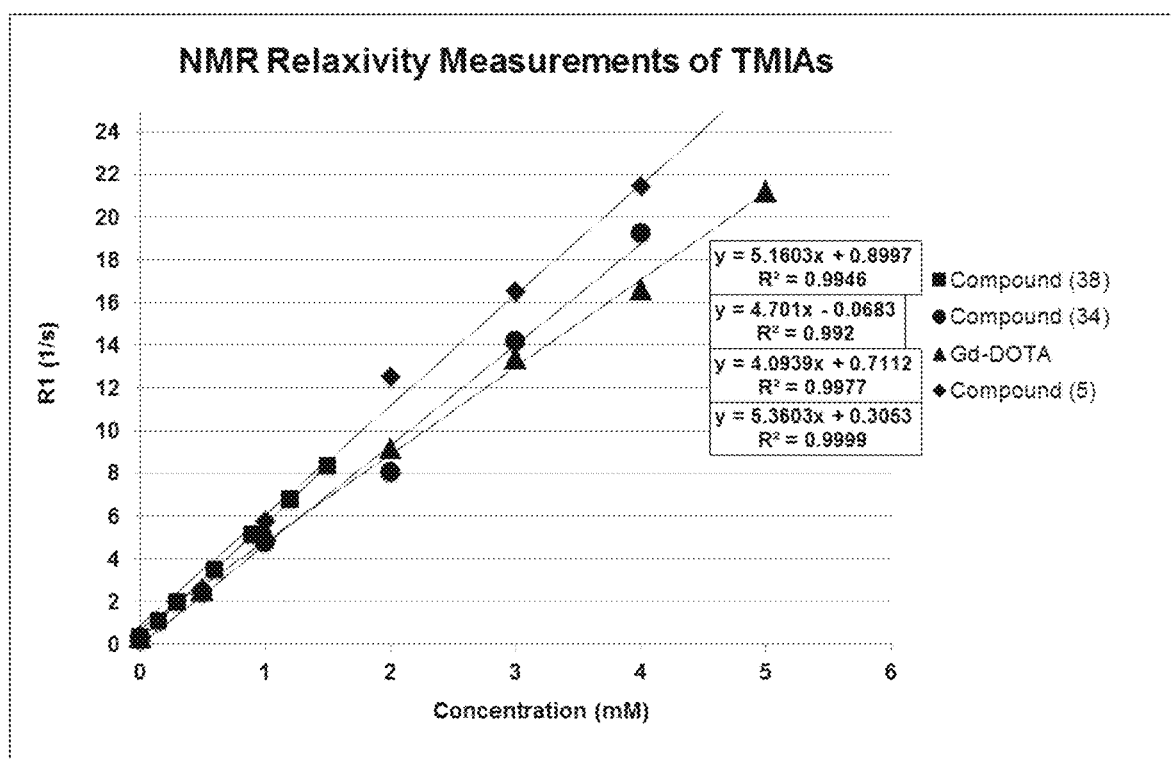
FIG. 2 is a graph of NMR T1 relaxation times of selected compounds and a standard (Gd-DOTA) from the method in Hornak, et al.

To assess the contrast efficacy of agents containing gadolinium (Gd) T1 relaxation times were measured by the method of Hornak, et al. As a standard the compound Gd(DOTA), also known as Gadovist (Macrocyclics) was utilized. Measurements in this case were obtained on a Magritek Spinsolve bench top NMR with frequency 42.5 MHz. FIG. 2 shows NMR T1 relaxation times of selected compounds and standard (Gd-DOTA). Method is by Hornak, et al.

ABBREVIATIONS

ACN: Acetonitrile
Ad: Adipic anhydride or Adipate
AmAc: ammonium acetate
Bn: Benzyl
CB-TETA: 4,11-bis(carboxymethyl)-1,4,8,11-tetraazabicyclo[6.6.2]hexadecane
CB-Cyclam: 1,4,8,11-tetraazabicyclo[6.6.2]hexadecane
Cbz: Carboxybenzyl
CFM: Confocal Fluorescence Microscopy
COMU: (1-Cyano-2-ethoxy-2-oxoethylidenaminooxy)dimethylamino-morpholinocarbenium hexafluoro-phosphate, 98% FW 428.27
DCM: Dichloromethane
DEA: Diethylamine
DIPA: Diisopropylamine
DMF: Dimethylformamide
DO3A: A DOTA-Alanine derivative (see Ferreira, et al)
DOTAla: DOTA attached from ring N to Alanine, analogous to DO3A (Caravan, et al)
DOTA-triTBu: Tri-tert-butyl 1,4,7,10-Tetraazacyclododecane-1,4,7,10-tetraacetate
DOTAM: 1,4,7,10-tetrakis(carbamoylmethyl)-1,4,7,10-tetraazacyclododecane
DTPA: diethylene triamine pentaacetic acid
EDC: 1-Ethyl-3-(3-dimethylaminopropyl)carbodiimide
EtOAc: Ethyl acetate
Fmoc: Fluorenylmethoxycarbonyl
FRET: fluorescence resonance imaging transfer
Gd(OAc): Gadolinium acetate
Gl: Glutaric anhydride or Glutarate
HATU: 1-[Bis(dimethylamino)methylene]-1H-1,2,3-triazolo[4,5-b]pyridinium 3-oxid hexafluorophosphate
HOAt: 1-Hydrox7-7-azabenzotriazole
HOBt: Hydroxybenzotriazole
LC-MS: Liquid Chromatography-Mass Spectrometry
Lys: Lysine
MeOH: Methanol
MR: magnetic resonance
MRI: magnetic resonance imaging
Mtt: Methyltrityl
NHS: N-hydroxy succinimide
NIR: near infrared (dye or imaging)
NIRF: near infrared fluorescence (dye or imaging)
NMM: N-methylmorpholine
NMP: N-Methyl-2-pyrrolidone
NOTA: 2-(4,7-bis(2-(tert-butoxy)-2-oxoethyl)-1,4,7-triazonan-1-yl)acetic acid
NP: Nanoparticle
OtBu: t-butyl
Pd—C: Palladium on carbon
PAI: photo-acoustic imaging
Pep: peptide
PET: positron emission tomography
PBS: Phosphate buffered saline
SMCC: Succinimidyl-4-(N-maleimidomethyl)cyclohexane-1-carboxylate
SPE: Solid Phase Extraction
SPECT: single photon emission tomography
Su: Succinic Anhydride or Succinate
SS: Solid Support
TBTU: 2-(1H-Benzotriazole-1-yl)-1,1,3,3-tetramethyluronium tetrafluoroborate
TE2A: (1,8-bis(acetic acid)-1,4,8,11-teraazacyclotetradecane)
TETA: Triethylenetetramine
TFA: Trifluoroacetic acid Although various embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A process for synthesizing a targeted imaging agent comprising:
   providing an amino acid or amino amide that does not comprise a protected side chain and that comprises a) a protected, activated, or free acid, b) a protected or free amine, or c) both a) and b);
   attaching a chelated metal or coupling a dye to the unprotected side chain of the amino acid or amino amide—prior to coupling to another amino acid, peptide, or targeting group—to form an amino acid or amino amide imaging agent; and then
   coupling a targeting group comprising a free amine, thiol, or free acid to the amino acid or amino amide imaging agent at the a) protected, activated, or free acid, b) protected or free amine, or c) both a) and b) of the amino acid or amino acid, to form the targeted imaging agent.

2. The process according to claim 1, wherein the metal comprises Gd, Eu, Ce, Cu, Tc, Ge, Ho, Tm, In, or Ga.

3. The process according to claim 1, further comprising exchanging the metal in the chelated metal of the targeted imaging agent with a radioactive metal.

4. The process according to claim 1, wherein the coupling of the amino acid or amino amide imaging group to a targeting agent comprises coupling the free amine, free acid or thiol of the targeting group through a linker.

5. The process according to claim 1, wherein the protected amine is protected by protecting groups comprising Boc, Mtt, Fmoc, Cbz, Alloc, or DMAB and the protected acid is protected by OBn, OMe, OEt, OtBu, OPMB or O-Alloc protecting groups.

6. The process according to claim 1, wherein the targeting group comprises a peptide, protein, antibody, nanobody, aptamer, RNA, DNA, biomarker, small molecule inhibitor, dendrimer, polymer, or nanoparticle.

7. The process according to claim 1, wherein the amino acid or amino amide imaging agent having a chelated metal or a dye coupled to the amino acid or amino amide comprises a compound comprising:

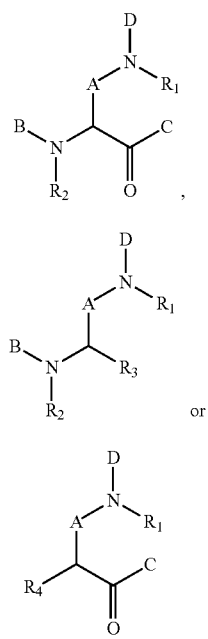

wherein:
A is $(CH_2)_n$, wherein n is 1-10;
B is a moiety selected from H, Fmoc, Cbz, Boc, Mtt, or Alloc;
C is a moiety selected from OH, $OR_5$, $NH_2$, or an activating group;
D is a dye, or metal-chelate complex, attached directly, or via a linker;
$R_1$ is H, $CH_3$, or $CH_2CH_3$;
$R_2$ is H, $CH_3$, or $CH_2CH_3$;
$R_3$ is H, $CH_3$, or $CH_2CH_3$;
$R_4$ is H, $CH_3$, or $CH_2CH_3$; and
$R_5$ is H, $CH_3$, or $CH_2CH_3$.

8. The process according to claim 1, wherein the coupling of the amino acid or amino amide imaging agent to the targeting group comprises coupling the protected or free acid or the protected or free amine of the amino acid or amino amide through the free amine, thiol, or free acid of the targeting group.

9. The process according to claim 1, wherein the amino acid imaging agent comprises a protected, activated, or free acid, and a protected or free amine.

10. The process according to claim 1, wherein the amino amide imaging agent comprises an amide and a protected or free amine.

11. The process according to claim 1, wherein the chelated metal comprises an exchangeable metal.

12. The process according to claim 1, wherein the targeting group is capable of binding to diseased cells.

13. The process according to claim 1, further comprising purifying the amino acid or amino amide imaging group prior to coupling with the targeting agent.

14. A process for synthesizing a multiple amino acid or amino amide targeted imaging agent comprising:

providing an amino acid or amino amide that does not comprise a protected side chain and that comprises a) a protected, activated, or free acid, b) a protected or free amine, or c) both a) and b);

attaching a chelated metal or coupling a dye to the unprotected side chain of the amino acid or amino amide - prior to coupling to another amino acid, peptide, or targeting group - to form a first modular amino acid or amino amide imaging agent; and then providing for coupling that first modular amino acid having an amine, an acid, and a side chain containing an imaging agent comprising a first chelated metal or a first dye, or a first modular amino amide having an amine, an amide, and a side chain containing an imaging agent comprising a first chelated metal or a first dye;

coupling the amine of the first modular amino acid or the amine of the first modular amino amide to an acid of a second modular amino acid having an amine, an acid, and a side chain containing an imaging agent comprising a second chelated metal or a second dye; or coupling the acid of the first modular amino acid to an amine of the second modular amino acid or the amine of a second modular amino amide having an amine, an amide, and a side chain containing an imaging agent comprising a second chelated metal or a second dye to provide a multiple amino acid or amino amide imaging agent in a peptide chain comprising a protected or free acid or a protected or free amine; and then coupling a targeting group comprising a free amine, thiol, or free acid to the amino acid or amino amide imaging agent at the a) protected, activated, or free acid, b) protected or free amine, or c) both a) and b) of the amino acid or amino acid, to form a multiple amino acid or amino amide targeted imaging agent.

15. The process according to claim 14, wherein the multiple amino acid or amino amide imaging agent comprises a compound comprising:

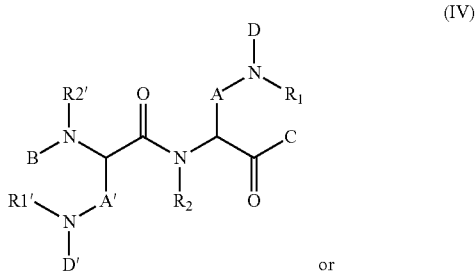

or

-continued (V)

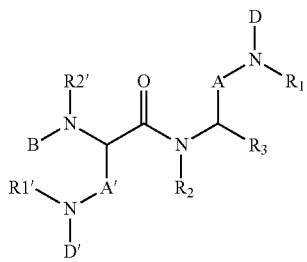

wherein:
A and A' are independently $(CH_2)_n$, wherein n is 1-10;
B is a moiety selected from H, Fmoc, Cbz, Boc, Mtt, or Alloc;
C is a moiety selected from OH, $OR_5$, $NH_2$, or an activating group;
D and D' are each independently a dye, or metal-chelate complex, attached directly, or via a linker;
$R_1$ and $R_1'$ are independently H, $CH_3$, or $CH_2CH_3$;
$R_2$ and $R_2'$ are independently H, $CH_3$, or $CH_2CH_3$;
$R_3$ is H, $CH_3$, or $CH_2CH_3$;
$R_4$ is H, $CH_3$, or $CH_2CH_3$; and
$R_5$ is H, $CH_3$, or $CH_2CH_3$.

16. The process according to claim 14, wherein the multiple amino acid or amino amide imaging agent comprises a compound comprising:

(VI)

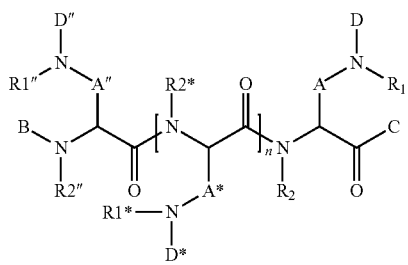

-continued (VII)

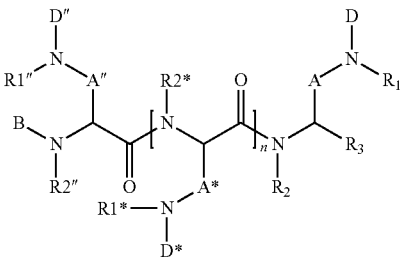

wherein:
$[\ ]_n$ represents a polypeptide chain of variable length;
A, A" and A* are each independently $(CH_2)_n$, wherein n is 1-10, and A* is a variable designation;
B is a moiety selected from H, Fmoc, Cbz, Boc, Mtt, or Alloc;
C is a moiety selected from OH, $OR_5$, $NH_2$, or an activating group; D, D" and D* are each independently a dye, or metal-chelate complex, attached directly, or via a linker, and D* is a variable designation;
$R_1$, $R_1"$ and $R_1*$ are each independently H, $CH_3$, or $CH_2CH_3$; and $R_1*$ is a variable designation;
$R_2$, $R_2"$ and $R_2*$ are each independently H, $CH_3$, or $CH_2CH_3$; and $R_2*$ is a variable designation;
$R_3$ is H, $CH_3$, or $CH_2CH_3$;
$R_4$ is H, $CH_3$, or $CH_2CH_3$; and
$R_5$ is H, $CH_3$, or $CH_2CH_3$.

17. The process according to claim 14, wherein the first chelated metal is different than the second chelated metal.

18. The process according to claim 14, wherein the first dye is different than the second dye.

* * * * *

UNITED STATES PATENT AND TRADEMARK OFFICE
CERTIFICATE OF CORRECTION

PATENT NO. : 10,610,608 B2
APPLICATION NO. : 14/449943
DATED : April 7, 2020
INVENTOR(S) : Hans Schmitthenner et al.

Page 1 of 1

It is certified that error appears in the above-identified patent and that said Letters Patent is hereby corrected as shown below:

In the Claims

Column 88, Line 55, in Claim 1, the wording amino acid or amino acid should read amino acid or amino amide Signed and Sealed this
Twelfth Day of January, 2021

Andrei Iancu
*Director of the United States Patent and Trademark Office*